United States Patent
Haybaeck et al.

(10) Patent No.: US 11,788,086 B2
(45) Date of Patent: Oct. 17, 2023

(54) ANTITUMOR COMPOUNDS AND TUMOR DIAGNOSIS

(71) Applicant: CBMED GMBH CENTER FOR BIOMARKER RESEARCH IN MEDICINE, Graz (AT)

(72) Inventors: Johannes Haybaeck, Linz (AT); Nicole Golob-Schwarzl, Graz (AT); Stefanie Krassnig, Graz (AT); Nadine Thaler, Graz (AT); Julia Judith Unterluggauer, St. Michael im Lavanttal (AT); Alexander Deutsch, Graz (AT)

(73) Assignee: CBMED GMBH CENTER FOR BIOMARKER RESEARCH IN MEDICINE, Graz (AT)

( * ) Notice: Subject to any disclaimer, the term of this patent is extended or adjusted under 35 U.S.C. 154(b) by 0 days.

(21) Appl. No.: 16/322,814

(22) PCT Filed: Jul. 27, 2017

(86) PCT No.: PCT/EP2017/069053
§ 371 (c)(1),
(2) Date: Feb. 1, 2019

(87) PCT Pub. No.: WO2018/024608
PCT Pub. Date: Feb. 8, 2018

(65) Prior Publication Data
US 2021/0054374 A1 Feb. 25, 2021

(30) Foreign Application Priority Data

Aug. 3, 2016 (EP) .................................. 16182554
Apr. 12, 2017 (EP) .................................. 17166262

(51) Int. Cl.
*C12N 15/113* (2010.01)
*C12Q 1/6886* (2018.01)
*G01N 33/574* (2006.01)

(52) U.S. Cl.
CPC .......... *C12N 15/113* (2013.01); *C12Q 1/6886* (2013.01); *G01N 33/57407* (2013.01); *G01N 33/57419* (2013.01); *G01N 33/57423* (2013.01); *G01N 33/57496* (2013.01); *C12N 2310/14* (2013.01); *C12Q 2600/118* (2013.01); *C12Q 2600/158* (2013.01)

(58) Field of Classification Search
CPC ....... G01N 33/57407; G01N 33/57423; C12N 15/113; C12Q 1/6886
See application file for complete search history.

(56) References Cited

FOREIGN PATENT DOCUMENTS

| WO | 2007/070824 A2 | 6/2007 |
| WO | 2011052906 A2 | 5/2011 |
| WO | 2012/049636 A1 | 4/2012 |

OTHER PUBLICATIONS

Gura, Systems for identifying new drugs are often faulty, Science, 1997, 278:1041-1042 (Year: 1997).*
Kaiser, First pass at cancer genome reveals complex landscape, Science, 2006, 313: 1370 (Year: 2006).*
Miluzio et al., Expression and activity of eIF6 trigger Malignant Pleural Mesothelioma growth in vivo, Oncotarget 6, 35, 37471-37485, Publication Date: Oct. 6, 2015 (Year: 2015).*
Rao et al., siRNA vs. shRNA: Similarities and differences, Advanced Drug Delivery Reviews, 61, 746-759, Publication Date: Apr. 20, 2009 (Year: 2009).*
Pei and Tuschl, On the art of identifying effective and specific siRNAs, Nature Methods, 2006, 3: 670-676, Publication Date: Aug. 23, 2006 (Year: 2006).*
Wang et al., Strategies for short hairpin RNA delivery in cancer gene therapy, Expert Opin. Biol. Ther. 2009 9(11): 1357-1368, Publication Date: Sep. 18, 2009 (Year: 2009).*
EIF6 Genecard: retrieved from: https://www.genecards.org/cgi-bin/carddisp.pl?gene=EIF6, on Sep. 20, 2021 (Year: 2021).*
Sanvito et al., Expression of a Highly Conserved Protein, p27BBP, during the Progression of Human Colorectal Cancer, Cancer Research: 60, 510-516, Publication Date:Feb. 1, 2000 (Year: 2000).*
Tang et al., Chinese Journal of Oncology, 32, 07, 2010, Expression and significance of P311 and ITGB4BP in non-small cell lung cancer (Year: 2010).*
English Translated version: Tang et al., Expression and significance of P311 an d ITGB4BP in non-small cell lung cancer, Chinese Journal of Oncology, 32, 07, 2010, 526-528, Publication Date: Jul. 2010 (Year: 2010).*

(Continued)

*Primary Examiner* — Peter J Reddig
*Assistant Examiner* — Cheng Lu
(74) *Attorney, Agent, or Firm* — Kilpatrick Townsend & Stockton LLP

(57) ABSTRACT

The present invention relates to a eukaryotic initiation factor (eIF) modulating compound for use in the treatment of a tumor and in the diagnosis of a cancer. The present invention also relates to a method of diagnosing lung cancer in an individual and to a method of providing a prognosis to an individual suffering from lung cancer. Furthermore, the present invention relates to a method of diagnosing colorectal cancer in an individual, a method of differentiating between colon cancer (CC) and rectum cancer (RC) in an individual, a method of determining whether an individual responds to a therapeutic treatment of colorectal cancer, and to a method of determining the course of colorectal cancer in an individual. Furthermore, the present invention relates to a method of diagnosing a glioma in an individual, a method of grading a glioma in an individual, a method of differentiating between a low-grade glioma and a high-grade glioma in an individual, a method of determining whether an individual responds to a therapeutic treatment of a glioma, and a method of determining the course of a glioma in an individual. In addition, the present invention relates to a kit for conducting the above mentioned methods.

6 Claims, 62 Drawing Sheets
Specification includes a Sequence Listing.

(56) References Cited

OTHER PUBLICATIONS

Peng et al., Identification of ITGB4BP as a new interaction protein of P311, Life Sciences 90 (2012) 585-590, (Year: 2012).*
International Search Report in PCT/EP2017/069053, dated Feb. 22, 2018.
De Benedetti, et al. "eIF-4E expression and its role in malignancies and metastases." Oncogene 23, No. 18 (2004): 3189.
Jin, et al. "Suppression of primary and disseminated murine tumor growth with eIF5A1 gene therapy." Gene Ther Mol Biol 12, No. 2 (2008): 207-218.
Li, et al. "Increased expression of EIF5A2, via hypoxia or gene amplification, contributes to metastasis and angiogenesis of esophageal squamous cell carcinoma." Gastroenterology 146, No. 7 (2014): 1701-1713.
Li, et al. "Overexpression of eIF3e is correlated with colon tumor development and poor prognosis." International journal of clinical and experimental pathology 7, No. 10 (2014): 6462.
Mathews, et al. "The translation factor eIF5A and human cancer." Biochimica et Biophysica Acta (BBA)-Gene Regulatory Mechanisms 1849, No. 7 (2015): 836-844.
Nasr, et al. "eIF4F suppression in breast cancer affects maintenance and progression." Oncogene 32, No. 7 (2013): 861.
Tang, et al. "Overexpression of eukaryotic initiation factor 5A2 enhances cell motility and promotes tumor metastasis in hepatocellular carcinoma." Hepatology 51, No. 4 (2010): 1255-1263.
Wang, et al. "Roles of eukaryotic initiation factor 5A2 in human cancer." International journal of biological sciences 9, No. 10 (2013): 1013.

* cited by examiner

Figure 7A
eIF3A
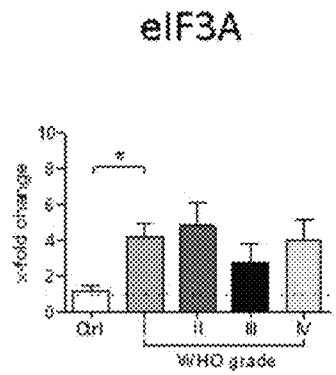
Figure 7B
eIF3B
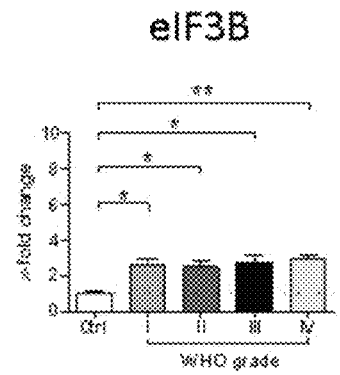
Figure 7E
eIF3M
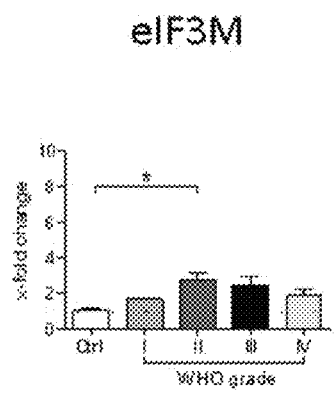
eIF4A1    Figure 7F
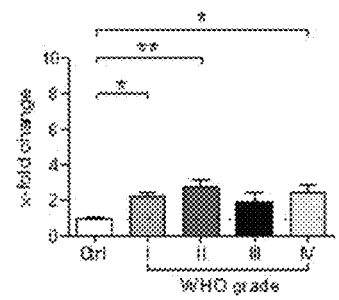
eIF4G1
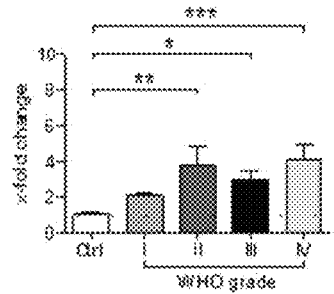
eIF4H
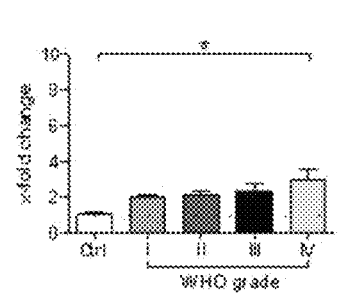
Figure 7I
Figure 7J

Figure 7C
eIF3C
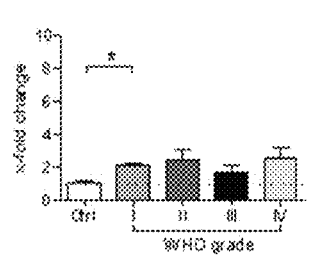
Figure 7D
eIF3I
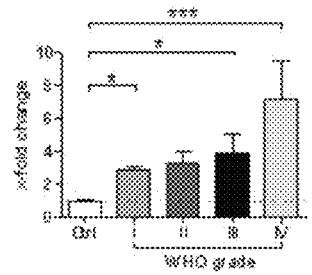
Figure 7G
eIF4E
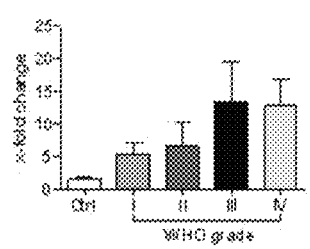
eIF4EBP1
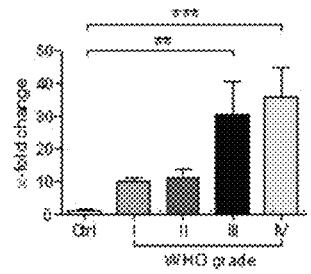
Figure 7H
eIF5
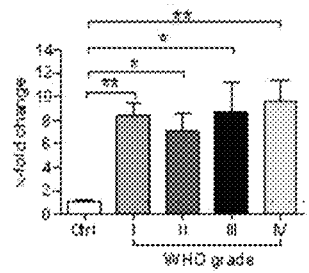
eIF6
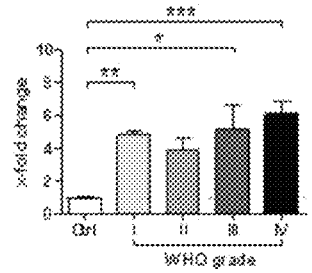
Figure 7K
Figure 7L

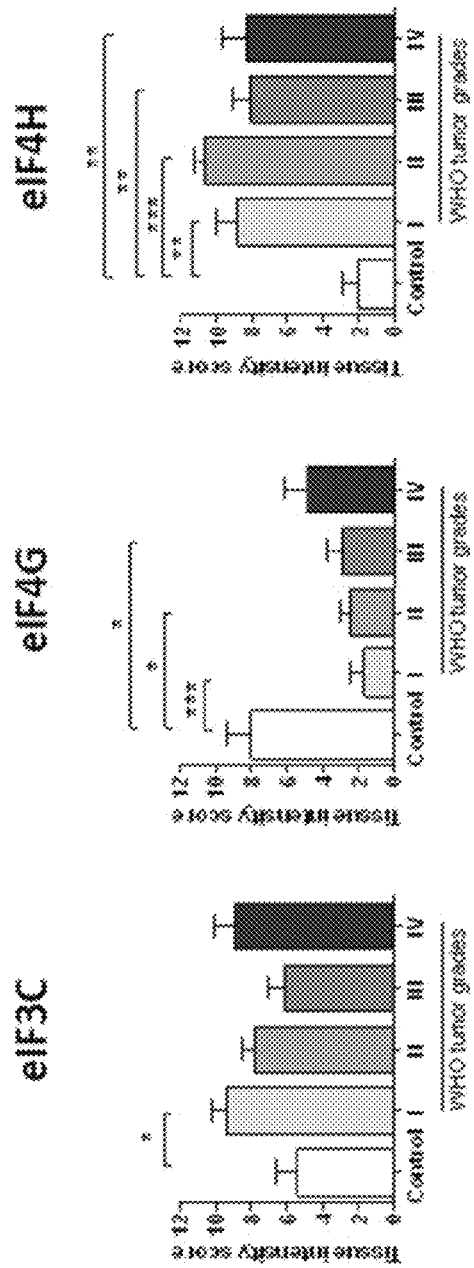
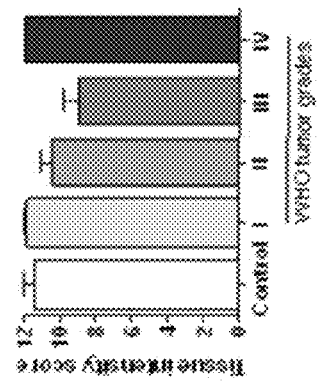
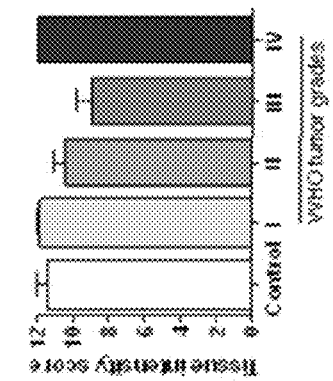
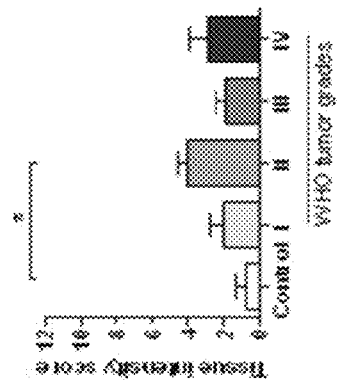
Figure 9A  Figure 9B  Figure 9C
Figure 9D  Figure 9E

FIGURE 21A
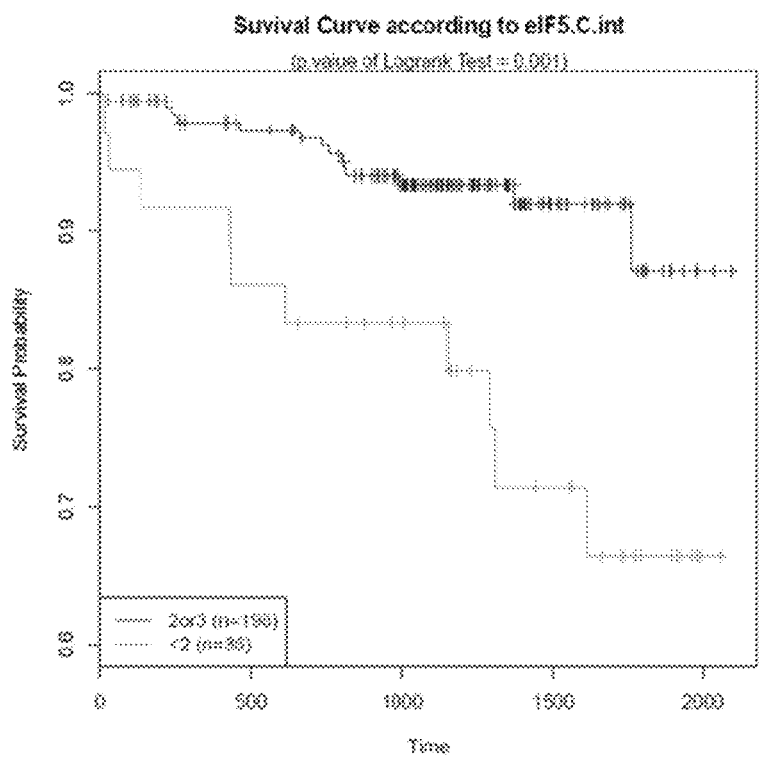
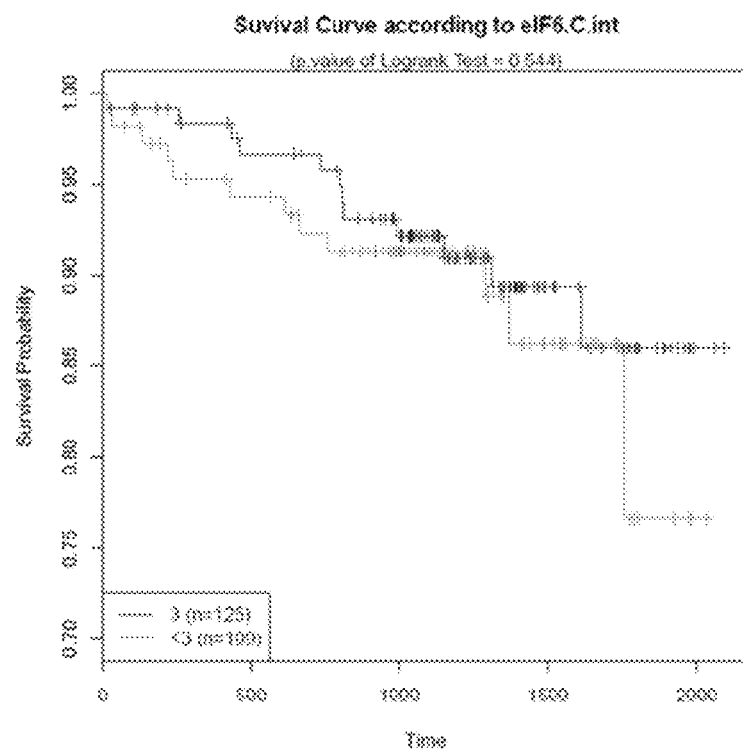
FIGURE 21B

FIGURE 22A
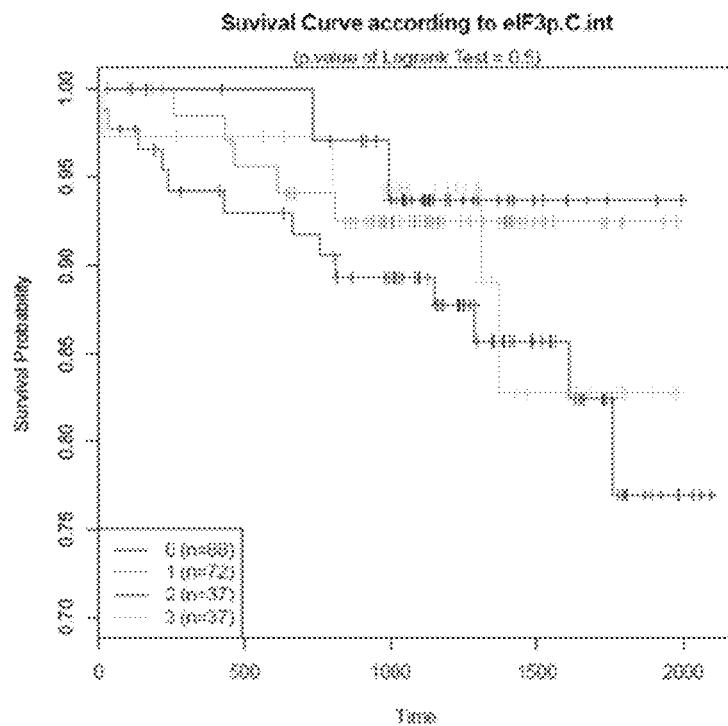
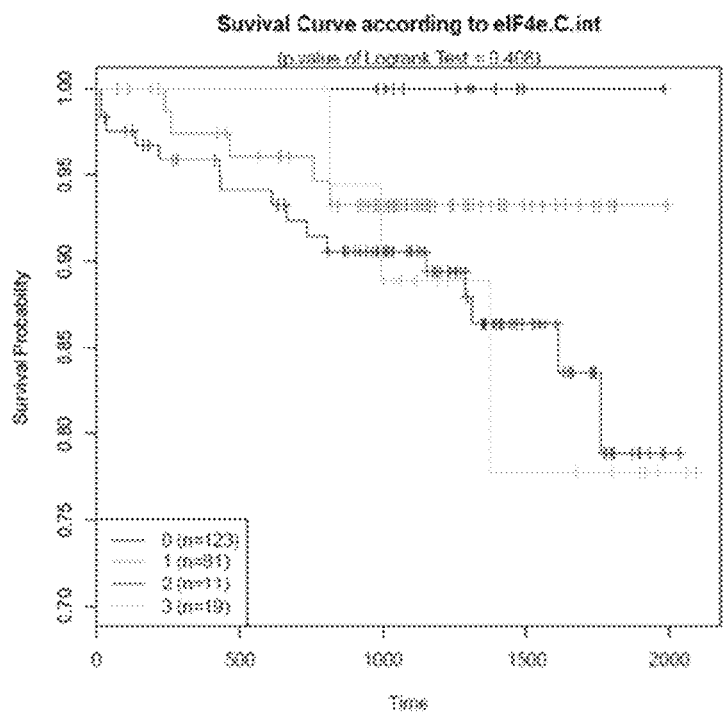
FIGURE 22B

FIGURE 29A
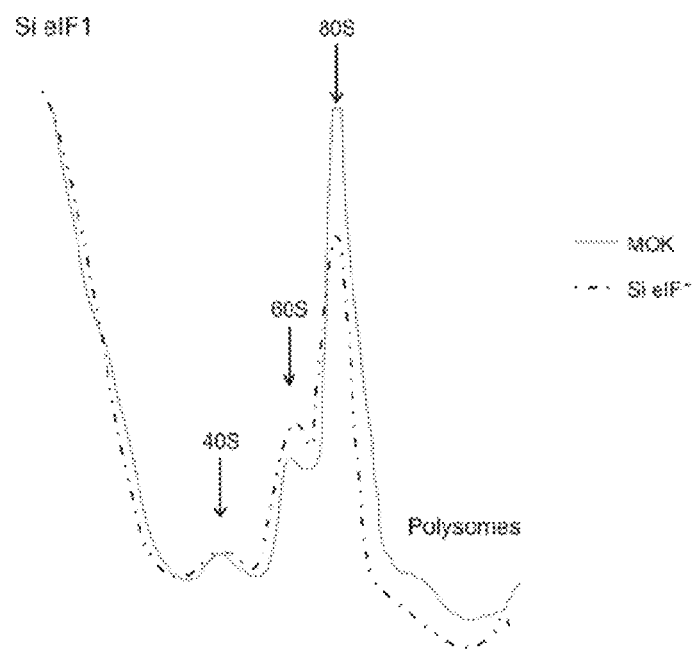
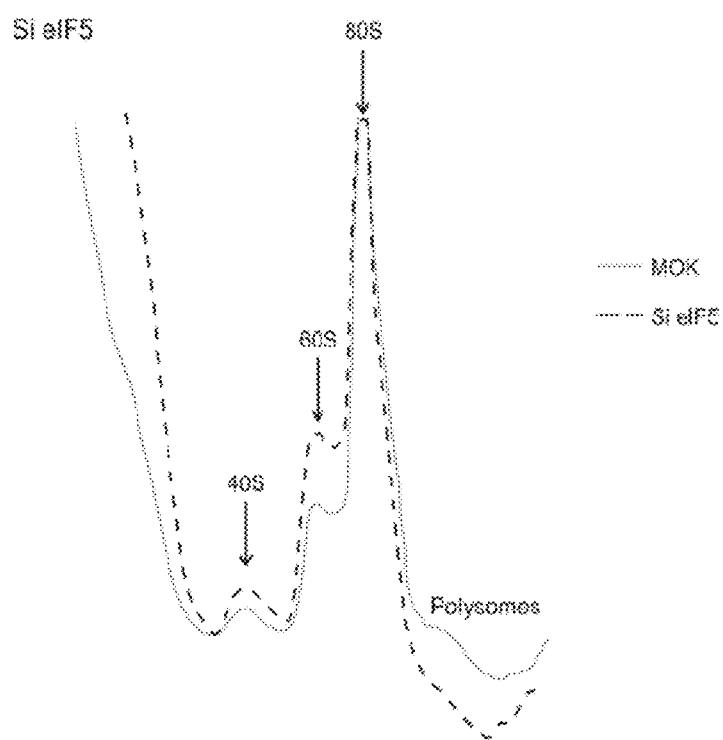
FIGURE 29B

FIGURE 33

| No. | eIF1A | eIF6 |
|---|---|---|
|  |  |  |
| 1 | eIF1A |  |
| 2 |  | eIF6 |
| 3 | eIF1A | eIF6 |

FIGURE 34

| No. | eIF3I | eIF3M | eIF4A | eIF4H | eIF5 | eIF6 |
|---|---|---|---|---|---|---|
|  |  |  |  |  |  |  |
| 1 |  |  |  |  |  | eIF6 |
| 2 |  |  |  |  | eIF5 |  |
| 3 |  |  |  |  | eIF5 | eIF6 |
| 4 |  |  |  | eIF4H |  |  |
| 5 |  |  |  | eIF4H |  | eIF6 |
| 6 |  |  |  | eIF4H | eIF5 |  |
| 7 |  |  |  | eIF4H | eIF5 | eIF6 |
| 8 |  |  | eIF4A |  |  |  |
| 9 |  |  | eIF4A |  |  | eIF6 |
| 10 |  |  | eIF4A |  | eIF5 |  |
| 11 |  |  | eIF4A |  | eIF5 | eIF6 |
| 12 |  |  | eIF4A | eIF4H |  |  |
| 13 |  |  | eIF4A | eIF4H |  | eIF6 |
| 14 |  |  | eIF4A | eIF4H | eIF5 |  |
| 15 |  |  | eIF4A | eIF4H | eIF5 | eIF6 |
| 16 |  | eIF3M |  |  |  |  |
| 17 |  | eIF3M |  |  |  | eIF6 |
| 18 |  | eIF3M |  |  | eIF5 |  |
| 19 |  | eIF3M |  |  | eIF5 | eIF6 |
| 20 |  | eIF3M |  | eIF4H |  |  |
| 21 |  | eIF3M |  | eIF4H |  | eIF6 |
| 22 |  | eIF3M |  | eIF4H | eIF5 |  |
| 23 |  | eIF3M |  | eIF4H | eIF5 | eIF6 |
| 24 |  | eIF3M | eIF4A |  |  |  |
| 25 |  | eIF3M | eIF4A |  |  | eIF6 |
| 26 |  | eIF3M | eIF4A |  | eIF5 |  |
| 27 |  | eIF3M | eIF4A |  | eIF5 | eIF6 |
| 28 |  | eIF3M | eIF4A | eIF4H |  |  |
| 29 |  | eIF3M | eIF4A | eIF4H |  | eIF6 |
| 30 |  | eIF3M | eIF4A | eIF4H | eIF5 |  |
| 31 |  | eIF3M | eIF4A | eIF4H | eIF5 | eIF6 |
| 32 | eIF3I |  |  |  |  |  |
| 33 | eIF3I |  |  |  |  | eIF6 |
| 34 | eIF3I |  |  |  | eIF5 |  |
| 35 | eIF3I |  |  |  | eIF5 | eIF6 |
| 36 | eIF3I |  |  | eIF4H |  |  |

FIGURE 34 (CONT.)

| | | | | | | |
|---|---|---|---|---|---|---|
| 37 | eIF3I | | | eIF4H | | eIF6 |
| 38 | eIF3I | | | eIF4H | eIF5 | |
| 39 | eIF3I | | | eIF4H | eIF5 | eIF6 |
| 40 | eIF3I | | eIF4A | | | |
| 41 | eIF3I | | eIF4A | | | eIF6 |
| 42 | eIF3I | | eIF4A | | eIF5 | |
| 43 | eIF3I | | eIF4A | | eIF5 | eIF6 |
| 44 | eIF3I | | eIF4A | eIF4H | | |
| 45 | eIF3I | | eIF4A | eIF4H | | eIF6 |
| 46 | eIF3I | | eIF4A | eIF4H | eIF5 | |
| 47 | eIF3I | | eIF4A | eIF4H | eIF5 | eIF6 |
| 48 | eIF3I | eIF3M | | | | |
| 49 | eIF3I | eIF3M | | | | eIF6 |
| 50 | eIF3I | eIF3M | | | eIF5 | |
| 51 | eIF3I | eIF3M | | | eIF5 | eIF6 |
| 52 | eIF3I | eIF3M | | eIF4H | | |
| 53 | eIF3I | eIF3M | | eIF4H | | eIF6 |
| 54 | eIF3I | eIF3M | | eIF4H | eIF5 | |
| 55 | eIF3I | eIF3M | | eIF4H | eIF5 | eIF6 |
| 56 | eIF3I | eIF3M | eIF4A | | | |
| 57 | eIF3I | eIF3M | eIF4A | | | eIF6 |
| 58 | eIF3I | eIF3M | eIF4A | | eIF5 | |
| 59 | eIF3I | eIF3M | eIF4A | | eIF5 | eIF6 |
| 60 | eIF3I | eIF3M | eIF4A | eIF4H | | |
| 61 | eIF3I | eIF3M | eIF4A | eIF4H | | eIF6 |
| 62 | eIF3I | eIF3M | eIF4A | eIF4H | eIF5 | |
| 63 | eIF3I | eIF3M | eIF4A | eIF4H | eIF5 | eIF6 |
| 64 | | | | | | |
| 65 | | | | | | eIF6 |
| 66 | | | | | eIF5 | |
| 67 | | | | | eIF5 | eIF6 |
| 68 | | | | eIF4H | | |
| 69 | | | | eIF4H | | eIF6 |
| 70 | | | | eIF4H | eIF5 | |
| 71 | | | | eIF4H | eIF5 | eIF6 |
| 72 | | | eIF4A | | | |
| 73 | | | eIF4A | | | eIF6 |
| 74 | | | eIF4A | | eIF5 | |
| 75 | | | eIF4A | | eIF5 | eIF6 |
| 76 | | | eIF4A | eIF4H | | |
| 77 | | | eIF4A | eIF4H | | eIF6 |
| 78 | | | eIF4A | eIF4H | eIF5 | |
| 79 | | | eIF4A | eIF4H | eIF5 | eIF6 |
| 80 | | eIF3M | | | | |
| 81 | | eIF3M | | | | eIF6 |
| 82 | | eIF3M | | | eIF5 | |

FIGURE 34 (CONT.)

| | | | | | | |
|---|---|---|---|---|---|---|
| 83 | | eIF3M | | | eIF5 | eIF6 |
| 84 | | eIF3M | | eIF4H | | |
| 85 | | eIF3M | | eIF4H | | eIF6 |
| 86 | | eIF3M | | eIF4H | eIF5 | |
| 87 | | eIF3M | | eIF4H | eIF5 | eIF6 |
| 88 | | eIF3M | eIF4A | | | |
| 89 | | eIF3M | eIF4A | | | eIF6 |
| 90 | | eIF3M | eIF4A | | eIF5 | |
| 91 | | eIF3M | eIF4A | | eIF5 | eIF6 |
| 92 | | eIF3M | eIF4A | eIF4H | | |
| 93 | | eIF3M | eIF4A | eIF4H | | eIF6 |
| 94 | | eIF3M | eIF4A | eIF4H | eIF5 | |
| 95 | | eIF3M | eIF4A | eIF4H | eIF5 | eIF6 |
| 96 | eIF3I | | | | | |
| 97 | eIF3I | | | | | eIF6 |
| 98 | eIF3I | | | | eIF5 | |
| 99 | eIF3I | | | | eIF5 | eIF6 |
| 100 | eIF3I | | | eIF4H | | |
| 101 | eIF3I | | | eIF4H | | eIF6 |
| 102 | eIF3I | | | eIF4H | eIF5 | |
| 103 | eIF3I | | | eIF4H | eIF5 | eIF6 |
| 104 | eIF3I | | eIF4A | | | |
| 105 | eIF3I | | eIF4A | | | eIF6 |
| 106 | eIF3I | | eIF4A | | eIF5 | |
| 107 | eIF3I | | eIF4A | | eIF5 | eIF6 |
| 108 | eIF3I | | eIF4A | eIF4H | | |
| 109 | eIF3I | | eIF4A | eIF4H | | eIF6 |
| 110 | eIF3I | | eIF4A | eIF4H | eIF5 | |
| 111 | eIF3I | | eIF4A | eIF4H | eIF5 | eIF6 |
| 112 | eIF3I | eIF3M | | | | |
| 113 | eIF3I | eIF3M | | | | eIF6 |
| 114 | eIF3I | eIF3M | | | eIF5 | |
| 115 | eIF3I | eIF3M | | | eIF5 | eIF6 |
| 116 | eIF3I | eIF3M | | eIF4H | | |
| 117 | eIF3I | eIF3M | | eIF4H | | eIF6 |
| 118 | eIF3I | eIF3M | | eIF4H | eIF5 | |
| 119 | eIF3I | eIF3M | | eIF4H | eIF5 | eIF6 |
| 120 | eIF3I | eIF3M | eIF4A | | | |
| 121 | eIF3I | eIF3M | eIF4A | | | eIF6 |
| 122 | eIF3I | eIF3M | eIF4A | | eIF5 | |
| 123 | eIF3I | eIF3M | eIF4A | | eIF5 | eIF6 |
| 124 | eIF3I | eIF3M | eIF4A | eIF4H | | |
| 125 | eIF3I | eIF3M | eIF4A | eIF4H | | eIF6 |
| 126 | eIF3I | eIF3M | eIF4A | eIF4H | eIF5 | |
| 127 | eIF3I | eIF3M | eIF4A | eIF4H | eIF5 | eIF6 |

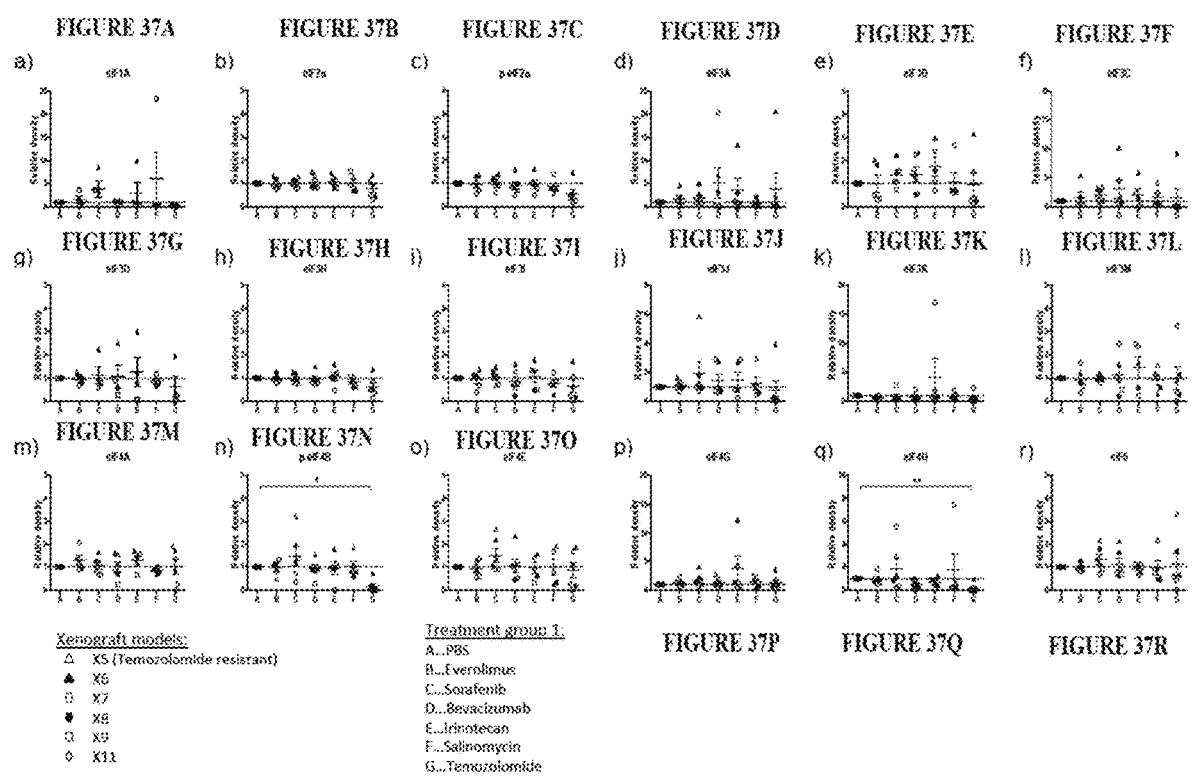

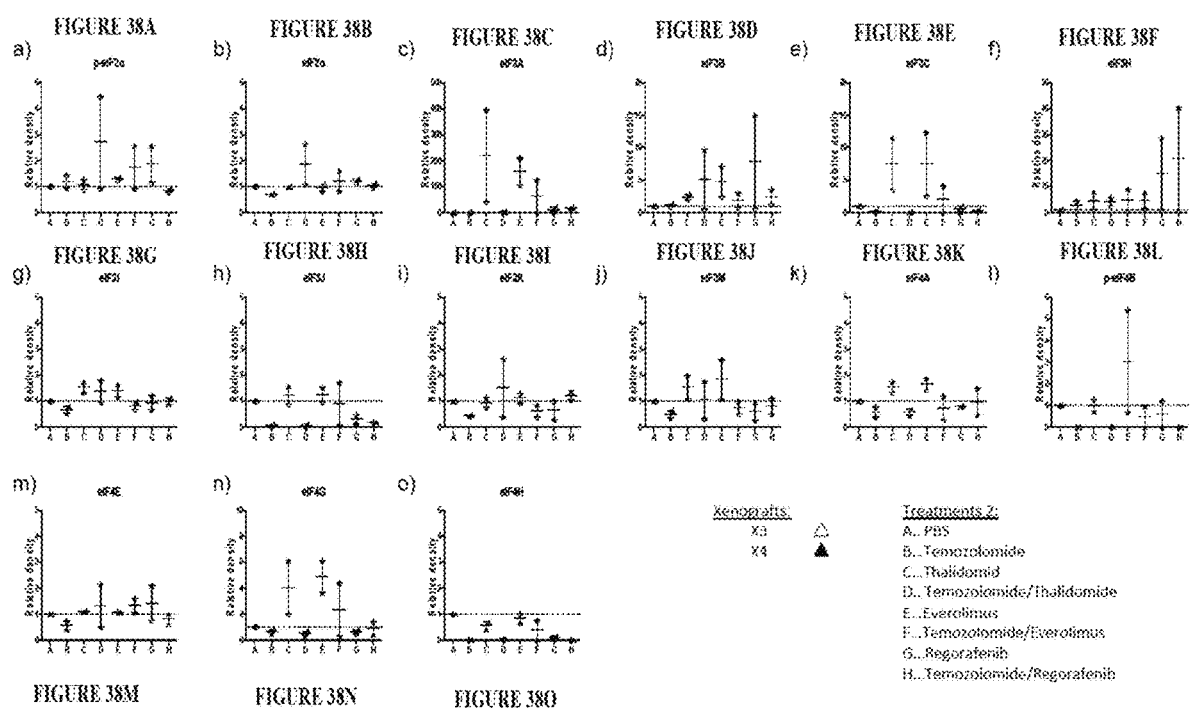

```
SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: siRNA molecule

<400> SEQUENCE: 1
gaccagacat atcctagcta a                                            21

<210> SEQ ID NO 2
<211> LENGTH: 21
<212> TYPE: DNA
<213> ORGANISM: Artificial Sequence
<220> FEATURE:
<223> OTHER INFORMATION: siRNA molecule

<400> SEQUENCE: 2
aagcaatacc gtcatgtttc a                                            21

<210> SEQ ID NO 3
<211> LENGTH: 21
<212> TYPE: DNA
<213> ORGANISM: Artificial Sequence
<220> FEATURE:
<223> OTHER INFORMATION: siRNA molecule

<400> SEQUENCE: 3
aggcgcttaa tcggcctcca a                                            21
```

```
<210> SEQ ID NO 4
<211> LENGTH: 21
<212> TYPE: DNA
<213> ORGANISM: Artificial Sequence
<220> FEATURE:
<223> OTHER INFORMATION: siRNA molecule

<400> SEQUENCE: 4
cagccagaag tgcaacatgt a                                                 21

<210> SEQ ID NO 5
<211> LENGTH: 21
<212> TYPE: DNA
<213> ORGANISM: Artificial Sequence
<220> FEATURE:
<223> OTHER INFORMATION: siRNA molecule

<400> SEQUENCE: 5
ctgctttgcc aagctcacca a                                                 21

<210> SEQ ID NO 6
<211> LENGTH: 21
<212> TYPE: DNA
<213> ORGANISM: Artificial Sequence
<220> FEATURE:
<223> OTHER INFORMATION: siRNA molecule

<400> SEQUENCE: 6
ctggtgcatc ccaagacttc a                                                 21

<210> SEQ ID NO 7
<211> LENGTH: 21
<212> TYPE: DNA
<213> ORGANISM: Artificial Sequence
<220> FEATURE:
<223> OTHER INFORMATION: siRNA molecule

<400> SEQUENCE: 7
ataaattggt ttggtaataa a                                                 21

<210> SEQ ID NO 8
<211> LENGTH: 21
<212> TYPE: DNA
<213> ORGANISM: Artificial Sequence
<220> FEATURE:
<223> OTHER INFORMATION: siRNA molecule

<400> SEQUENCE: 8
aaggacccta tcgtcaatgt a                                                 21

<210> SEQ ID NO 9
<211> LENGTH: 21
<212> TYPE: DNA
<213> ORGANISM: Artificial Sequence
<220> FEATURE:
<223> OTHER INFORMATION: siRNA molecule

<400> SEQUENCE: 9
ccgagactac caggataaca a                                                 21

<210> SEQ ID NO 10
<211> LENGTH: 21
<212> TYPE: DNA
<213> ORGANISM: Artificial Sequence
<220> FEATURE:
<223> OTHER INFORMATION: siRNA molecule
```

```
<400> SEQUENCE: 10
atcaatgaaa ctgatacatt t                                    21
```

ANTITUMOR COMPOUNDS AND TUMOR DIAGNOSIS

CROSS REFERENCE TO RELATED APPLICATIONS

This application is a U.S. National Stage Application of PCT/EP2017/069053, international filing date Jul. 27, 2017, which claims priority to EP17166262.0 filed Apr. 12, 2017 and EP 16182554.2, filed Aug. 3, 2016, the disclosures of which are incorporated herein by reference.

REFERENCE TO SUBMISSION OF A SEQUENCE LISTING AS A TEXT FILE

The Sequence Listing written in file 095697-1122930_SEQ_Listing.txt created on Jan. 31, 2019, 4,096 bytes, machine format IBM-PC, MS-Windows operating system, is hereby incorporated by reference in its entirety for all purposes.

The present invention is in the field of tumor treatment and relates to compounds to be used in the treatment of tumors. Further, the present invention relates to a method of diagnosing lung cancer in an individual and to a method of providing a prognosis to an individual suffering from lung cancer. Furthermore, the present invention relates to a method of diagnosing colorectal cancer in an individual, a method of differentiating between colon cancer (CC) and rectum cancer (RC) in an individual, a method of determining whether an individual responds to a therapeutic treatment of colorectal cancer, and to a method of determining the course of colorectal cancer in an individual. Furthermore, the present invention relates to a method of diagnosing a glioma in an individual, a method of grading a glioma in an individual, a method of differentiating between a low-grade glioma and a high-grade glioma in an individual, a method of determining whether an individual responds to a therapeutic treatment of a glioma, and a method of determining the course of a glioma in an individual. In addition, the present invention relates to a kit for conducting the above mentioned methods.

BACKGROUND OF THE INVENTION

Cancer is a leading cause of death worldwide. In 2012 14.1 million new cases and 8.2 million deaths have been reported. It is expected that by 2030, the number of people being diagnosed with cancer increases to 21 million, and deaths from cancer worldwide are projected to continue to rise, with an estimated 13.1 million deaths in 2030 globally. Despite recent advances in the understanding of the genesis, progression and treatment of cancer, lots of further investigations need to be done to improve the overall prognosis of cancer patients.

In most cases, tumors are currently treated by using chemotherapeutics, antibodies and further substance classes. In addition, solid tumors are regularly treated using surgical methods. Typically the surgical removal of the tumor along with removal of healthy tissue surrounding the main tumor mass is the first step in the treatment of solid tumors. Thereafter, chemotherapeutics are administered in order to kill remaining tumor cells and to prevent that these tumor cells migrate within the body. It is known that chemotherapeutics have different mechanisms of action and, thus, may be used only for specific tumor types and/or may cause various side effects.

Proteins are crucial for the survival of every cell. They are synthesized from the genetic code (delivered in form of mRNA) by ribosomes, a process termed translation. Eukaryotic translation Initiation factors (eIFs) are necessary for the first steps of the translation process, including especially the loading of the ribosome onto the mRNA by stabilizing the formation of the functional ribosome around the start codon. Furthermore, eIFs provide also regulatory mechanisms in translation initiation.

In a cellular context eIF action is partly regulated by the mTOR-pathway, which incorporates both extracellular and intracellular signaling molecules and is a central regulator of cell metabolism, growth, proliferation and survival.

Tumor cells may show an eIF expression pattern which is different from that of healthy cells. Even between the various types of tumors, eIF expression may vary. In tumor cells some eIFs are upregulated whereas some other eIFs are downregulated. Thus, eIFs may be used as tumor markers.

It is an object of the present invention to provide anew approach to treat tumors using eIFs as targets. The present inventors identified eIF modulating compounds which can be used in the treatment of a tumor.

In addition, new and reliable eIF tumor markers are (still) needed. Comprehensive studies analyzing the relationship between the whole range of eIFs and patient outcome and analyzing the potential of the whole range of eIFs as markers allowing the diagnosis of tumors, differential diagnosis between specific tumor entities, tumor monitoring or treatment monitoring have not been performed yet. The present inventors have carried out theses analysis and identified eIFs which performed best in the prognosis of an individual suffering from a tumor, in the diagnosis of a tumor, in the differential diagnosis between specific tumor identities, in the monitoring of the course of a tumor disease, or in the determination of a treatment response. The identified eIFs allow a reliable prognosis with respect to the life expectancy of an individual suffering from a tumor, tumor diagnosis in an individual, differential diagnosis between specific tumor entities in an individual, monitoring of the course of a tumor disease in an individual, or determination of a treatment response in an individual.

SUMMARY OF THE INVENTION

In a first aspect, the present invention relates to a eukaryotic initiation factor (eIF) modulating compound for use in the treatment of a tumor.

In a second aspect, the present invention relates to a composition comprising at least one compound according to the first aspect of the present invention for use in the treatment of a tumor.

In a third aspect, the present invention relates to a method of diagnosing lung cancer in an individual (suspected of having lung cancer) comprising the step of:
  determining the level of at least one eukaryotic Initiation Factor (eIF) in a sample from an individual,
  wherein the at least one eIF is selected from the group consisting of eIF1A and eIF6.

In a fourth aspect, the present invention relates to a method of providing a prognosis to an individual suffering from lung cancer comprising the step of:
  determining the level of eIF6 in a sample from an individual suffering from lung cancer.

In a fifth aspect, the present invention relates to a method of diagnosing colorectal cancer in an individual (suspected of having colorectal cancer) comprising the step of:

determining the level of at least one eukaryotic Initiation Factor (eIF) in a sample from an individual, wherein the at least one eIF is selected from the group consisting of eIF1, eIF5, and eIF6.

In a sixth aspect, the present invention relates to a method of differentiating between colon cancer (CC) and rectum cancer (RC) in an individual comprising the step of:
determining the level of at least one eukaryotic Initiation Factor (eIF) in a sample from an individual, wherein the at least one eIF is selected from the group consisting of eIF1, eIF5, and eIF6.

In a seventh aspect, the present invention relates to a method of determining whether an individual (suffering from colorectal cancer) responds to a therapeutic treatment of colorectal cancer comprising the step of:
determining the level of at least one eukaryotic Initiation Factor (eIF) in a sample from an individual, wherein the at least one eIF is selected from the group consisting of eIF1, eIF5, and eIF6.

In an eight aspect, the present invention relates to a method of determining the course of colorectal cancer in an individual (suffering from colorectal cancer) comprising the step of: determining the level of at least one eukaryotic Initiation Factor (eIF) in a sample from an individual, wherein the at least one eIF is selected from the group consisting of eIF1, eIF5, and eIF6.

In a ninth aspect, the present invention relates to a method of diagnosing a glioma in an individual (suspected of suffering from a glioma) comprising the step of:
determining the level of at least one eukaryotic Initiation Factor (eIF) in a sample from an individual, wherein the at least one eIF is selected from the group consisting of eIF3I, eIF3M, eIF4A, eIF4H, eIF5, and eIF6.

In a tenth aspect, the present invention relates to a method of grading a glioma in an individual (suffering from a glioma) comprising the step of:
determining the level of at least one eukaryotic Initiation Factor (eIF) in a sample from an individual, wherein the at least one eIF is selected from the group consisting of eIF3I, eIF4A, eIF4H, and eIF6.

In an eleventh aspect, the present invention relates to a method of differentiating between a low-grade (benign) glioma and a high-grade (malignant) glioma in an individual comprising the step of:
determining the level of at least one eukaryotic Initiation Factor (eIF) in a sample from an individual, wherein the at least one eIF is selected from the group consisting of eIF3I, eIF4H, eIF5, and eIF6.

In a twelfth aspect, the present invention relates to a method of providing a prognosis to an individual suffering from a glioma comprising the step of:
determining the level of at least one eukaryotic Initiation Factor (eIF) in a sample from an individual suffering from a glioma, wherein the at least one eIF is selected from the group consisting of eIF3I, eIF4G, and eIF4H.

In a thirteenth aspect, the present invention relates to a method of determining whether an individual (suffering from a glioma) responds to a therapeutic treatment of a glioma comprising the step of:
determining the level of at least one eukaryotic Initiation Factor (eIF) in a sample from an individual, wherein the at least one eIF is selected from the group consisting of eIF3D, eIF3H, eIF3I, eIF3J, eIF3K, eIF3M, eIF4A, eIF4B, preferably peIF4B, eIF4E, eIF4H, and eIF6.

In a fourteenth aspect, the present invention relates to a method of determining the course of a glioma in an individual (suffering from a glioma) comprising the step of:
determining the level of at least one eukaryotic Initiation Factor (eIF) in a sample from an individual,
wherein the at least one eIF is selected from the group consisting of eIF2α, preferably peIF2α, eIF3D, eIF3H, eIF3I, eIF3J, eIF3K, eIF3M, eIF4A, eIF4B, preferably peIF4B, eIF4E, eIF4H, and eIF6.

In a fifteenth aspect, the present invention relates to a kit comprising means for determining the level of at least one eIF in a sample from an individual, wherein the at least one eIF is selected from the group consisting of.
(i) eIF1A and eIF6,
(ii) eIF6,
(iii) eIF1, eIF5, and eIF6,
(iv) eIF3I, eIF3M, eIF4A, eIF4H, eIF5, and eIF6,
(v) eIF3I, eIF4A, eIF4H, and eIF6,
(vi) eIF3I, eIF4H, eIF5, and eIF6,
(vii) eIF3I, eIF4G, and eIF4H,
(viii) eIF3D, eIF3H, eIF3I, eIF3J, eIF3K, eIF3M, eIF4A, eIF4B, preferably peIF4B, eIF4E, eIF4H, and eIF6, and/or
(ix) eIF2α, preferably peIF2α, eIF3D, eIF3H, eIF3I, eIF3J, eIF3K, eIF3M, eIF4A, eIF4B, preferably peIF4B, eIF4E, eIF4H, and eIF6.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

The terms "a" and "an" and "the" and similar reference used in the context of describing the invention (especially in the context of the claims) are to be construed to cover both the singular and the plural, unless otherwise indicated herein or clearly contradicted by context.

The term "eukaryotic Initiation Factor (eIF)", as used herein, refers to molecules which are involved in the initiation phase of eukaryotic translation. These factors help to stabilize the formation of the functional ribosome around the start codon and also provide regulatory mechanisms in translation initiation. The term "eukaryotic Initiation Factor (eIF)", as used herein, covers eIF RNA transcripts (RNA tran-script variants) such as mRNAs including splice variants of these transcripts and eIF proteins encoded thereby. Thus, the level of the eIFs may be determined by measuring mRNA or protein levels. The term "eukaryotic Initiation Factor (eIF)", as used herein, also covers eIF isoforms. These eIF isoforms are members of a set of highly similar molecules, in particular proteins, that perform the same or similar biological role. eIF4A, for example, comprises the isoforms eIF4A1, eIF4A2, and/or eIF4A3, encoded by the respective genes. Further, eIF4E, for example, comprises the isoforms eIF4E1, eIF4E2, and/or eIF4E3, encoded by the respective genes. Furthermore, eIF4G, for example, comprises the isoforms eIF4G1, eIF4G2, and/or eIF4G3, encoded by the respective genes. In addition, eIF5A, for example, comprises the isoforms eIF5A1 and/or eIF5A2, encoded by the respective genes. The level of eIF isoforms may also be determined by measuring mRNA or protein levels.

A "eukaryotic initiation factor (eIF) modulating compound", as used herein, refers to a compound which is able to modulate/influence directly or indirectly the level of at least one eIF in a mammal, in particular in a human individual. Once administered to a mammal the level of at least one eIF within mammals increases or decreases.

The term "eIF binding molecule", as used herein, refers to a molecule which is able to bind an eIF. eIF binding molecules are preferably polypeptides. The term "eIF binding polypeptide", as used herein, refers to a polypeptide that comprises an "eIF binding site" which is able to bind to an eIF. Such binding can be determined by using an immunoassay such as enzyme-linked immunosorbent assay (ELISA), for instance. The eIF binding site may comprise, for instance, one or more CDRs of an antibody and is capable of binding an eIF.

The term "siRNA", as used herein, refers to typically double stranded RNA molecules (dsRNA) that mediate the targeted cleavage of a RNA transcript via a RNA-induced silencing complex (RISC) pathway. siRNA molecules interfere with the expression of specific genes with complementary nucleotide sequences by degrading mRNA after transcription.

A "double stranded RNA" or "dsRNA", as used herein, refers to an RNA molecule or complex of molecules having a hybridized duplex region that comprises two anti-parallel and substantially complementary nucleic acid strands, which will be referred to as having "sense" and "antisense" orientations with respect to a target RNA encoding an eIF. The target sequence will preferably be from 9-36 nucleotides in length, including all sub-ranges in between.

"Identity" or "sequence identity", as used herein, is calculated by comparing a nucleic or amino acid sequence to another sequence using a specific algorithm. A preferred tool is "BLAST" using the standard parameters (Altschul et al., J. Mol. Biol. 215:403-410 (1990); Altschul et al., Nucleic Acids Res. 25:3389-3402 (1997) (http://blast.ncbi.nlm.nih.gov/).

The term "antibody fragment", as used herein, refers to a polypeptide that includes at least one immunoglobulin variable domain or immunoglobulin variable domain sequence and which specifically binds a specific antigen. An antibody fragment can comprise an antibody or a polypeptide comprising an antigen-binding domain of an antibody. An antibody fragment can comprise a monoclonal antibody or a polypeptide comprising an antigen-binding domain of a monoclonal antibody. For example, an antibody can include a heavy (H) chain variable region and a light (L) chain variable region. An antibody may include two heavy (H) chain variable regions and two light (L) chain variable regions. The term "antibody fragment" encompasses antigen-binding fragments of antibodies such as single chain antibodies, Fab fragments, $F(ab')_2$, Fv fragments and scFv. An antibody can have the structural features of IgA, IgG, IgE, IgD, IgM (as well as subtypes and combinations thereof). Antibodies can be from any source, including mouse, rabbit, pig, rat, and primate (human and non-human primate), whereby the antibodies have to be humanized before administered to a patient. Methods to humanize antibodies are well known in the art.

The term "antibody variable domain", as used herein, refers to the portions of the light and heavy chains of antibodies that include amino acid sequences of complementarity determining regions (CDRs; i.e., CDR1, CDR2, and CDR3), and framework regions (FRs).

The term "lung cancer", as used herein, refers to a malignant lung tumor characterized by uncontrolled cell growth in tissues of the lung. If left untreated, this growth can spread beyond the lung by the process of metastasis into nearby issue or other parts of the body. Most cancers that start in the lung, known as primary lung cancers, are carcinomas. The two main types are small-cell lung carcinoma (SCLC) and non-small-cell lung carcinoma (NSCLC).

The term "small-cell lung carcinoma (SCLC)", as used herein, refers to a disease where the cells contain dense neurosecretory granules (vesicles containing neuroendocrine hormones), which give this tumor an endocrine/paraneoplastic syndrome association. Most cases arise in the larger airways (primary and secondary bronchi). Sixty to seventy percent have extensive disease (which cannot be targeted within a single radiation therapy field) at presentation.

The term "non-small-cell lung carcinoma (NSCLC)", as used herein, refers to any type of epithelial lung cancer other than small cell lung carcinoma (SCLC). NSCLC accounts for about 85% of all lung cancers. As a class, NSCLCs are relatively insensitive to chemotherapy, compared to small cell carcinoma. When possible, they are primarily treated by surgical resection with curative intent, although chemotherapy is increasingly being used both pre-operatively (neoadjuvant chemotherapy) and post-operatively (adjuvant chemotherapy). The most common types of NSCLC are squamous cell carcinoma (SQCC), large cell carcinoma, and adenocarcinoma (ADC).

The term "diagnosing lung cancer", as used herein, means determining whether an individual shows signs of or suffers from lung cancer.

The term "colorectal cancer (or colorectal carcinoma)", as used herein, refers to cancer (or carcinoma) in the colon, rectum (parts of the large intestine), and/or appendix. The term "colorectal carcinoma", as used herein, also relates to a disease in which a group of cells display uncontrolled growth (division beyond the normal limits), invasion (intrusion on and destruction of adjacent tissues), and sometimes metastasis (spread to other locations in the body via lymph or blood). These three malignant properties differentiate the colorectal carcinoma from a benign/non-malignant tumor, which is self-limited and does not invade and/or metastasize. The colorectal cancer may be colon cancer (CC) or rectum cancer (RC).

The colorectal cancer (or carcinoma) may be classified according to the Dukes classification system which classifies the cancer into Dukes stages "A", "B", "C", and "D" (see Dukes C E, "The classification of cancer of the rectum", Journal of Pathological Bacteriology, 1932, 35:323). The colorectal cancer (or carcinoma may) also be staged according to the more detailed and most common Tumor, Node, and Metastasis (TNM) staging system from the American Joint Committee on Cancer (AJCC) (see AJCC Cancer Staging Manual, sixth edition, Springer-Verlag New York, Inc. 2002). This staging system describes the size of a primary tumor (T), whether any lymph nodes contain cancer cells (N), and whether the cancer has spread to another part of the body (M). In particular, stage 0 relates to carcinoma in situ (e.g. intramucosal carcinoma, wherein malignant cells invade the mucosal lamina propria). The criteria for stages I, II, and III are larger tumor size and/or spread of the cancer beyond the organ in which it first developed to nearby lymph nodes and/or organs adjacent to the location of the primary tumor. The criteria for stage IV are that the cancer has spread to another organ(s).

The term "diagnosing colorectal cancer (or colorectal carcinoma)", as used herein, means determining whether an individual shows signs of or suffers from colorectal cancer (or colorectal carcinoma).

The term "differentiating between colon cancer (CC) and rectum cancer (RC)", as used herein, means differential diagnosing between said two conditions, namely colon cancer (CC) and rectum cancer (RC). Said differential diagnosing allows to decide whether an individual suffers from colon cancer (CC) or rectum cancer (RC).

The term "glioma", as used herein, refers to a type of tumor that starts in the brain or spine. It is called a glioma because it arises from glial cells. The most common site of gliomas is the brain. Gliomas make up about 30% of all brain and central nervous system tumors.

Gliomas may be classified by cell type and grade. In particular, gliomas may be named according to the specific type of cell with which they share histological features, but not necessarily from which they originate. The main types of gliomas are: ependymomas (ependymal cells), astrocytomas (astrocytes) (glioblastoma multiform is a malignant astrocytoma and the most common primary brain tumor among adults), oligodendrogliomas (oligodendrocytes), brainstem gliomas (develop in the brain stem), optic nerve gliomas (develop in or around the optic nerve), and mixed gliomas, such as oligoastrocytomas (contain cells from different types of glia). Preferably, the glioma is selected from the group consisting of an astrocytoma, ependymoma, oligodendrogliomas, and brainstem glioma.

Gliomas may be further categorized according to their grade, which is determined by pathologic evaluation of the tumor. Thus, gliomas may be classified as low-grad gliomas or high-grade gliomas. Low-grade gliomas (World Health Organization (WHO) grades I and II) are well-differentiated (not anaplastic). They tend to exhibit benign tendencies and portend a better prognosis for the individual. High-grade gliomas (WHO grades III and IV) are undifferentiated or anaplastic. They are malignant and carry a worse prognosis.

Thus, WHO grades I and II characterize a low-grade (benign) glioma and WHO grades III and IV characterize a high-grade (malignant) glioma. In particular, with respect to an astrocytoma, grade I refers to/means a pilozytic astrocytoma, grade II refers to/means a diffuse astrocytoma, grade III refers to/means an anaplastic astrocytoma, and grade IV refers to/means a glioblastoma multiform.

The term "diagnosing a glioma", as used herein, means determining whether an individual shows signs of or suffers from a glioma. The glioma may be an astrocytoma, ependymoma, oligodendrogliomas, and brainstem glioma.

The term "grading a glioma", as used herein, means determining which glioma grade is present in the individual. In particular, with grading it is determined, whether the individual suffers from a glioma of grade I, grade II, grade III, or grade IV. As mentioned above, with respect to an astrocytoma, grade I refers to/means a pilozytic astrocytoma, grade II refers to/means a diffuse astrocytoma, grade III refers to/means an anaplastic astrocytoma, and grade IV refers to/means a glioblastoma multiform.

The term "differentiating between a low-grade (benign) and high-grade (malignant) glioma", as used herein, means differential diagnosing between said two conditions, namely a low-grade (benign) glioma and high-grade (malignant) glioma. Said differential diagnosing allows to decide whether an individual suffers from a low-grade (benign) glioma or high-grade (malignant) glioma.

The term "providing a prognosis to an individual suffering from a tumor", as used herein, particularly means determining whether the individual has a good prognosis or poor prognosis. The tumor may be lung cancer or a glioma. An individual suffering from a tumor may be considered to have a "good prognosis" where, for example, the survival rate associated with the tumor is greater compared to the survival rate of other individuals suffering from the same tumor or a related tumor subtype and showing another expression pattern of one or more of the prognostic markers of the present invention. In certain embodiments, a "good prognosis" indicates at least an increased expected survival time. A "good prognosis" indicates a greater than 1%, preferably greater than 10%, more preferably greater than 20%, more preferably greater than 30%, more preferably greater than 40%, more preferably greater than 50%, more preferably greater than 60%, more preferably greater than 70%, more preferably greater than 80%, more preferably greater than 90%, chance that the individual will survive to a specified time point (such as one, two, three, four, five, six or twelve months or even one, two or three years).

An individual suffering from a tumor may be considered to have a "poor prognosis" where, for example, the survival rate associated with the tumor is less compared to the survival rate of other individuals suffering from the same tumor or a related tumor subtype and showing another expression pattern of one or more of the prognostic markers of the present invention. A "poor prognosis" indicates a greater than 1%, preferably greater than 10%, more preferably greater than 20%, more preferably greater than 30%, more preferably greater than 40%, more preferably greater than 50%, more preferably greater than 60%, more preferably greater than 70%, more preferably greater than 80%, more preferably greater than 90%, chance that the individual will not survive to a specified time point (such as one, two, three, four, five, six or twelve months or even one, two or three years). This may include also a greater than 50%, preferably greater than 60%, more preferably greater than 70%, more preferably greater than 80%, more preferably greater than 90% chance that the tumor will metastasize or migrate.

The term "treatment", in particular "therapeutic treatment", as used herein, refers to any therapy which improves the health status and/or prolongs (increases) the lifespan of an individual suffering from a disease or condition, in particular a tumor. Said therapy may eliminate the disease or condition in an individual, arrest or slow the development of a disease in an individual, inhibit or slow the development of a disease in an individual, decrease the frequency or severity of symptoms in an individual, and/or decrease the recurrence in an individual who currently has or who previously has had a disease. The treatment of the diseases or conditions described herein includes, but is not limited to, administration of a drug, surgery, chemotherapy, and/or radiotherapy.

The term "individual", as used herein, refers to any subject for whom it is desired to know whether she or he suffers from a disease or condition (e.g. lung cancer, colorectal cancer, or glioma). In particular, the term "individual", as used herein, refers to a subject suspected to be affected by the disease or condition (e.g. lung cancer, colorectal cancer, or glioma). The individual may be diagnosed to be affected by the disease or condition (e.g. lung cancer, colorectal cancer, or glioma), i.e. diseased, or may be diagnosed to be not affected by the disease or condition (e.g. lung cancer, colorectal cancer, or glioma), i.e. healthy. The term "individual", as used herein, also refers to a subject which is affected by the disease or condition (e.g. lung cancer, colorectal cancer, or glioma), i.e. diseased. The patient may be retested for the disease or condition (e.g. lung cancer, colorectal cancer, or glioma) and may be diagnosed to be still affected by the disease or condition (e.g. lung cancer, colorectal cancer, or glioma), i.e. diseased, or not affected by the disease or condition (e.g. lung cancer, colorectal cancer, or glioma) anymore, i.e. healthy, for example after therapeutic intervention. The individual may also be retested for the disease or condition (e.g. lung cancer, colorectal cancer, or glioma) and may be diagnosed as having developed an advanced form of the disease or condition (e.g. lung cancer, colorectal cancer, or glioma).

It should be noted that an individual that is diagnosed as being healthy, i.e. not suffering from the disease or condition in question (e.g. lung cancer, colorectal cancer, or glioma), may possibly suffer from another disease or condition not tested/known.

The term "individual", as used herein, further refers to any subject suffering from a disease or condition, in particular a tumor (e.g. lung cancer or glioma), for whom it is desired to know whether she or he has a good prognosis with respect to the disease or condition, in particular the tumor (e.g. lung cancer or glioma), or poor prognosis with respect to the disease or condition, in particular the tumor (e.g. lung cancer or glioma).

The individual may be any mammal, including both a human and another mammal, e.g. an animal such as a rabbit, mouse, rat, or monkey. Human individuals are particularly preferred.

The term "(control) patient", as used herein, refers to a subject known to be affected by a disease or condition (e.g. lung cancer, colorectal cancer, or glioma), i.e. diseased. Said (control) patient may have developed an advanced form of the disease or condition (e.g. lung cancer, colorectal cancer, or glioma). For example, the (control) patient is a (control) patient with lung cancer, colorectal cancer (e.g. colon cancer (CC) or rectum cancer (RC)) or glioma (e.g. low-grade (benign) glioma or high-grade (malignant) glioma, or glioma of grades I, II, III or IV).

The "(control) patient", as used herein, also refers to a patient suffering from the same tumor (e.g. lung cancer or glioma) as the individual to be tested, in particular in cases where a prognosis of the individual suffering from the tumor (e.g. lung cancer or glioma) is determined.

The (control) patient may be any mammal, including both a human and another mammal, e.g. an animal such as a rabbit, mouse, rat, or monkey. Human (control) patients are particularly preferred.

The term "healthy (control) individual", as used herein, refers to a subject known to be not affected by the disease or condition (e.g. lung cancer, colorectal cancer, or glioma) (negative control), i.e. healthy.

The healthy individual, as used herein, also refers to a subject known to be not affected by a tumor (e.g. lung cancer or glioma).

It should be noted that an individual which is known to be healthy, i.e. not suffering from the disease or condition in question (e.g. lung cancer, colorectal cancer, or glioma), may possibly suffer from another disease or condition not tested/known. In addition, an individual which is known to be healthy, i.e. not suffering from the tumor in question (e.g. lung cancer or glioma), may possibly suffer from another tumor not tested/known.

The healthy individual may be any mammal, including both a human and another mammal, e.g. an animal such as a rabbit, mouse, rat, or monkey. Human healthy individuals are particularly preferred.

The term "level", as used herein, refers to an amount (measured for example in grams, mole, or ion counts) or concentration (e.g. absolute or relative concentration) of the at least one eIF claimed herein.

The term "level", as used herein, also comprises scaled, normalized, or scaled and normalized amounts or values. The level may also be a cut-off level.

In a preferred embodiment, the level is an expression level.

The term "sample", as used herein, refers to any sample from an individual or (control) patient containing at least one of the eIFs claimed herein. Preferably, the sample is a biological sample. The biological sample may be a body fluid sample. For example, biological samples encompassed by the present invention are blood (e.g. whole blood or blood fraction such as blood cell fraction, serum or plasma) samples, lymph samples, saliva samples, urine samples, or samples from other peripheral sources. Said biological samples may be mixed or pooled, e.g. a sample may be a mixture of a blood sample and a urine sample. Said biological samples may be provided by removing a body fluid from an individual or control (patient), but may also be provided by using a previously isolated sample. For example, a blood sample may be taken from an individual or (control) patient by conventional blood collection techniques. The biological sample, e.g. urine sample or blood sample, may be obtained from an individual or (control) patient prior to the initiation of a therapeutic treatment, during the therapeutic treatment, and/or after the therapeutic treatment. If the sample, in particular the biological sample, is obtained from at least one (control) patient or healthy (control) individual, e.g. from at least 1, 2, 3, 4, 5, 6, 7, 8, 9, 10, 20, 30, 40, 50, 60, 70, 80, 90, 100, 150, 200, 250, 300, 400, 500, or 1.000 (control) patient(s) or healthy (control) individual(s), it is designated as a "reference sample", in particular as a "reference biological sample". Preferably, the reference (biological) sample is from the same source than the (biological) sample of the individual to be tested, e.g. both are blood samples or urine samples. It is further preferred that both are from the same species, e.g. from a human. It is also (alternatively or additionally) preferred that the measurements of the reference (biological) sample and the (biological) sample of the individual to be tested are identical, e.g. both have an identical volume. It is particularly preferred that the reference (biological) sample and the (biological) sample are from individuals/(control) patients of the same sex and similar age, e.g. no more than 2 years apart from each other.

The term "body fluid sample", as used herein, refers to any liquid sample derived from the body of an individual or (control) patient containing at least one of the eIFs claimed herein.

Said body fluid sample may be a urine sample, blood sample, sputum sample, breast milk sample, cerebrospinal fluid (CSF) sample, cerumen (earwax) sample, gastric juice sample, mucus sample, lymph sample, endolymph fluid sample, perilymph fluid sample, peritoneal fluid sample, pleural fluid sample, saliva sample, sebum (skin oil) sample, semen sample, sweat sample, tears sample, cheek swab, vaginal secretion sample, liquid biopsy, or vomit sample including components or fractions thereof. The term "body fluid sample" also encompasses body fluid fractions, e.g. blood fractions, urine fractions or sputum fractions. The body fluid samples may be mixed or pooled. Thus, a body fluid sample may be a mixture of a blood and a urine sample or a mixture of a blood and cerebrospinal fluid sample. Said body fluid sample may be provided by removing a body liquid from an individual or (control) patient, but may also be provided by using previously isolated body fluid sample material. The body fluid sample allows for a non-invasive analysis of an individual. It is further preferred that the body fluid sample has a volume of between 0.01 and 20 ml, more preferably of between 0.1 and 10 ml, even more preferably of between 0.5 and 8 ml, and most preferably of between 1 and 5 ml. If the body fluid sample is obtained from at least one (control) patient or healthy (control) individual, e.g. from at least 1, 2, 3, 4, 5, 6, 7, 8, 9, 10, 20, 30, 40, 50, 60, 70, 80, 90, 100, 150, 200, 250, 300, 400, 500, or 1.000 (control) patients (s) or healthy (control) individual(s), it is designated as a "reference body fluid sample".

The term "blood sample", as used herein, encompasses a whole blood sample or a blood fraction sample such as a blood cell fraction, blood serum, or blood plasma sample. It is preferred that the blood serum or plasma sample has a volume of between 0.01 and 20 ml, more preferably of between 0.1 and 10 ml, even more preferably of between 0.5 and 8 ml and most preferably of between 1 and 5 ml.

In the context of the present invention, the term "kit of parts (in short: kit)" is understood to be any combination of at least some of the components identified herein, which are combined, coexisting spatially, to a functional unit, and which can contain further components. Said kit may allow point-of-care testing (POCT).

The term "point-of-care testing (POCT)", as used herein, refers to a medical diagnostic testing at or near the point of care that is the time and place of individual care. This contrasts with the historical pattern in which testing was wholly or mostly confined to the medical laboratory, which entailed sending off specimens away from the point of care and then waiting hours or days to learn the results, during which time care must continue without the desired information. Point-of-care tests are simple medical tests that can be performed at the bedside. The driving notion behind POCT is to bring the test conveniently and immediately to the individual to be tested. This increases the likelihood that the individual, physician, and care team will receive the results quicker, which allows for immediate clinical management decisions to be made. POCT is often accomplished through the use of transportable, portable, and handheld instruments and test kits. Small bench analyzers or fixed equipment can also be used when a handheld device is not available—the goal is to collect the specimen and obtain the results in a very short period of time at or near the location of the individual so that the treatment plan can be adjusted as necessary before the individual leaves the hospital.

Embodiments of the Invention

Protein translation can be divided into an initiation, elongation, termination and ribosome recycling step. Regulation of translation is mainly executed at the initiation step and dysregulation leads to abnormal gene expression which can result in cancer formation through uncontrolled cell growth in humans and mammals. The translation process is monitored by eukaryotic initiation factors (eIFs). All of them have different functions and roles in cell proliferation and can be linked to tumorigenesis. They may serve as tumor suppressors or promote carcinogenesis and tumor progression in different types of cancer.

Surprisingly, it turned out that the modulation of eIFs in individuals suffering from a tumor influences the progress of the disease. Therefore, eIF modulating substances can be used in the treatment of a tumor in mammals and humans. In some embodiments the eIF modulating compound results in stagnation of the disease and tumor growth. In other embodiments migration and/or the formation of metastases can be prevented or significantly reduced.

Thus, in a first aspect, the present invention relates to a eukaryotic initiation factor (eIF) modulating compound for use in the treatment of a tumor.

During treatment of patients suffering from cancer, the level of eIF can be increased or decreased by using respective compounds. According to a preferred embodiment, the eIF modulating compound is selected from the group consisting of an eIF and an eIF inhibiting molecule. The administration of an eIF to a mammal increases its level in said mammal. The administration of eIF inhibiting molecules either reduces the level of eIFs within the cells, in particular the tumor cells, or prevents that the eIFs fulfill their part during protein translation.

According to a preferred embodiment, the eIF inhibiting molecule is selected from the group consisting of an eIF binding molecule, a small interfering RNA (siRNA) and a short hairpin RNA (shRNA) for inhibiting expression of an eIF.

The eIF activity can be inhibited or significantly reduced by using eIF binding molecules. eIF binding molecules are able to bind to eIFs. Due to this binding, the biochemical and biological function of eIFs is inhibited or at least partially inhibited. The binding of such molecules to eIFs may also be used to mark specific eIFs to be removed by the immune system.

eIF binding molecules interact with the eIF polypeptide which is already expressed in tumor cells, for instance. In an alternative embodiment to modulate eIFs it is also possible to use compounds which can influence the expression rate of eIFs within cells. This can be achieved, for instance, by using RNA interference (RNAi) technology. RNA interference uses typically small interfering RNAs (siRNA) and/or short hairpin RNAs (shRNA). The administration of such molecules (e.g. siRNA, shRNA) leads to a decrease in expression of the target eIF gene. In some embodiments, eIF expression is decreased for an extended duration, e.g., at least one week, two weeks, three weeks, or four weeks or longer. For example, in certain instances, expression of the eIF gene is suppressed by at least about 5%, preferably at least 10%, more preferably at least 15%, more preferably at least 20%, more preferably at least 25%, more preferably at least 30%, more preferably at least 40%, more preferably at least 50%, more preferably at least 60%, more preferably at least 70%, more preferably at least 80%, more preferably at least 90%, by administration of the siRNA and/or shRNA molecules of the present invention.

The target sequence will preferably be from 9-36 nucleotides in length, including all sub-ranges in between. In a preferred embodiment, the length of the sense and antisense sequences that hybridize should each be at least 9, preferably at least, 15, more preferably at least 19, contiguous nucleotides, preferably at least 30 or 50 nucleotides, and more preferably at least 100, 200, 500 or 1000 nucleotides. The full-length sequence corresponding to the entire eIF gene transcript may also be used. The lengths are most preferably 100-2000 nucleotides. The degree of identity of the sense and antisense sequences to the targeted transcript should be at least 85%, preferably at least 90%, more preferably at least 95%, more preferably at least 98%, in particular 100%. The RNA molecule may of course comprise unrelated sequences which may function to stabilize the molecule.

Preferably, the target mRNA sequence commences with the dinucleotide AA, comprises a GC-content of about 30-70%, preferably 30-60%, more preferably 40-60%, more preferably about 45-55%, and does not have a high percentage identity to any nucleotide sequence other than the target in the genome of the cell in which it is to be introduced.

According to a preferred embodiment, the siRNA is at least about 15-50 nucleotides in length. Each complementary sequence of the double stranded siRNA is preferably about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length.

Other preferred RNA molecules to be used in RNA interference are so-called small hairpin RNAs (shRNAs) and comprise a hairpin structure (also called stem loop). In a preferred embodiment, shRNA comprises a short antisense strand, followed by a nucleotide loop of about 5 to about 9 nucleotides, and the analogous sense strand. Alternatively, the sense strand may precede the nucleotide loop structure and the antisense strand may follow. shRNAs, as used herein, may comprise about 19 to about 50 nucleotides, preferably about 19 to about 40 nucleotides, more preferably about 19 to about 30 nucleotides.

Specific RNA interference molecules, such as siRNA and shRNA molecules, can be easily designed by a person skilled in the art having regard to the sequence of the target gene.

According to a particularly preferred embodiment, specific RNA interference molecules may comprise or consist of the nucleic acid sequence GACCAGACATATCCTAGCTAA (SEQ ID No: 1) and/or AAGCAATACCGTCATGTTTCA (SEQ ID NO: 2) if the in vivo expression of eIF1 should be reduced, of the nucleic acid sequence AGGCGCTTAATCGGCCTCCAA (SEQ ID No: 3) and/or CAGCCAGAAGTGCAACATGTA (SEQ ID NO: 4) if the in vivo expression of eIF5 should be reduced, of the nucleic acid sequence CTGCTTTGCCAAGCTCACCAA (SEQ ID NO: 5) and/or CTGGTGCATCCCAAGACTTCA (SEQ ID NO: 6) if the in vivo expression of eIF6 should be reduced, of the nucleic acid sequence ATAAATTGGTTTGGTAATAAA (SEQ ID NO: 7) and/or AAGGACCCTATCGTCAATGTA (SEQ ID NO: 8) if the in vivo expression of eIF1AX should be reduced and of the nucleic acid sequence CCGAGACTACCAGGATAACAA (SEQ ID NO: 9) and/or ATCAATGAAACTGATACATTT (SEQ ID NO: 10) if the in vivo expression of eIF1AX should be reduced.

According to a preferred embodiment, the eIF binding molecule is a polypeptide or a peptide comprising at least one eIF binding site.

Polypeptides, peptides and proteins may be used as eIF binding molecules. They comprise at least one, preferably at least two, eIF binding sites. eIF binding sites in such molecules can be created, produced and identified by using random peptide libraries, for instance. Alternatively, if polypeptides, peptides and proteins are used which are derived from antibodies, methods known for producing eIF specific antibodies can be used.

According to a particularly preferred embodiment, the eIF binding molecule is an antibody or an antibody fragment binding to an eIF.

Particularly preferred antibody fragments, include Fab fragments, $F(ab')_2$ fragments, Fv fragments or a scFv.

In an alternative approach to increase the level of eIFs in an individual or in a mammal, the eIF modulating compound is a nucleic acid molecule encoding for eIFs. The administration of such a nucleic acid molecule is advantageous because it can be used to express one or more eIFs within the body.

The nucleic acid molecule is preferably a DNA or RNA molecule, wherein the DNA molecule is preferably comprised in an expression vector, preferably an expression plasmid. The expression vector of the present invention is preferably an expression vector for mammalian cells, which comprises a promoter operable in mammalian cells and further an origin of replication, a transcription initiation site, a protein coding site, a polyadenylation site, a transcription termination site, etc. Promoters which can be used for this purpose and which are operable in mammalian cells includes cytomegalovirus (CMV) promoter, thymidine kinase (TK) promoter of herpes simplex virus (HSV), SV40 promoter, etc.

According to a preferred embodiment, the eIF is selected from the group consisting of eIF1 (Gene: EIF1; Gene ID (GenBank): 10209), eIF1A (Gene: EIF1AX/EIF4C; Gene ID (GenBank): 1964), eIF2AK3/HsPEK (Gene: EIF2AK3; Gene ID (GenBank): 9451), eIF2AK4 (Gene: EIF2AK4, GCN2; Gene ID (GenBank): 440275), eIF2B4/eIF-2B subunit delta (Gene: EIF2B4; Gene ID (GenBank): 8890), eIF2C 3 (Gene: AGO3/EIF2C3; Gene ID (GenBank): 192669), eIF2d (Gene: EIF2D; Gene ID (GenBank): 1939), eIF-2A/alpha/α/eIF2S1 (Gene: EIF2S1; Gene ID (GenBank): 1965), eIF-2-beta/eIF2S2 (Gene: EIF2S2; Gene ID (GenBank): 8894), eIF3A (Gene:EIF3A; Gene ID (GenBank): 8661), eIF3B (Gene: EIF3B; Gene ID (GenBank): 8662), eIF3C (Gene: EIF3C; Gene ID (GenBank): 8663), eIF3D (Gene: EIF3D; Gene ID (GenBank): 8664) eIF3F (Gene: EIF3F; Gene ID (GenBank): 8665), eIF3G (Gene: EIF3G; Gene ID (GenBank): 8666), eIF3H (Gene: EIF3H/EIF3S3; Gene ID (GenBank): 8667), eIF3I (eIF3S2) (Gene: EIF3I/EIF3S2; Gene ID (GenBank): 8668), eIF3J (Gene: EIF3J/EIF3S1; Gene ID (GenBank):8669), eIF3K (Gene: EIF3K/EIF3S12; Gene ID (GenBank): 27335), eIF3L (Gene: EIF3L; Gene ID (GenBank): 51386), eIF3M (Gene: eIF3M; Gene ID (GenBank): 10480), eIF4A (eIF4A1, eIF4A2, eIF4A3, Gene: EIF4A1, Gene ID (GenBank): 1973, Gene: EIF4A2, Gene ID (GenBank): 1974, Gene: EIF4A3, Gene ID (GenBank): 9775), eIF4B (Gene: EIF4B; Gene ID (GenBank): 1975), eIF4E (eIF4E1, eIF4E2, eIF4E3, Gene: EIF4E1, Gene ID (GenBank): 1977, Gene: EIF4E2, Gene ID (GenBank):9470, Gene: EIF4E3; Gene ID (GenBank): 317649), 4E-BP (4E-BP1, 4EBP2, Gene: EIF4EBP1, Gene ID (GenBank): 1978, Gene: EIF4EBP2, Gene ID (GenBank): 1979), eIF4G (eIF4G1, eIF4G2, eIF4G3, Gene: EIF4G1, Gene ID (GenBank): 1981, Gene: EIF4G2, Gene ID (GenBank): 1982, Gene: EIF4G3, Gene ID (GenBank): 8672), eIF4H (Gene: EIF4H; Gene ID (GenBank): 7458), eIF5A (eIF5A1, eIF5A2, Gene: EIF5A1, Gene ID (GenBank): 1984, Gene: EIF5A2, Gene ID (GenBank): 56648), eIF5 (Gene: EIF5; Gene ID (GenBank): 1983) and eIF6 (Gene: EIF6; Gene ID (GenBank): 3692).

In this respect, it should be noted that eIF4A preferably comprises the isoforms eIF4A1, eIF4A2, and/or eIF4A3. Further, eIF4E preferably comprises the isoforms eIF4E1, eIF4E2, and/or eIF4E3. Furthermore, eIF4G preferably comprises the isoforms eIF4G1, eIF4G2, and/or eIF4G3. In addition, eIF5A preferably comprises the isoforms eIF5A1 and/or eIF5A2. Moreover, 4E-BP preferably comprises the isoforms 4E-BP1 and/or 4E-BP2.

According to another preferred embodiment, the tumor to be treated with the compound is selected from the group consisting of lymphoma, glioma, colorectal carcinoma, hepatocellular carcinoma, cholangiocellular carcinoma, pancreatic cancer and lung cancer.

According to a preferred embodiment, the compound is eIF-5 and/or a nucleic acid molecule encoding said eIF and the tumor to be treated is lymphoma, colorectal carcinoma, glioma or hepatocellular carcinoma.

According to a preferred embodiment, the compound is eIF3M and/or a nucleic acid molecule encoding said eIF and the tumor to be treated is a glioma or colorectal carcinoma.

According to a preferred embodiment, the compound is eIF6 and/or a nucleic acid molecule encoding said eIF and the tumor to be treated is colorectal carcinoma, glioma or hepatocellular carcinoma.

According to a preferred embodiment, the compound is selected from the group consisting of eIF3H, eIF3M, eIF4B, eIF4E, eIF4G, eIF5, eIF6, eIF1 and combinations thereof and/or a nucleic acid molecule encoding one or more of said eIF according and the tumor to be treated is colorectal carcinoma.

According to a preferred embodiment, the compound is eIF2α, eIF5 or a combination thereof and/or a nucleic acid molecule encoding one or more of said eIFs and the tumor to be treated is hepatocellular carcinoma.

According to a preferred embodiment, the compound is selected from the group consisting of eIF2AK3, eIF-4E3, eIF5 and combinations thereof and/or a nucleic acid molecule encoding one or more of said eIF and the tumor to be treated is lymphoma.

According to a preferred embodiment, the compound is selected from the group consisting of eIF3A, eIF3B, eIF3C, eIF3I, eIF3M, eIF4A, eIF4G, eIF4H, eIF5, eIF6 and combinations thereof and/or a nucleic acid molecule encoding one or more of said eIF and the tumor to be treated is a glioma.

According to a preferred embodiment, the compound is selected from the group consisting of eIF1A, eIF3J, eIF3K, eIF6 and combinations thereof and/or a nucleic acid molecule encoding one or more of said eIF and the tumor to be treated is lung cancer.

According to a preferred embodiment, the eIF binding molecule and/or the shRNA and/or the siRNA for inhibiting expression of an eIF binds to or inhibits the expression of eIF2AK4, eIF2B4, eIF2C 3, eIF2D, eIF-2a, eIF2S2, eIF3B, eIF3C, eIF3D, eIF3F, eIF3G, eIF3L, eIF4B, 4E-BP, 4E-BP1, eIF4G, eIF4G1 or eIF5A and the tumor to be treated is lymphoma.

According to a preferred embodiment, the eIF binding molecule and/or the shRNA and/or the siRNA for inhibiting expression of an eIF binds to or inhibits the expression of eIF3A, eIF3B, eIF3C, eIF3I, eIF3M, eIF4A, eIF4A1, eIF4A2, eIF4A3, eIF4G, eIF4H, eIF5 or eIF6 and the tumor to be treated is a glioma.

According to a preferred embodiment, the eIF binding molecule and/or the shRNA and/or the siRNA for inhibiting expression of an eIF binds to or inhibits the expression of eIF1A, eIF3J, eIF3K or eIF6 and the tumor to be treated is lung carcinoma.

According to a preferred embodiment, the eIF binding molecule and/or the shRNA and/or the siRNA for inhibiting expression of an eIF binds to or inhibits the expression of eIF3H, eIF5 or eIF6 and the tumor to be treated is hepatocellular carcinoma.

According to a preferred embodiment, the eIF binding molecule and/or the shRNA and/or siRNA for inhibiting expression of an eIF binds to or inhibits the expression of eIF1, eIF3H, eIF3M, eIF4B, eIF4E, eIF4E2, eIF4E3, eIF4G, eIF4G1, eIF4G2, eIF4G3, eIF5 or eIF6 and the tumor to be treated is colorectal carcinoma.

The compounds can be administered to a person suffering from cancer and in need thereof. The compounds can be administered by any means known in the art including, but not limited to oral or parenteral routes, including intravenous, intramuscular, intrathecal, subcutaneous, transdermal and airway (aerosol) administration. The compounds can also be administered by intravenous infusion or injection.

The compounds are administered to patients at a dose sufficient to increase, depress eIF levels or to reduce expression levels of the eIFs. It is particularly preferred that this effect is lasting for a certain period of time. In one embodiment, doses of the compounds are administered to a patient suffering from cancer preferably one to five times a day, once per day, every two days, every three days, every five days, every six days, every week, every two weeks, every four weeks. In a particularly preferred embodiment, the administrations can be maintained for one, two, three, or six months, or one year or longer. If siRNA and/or shRNA or any other nucleic acid molecule of the present invention is administered intravenous infusion and/or oral administration is preferred, whereby the compound is administered over a period of time, such as over a 5 minute, 10 minute, 15 minute, 20 minute, or 25 minute period or even longer.

The compounds are preferably administered in an amount of 0.1 to 10 mg/kg body weight, preferably 0.2 to 8 mg/kg body weight, more preferably 0.3 to 6 mg/kg body weight, more preferably 0.4 to 5 mg/kg body weight, more preferably 0.5 to 4 mg/kg body weight.

In a second aspect, the present invention relates to a composition comprising at least one compound according to the first aspect of the present invention for use in the treatment of a tumor.

The composition may comprise pharmaceutically acceptable excipients.

In a third aspect, the present invention relates to a method of diagnosing lung cancer in an individual (suspected of having lung cancer) comprising the step of:
- determining the level of at least one eukaryotic Initiation Factor (eIF) in a sample from an individual (suspected of having lung cancer),
- wherein the at least one eIF is selected from the group consisting of eIF1A and eIF6.

As to the Gene IDs of the eIFs, it is referred to the first aspect of the present invention.

For example, the level(s) of at least 1 eIF, or of all of the eIFs mentioned above is (are) determined.

Preferably, the level(s) of (i) eIF1A, (ii) eIF6, or (iii) eIF1A and eIF6 is (are) determined.

In one embodiment, the level of the at least one eIF is compared to a reference level of said at least one eIF. Thus, in one particular embodiment, the present invention relates to a method of diagnosing lung cancer in an individual (suspected of having lung cancer) comprising the steps of:
(i) determining the level of at least one eukaryotic Initiation Factor (eIF) in a sample from an individual (suspected of having lung cancer), wherein the at least one eIF is selected from the group consisting of eIF1A and eIF6, and
(ii) comparing the level of the at least one eIF to a reference level of said at least one eIF.

The above comparison allows to diagnose lung cancer in the individual suspected of having lung cancer. The individual may be diagnosed as suffering from lung cancer, i.e. being diseased, or as not suffering from lung cancer, i.e. being healthy.

The reference level may be any level which allows to determine whether an individual suffers from lung cancer or not.

It is preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one healthy individual, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 healthy individual(s). It is more preferred that the reference level is the level determined by measuring between 2 and 500 reference samples from between 2 and 500 healthy individuals. It is even more preferred that the reference level is determined by measuring between 50 and 500 reference samples from between 50 and 500 healthy individuals. It is most preferred that the reference level is determined by measuring between 100 and 500 reference samples from between 100 and 500 healthy individuals.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

As mentioned above, the level of the at least one eIF is compared to a reference level of said at least one eIF. Said reference level is the level determined by measuring a reference sample. For example, if the level of eIF6 is determined in a sample from an individual, it is compared to a reference level of eIF6 determined in a reference sample. Alternatively, if the level of eIF6 and the level of eIF1A is determined in a sample from an individual, both levels are compared to the respective reference levels, i.e. the level of eIF6 is compared to the reference level of eIF6 and the level of eIF1A is compared to the reference level of eIF1A in a reference sample.

It is further preferred that the level of the at least one eIF above the reference level indicates that the individual has lung cancer. Said at least one eIF is selected from the group consisting of eIF1A and eIF6.

Preferably, the level of the at least one eIF is at least 0.6-fold or 0.7-fold, more preferably at least 0.8-fold or 0.9-fold, even more preferably at least 1.2-fold or 1.5-fold, and most preferably at least 2.0-fold or 3.0-fold above the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold above the reference level.

It should be noted that with respect to eIF1A, it is preferred that the level is at least 2-fold above the reference level. It is more preferred that the level is at least 6-fold above the reference level.

With respect to eIF6, it is preferred that the level is at least 2-fold above the reference level. It is more preferred that the level is at least 4-fold above the reference level.

FIG. 33 shows single eIFs and a set of eIFs which level is preferably determined in a method of diagnosing lung cancer in an individual.

It is also preferred that the lung cancer is a non-small lung cancer (NSCLC), preferably an adenocarcinoma (ADC) or a squamous cell carcinoma (SQCC).

It is particularly preferred that the lung cancer is an adenocarcinoma (ADC) and the at least one eIF is selected from the group consisting of eIF1A and eIF6. The level of said at least one eIF is preferably above the reference level. It indicates that the individual has an adenocarcinoma (ADC). Alternatively, it is particularly preferred that the lung cancer is a squamous cell carcinoma (SQCC) and the at least one eIF is selected from the group consisting of eIF1A and eIF6. The level of said at least one eIF is preferably above the reference level. It indicates that the individual has a squamous cell carcinoma (SQCC).

In a fourth aspect, the present invention relates to a method of providing a prognosis to an individual suffering from lung cancer comprising the step of:
- determining the level of eIF6 in a sample from an individual suffering from lung cancer.

As to the Gene ID of eIF6, it is referred to the first aspect of the present invention.

In one embodiment, the level of eIF6 is compared to a reference level of said eIF6. Thus, in one particular embodiment, the present invention relates to a method of providing a prognosis to an individual suffering from lung cancer comprising the steps of:
(i) determining the level of eIF6 in a sample from an individual suffering from lung cancer, and (ii) comparing the level of eIF6 to a reference level of said eIF6.

The above comparison allows to provide a prognosis to an individual suffering from lung cancer. It may be determined that the individual suffering from lung cancer has a good prognosis or poor prognosis.

The reference level may be any level which allows to provide a prognosis to an individual suffering from lung cancer. Said prognosis may a good prognosis or poor prognosis.

It is preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient suffering from lung cancer, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) suffering from lung cancer. It is more preferred that the reference level is the level determined by measuring between 2 and 500 reference samples from between 2 and 500 patients suffering from lung cancer. It is even more preferred that the reference level is determined by measuring between 50 and 500 reference samples from between 50 and 500 patients suffering from lung cancer. It is most preferred that the reference level is determined by measuring between 100 and 500 reference samples from between 100 and 500 patients suffering from lung cancer.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

It is further preferred that the level of eIF6 below the reference level of eIF6 indicates a good prognosis.

Preferably, the level of eIF6 is at least 0.6-fold or 0.7-fold, more preferably at least 0.8-fold or 0.9-fold, even more preferably at least 1.2-fold or 1.5-fold, and most preferably at least 2.0-fold or 3.0-fold below the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold below the reference level.

Preferably, the lung cancer is a non-small lung cancer (NSCLC), more preferably an adenocarcinoma (ADC) or a squamous cell carcinoma (SQCC).

In a fifth aspect, the present invention relates to a method of diagnosing colorectal cancer in an individual (suspected of having colorectal cancer) comprising the step of:
determining the level of at least one eukaryotic Initiation Factor (eIF) in a sample from an individual (suspected of having colorectal cancer),
wherein the at least one eIF is selected from the group consisting of eIF1, eIF5, and eIF6.

As to the Gene IDs of the eIFs, it is referred to the first aspect of the present invention.

For example, the level(s) of at least 1, at least 2 eIF(s), or of all of the eIFs mentioned above is (are) determined.

Preferably, the level(s) of (i) eIF1, (ii) eIF5, (iii) eIF6, (iv) eIF1 and eIF5, (v) eIF1 and eIF6, (vi) eIF5 and eIF6, or (vii) eIF1, eIF5, and eIF6 is (are) determined.

In one embodiment, the level of the at least one eIF is compared to a reference level of said at least one eIF. Thus, in one particular embodiment, the present invention relates to a method of diagnosing colorectal cancer in an individual (suspected of having colorectal cancer) comprising the steps of:
(i) determining the level of at least one eukaryotic Initiation Factor (eIF) in a sample from an individual (suspected of having colorectal cancer), wherein the at least one eIF is selected from the group consisting of eIF1, eIF5, and eIF6, and
(ii) comparing the level of the at least one eIF to a reference level of said at least one eIF.

The above comparison allows to diagnose colorectal cancer in the individual suspected of having colorectal cancer. The individual may be diagnosed as suffering from colorectal cancer, i.e. being diseased, or as not suffering from colorectal cancer, i.e. being healthy.

The reference level may be any level which allows to determine whether an individual suffers from colorectal cancer or not.

It is preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one healthy individual, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 healthy individual(s). It is more preferred that the reference level is the level determined by measuring between 2 and 500 reference samples from between 2 and 500 healthy individuals. It is even more preferred that the reference level is determined by measuring between 50 and 500 reference samples from between 50 and 500 healthy individuals. It is most preferred that the reference level is determined by measuring between 100 and 500 reference samples from between 100 and 500 healthy individuals.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

It is further preferred that the level of the at least one eIF above the reference level indicates that the individual has colorectal cancer. Said at least one eIF is selected from the group consisting of eIF1, eIF5, and eIF6.

Preferably, the level of the at least one eIF is at least 0.6-fold or 0.7-fold, more preferably at least 0.8-fold or 0.9-fold, even more preferably at least 1.2-fold or 1.5-fold, and most preferably at least 2.0-fold or 3.0-fold above the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold above the reference level.

The colorectal cancer is preferably colon cancer (CC) or rectum cancer (RC).

In a sixth aspect, the present invention relates to a method of differentiating between colon cancer (CC) and rectum cancer (RC) in an individual comprising the step of:
determining the level of at least one eukaryotic Initiation Factor (eIF) in a sample from an individual,
wherein the at least one eIF is selected from the group consisting of eIF1, eIF5, and eIF6.

As to the Gene IDs of the eIFs, it is referred to the first aspect of the present invention.

For example, the level(s) of at least 1, at least 2 eIF(s), or of all of the eIFs mentioned above is (are) determined.

Preferably, the level(s) of (i) eIF1, (ii) eIF5, (iii) eIF6, (iv) eIF1 and eIF5, (v) eIF1 and eIF6, (vi) eIF5 and eIF6, or (vii) eIF1, eIF5, and eIF6 is (are) determined.

In one embodiment, the level of the at least one eIF is compared to a reference level of said at least one eIF. Thus, in one particular embodiment, the present invention relates to a method of differentiating between colon cancer (CC) and rectum cancer (RC) in an individual comprising the steps of:
(i) determining the level of at least one eukaryotic Initiation Factor (eIF) in a sample from an individual,
wherein the at least one eIF is selected from the group consisting of eIF1, eIF5, and eIF6, and
(ii) comparing the level of the at least one eIF to a reference level of said at least one eIF.

The above comparison allows to decide whether an individual suffers from colon cancer (CC) or rectum cancer (RC).

The reference level may be any level which allows to differentiate between the above described diseases or conditions, namely colon cancer (CC) and rectal cancer (RC).

It is preferred that the reference level is the level determined by measuring at least one reference sample from at least one patient with colon cancer, or at least one patient with rectum cancer.

It is particularly preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with colon cancer, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with colon cancer. It is more preferred that the reference level is the level determined by measuring between 2 and 500 reference samples from between 2 and 500 patients with colon cancer. It is even more preferred that the reference level is determined by measuring between 50 and 500 reference samples from between 50 and 500 patients with colon cancer. It is most preferred that the reference level is determined by measuring between 100 and 500 reference samples from between 100 and 500 patients with colon cancer.

It is also particularly preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with rectum cancer, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with rectum cancer. It is more preferred that the reference level is the level determined by measuring between 2 and 500 reference samples from between 2 and 500 patients with rectum cancer. It is even more preferred that the reference level is determined by measuring between 50 and 500 reference samples from between 50 and 500 patients with rectum cancer. It is most preferred that the reference level is determined by measuring between 100 and 500 reference samples from between 100 and 500 patients with rectum cancer.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

It is more preferred that
(i) the reference level is the level determined by measuring at least one reference sample from at least one patient with colon cancer, and wherein the level of eIF1 below the reference level indicates that the individual has rectum cancer,
(ii) the reference level is the level determined by measuring at least one reference sample from at least one patient with rectum cancer, and wherein the level of eIF1 above the reference level indicates that the individual has colon cancer,
(iii) the reference level is the level determined by measuring at least one reference sample from at least one patient with colon cancer, and wherein the level of eIF5 above the reference level indicates that the individual has rectum cancer,
(iv) the reference level is the level determined by measuring at least one reference sample from at least one patient with rectum cancer, and wherein the level of eIF5 below the reference level indicates that the individual has colon cancer,
(v) the reference level is the level determined by measuring at least one reference sample from at least one patient with colon cancer, and wherein the level of eIF6 above the reference level indicates that the individual has rectum cancer, and/or
(vi) the reference level is the level determined by measuring at least one reference sample from at least one patient with rectum cancer, and wherein the level of eIF6 below the reference level indicates that the individual has colon cancer.

Preferably, the level of the at least one eIF is at least 0.6-fold or 0.7-fold, more preferably at least 0.8-fold or 0.9-fold, even more preferably at least 1.2-fold or 1.5-fold, and most preferably at least 2.0-fold or 3.0-fold below/above the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold below/above the reference level.

In a seventh aspect, the present invention relates to a method of determining whether an individual (suffering from colorectal cancer) responds to a therapeutic treatment of colorectal cancer comprising the step of:
- determining the level of at least one eukaryotic Initiation Factor (eIF) in a sample from an individual (suffering from colorectal cancer),
- wherein the at least one eIF is selected from the group consisting of eIF1, eIF5, and eIF6.

As to the Gene IDs of the eIFs, it is referred to the first aspect of the present invention.

For example, the level(s) of at least 1, at least 2 eIF(s), or of all of the eIFs mentioned above is (are) determined.

Preferably, the level(s) of (i) eIF1, (ii) eIF5, (iii) eIF6, (iv) eIF1 and eIF5, (v) eIF1 and eIF6, (vi) eIF5 and eIF6, or (vii) eIF1, eIF5, and eIF6 is (are) determined.

It is preferred that the individual is an individual to whom at least once (e.g. once, twice, or thrice/1, 2, or 3 times) a drug to be used in said therapeutic treatment is administered or has been administered. The drug to be used in said therapeutic treatment may be selected from the group consisting of oxaliplatin, irinotecan, cetuximab, afatinib, avastin, regorafenib, nintedanib, and volitinib. The way of administration may be oral, nasal, rectal, parenteral, vaginal, or topical. Parental administration includes subcutaneous, intracutaneous, intramuscular, intravenous or intraperitoneal administration.

It is further preferred that the sample is isolated from the individual after at least the first (e.g. first, second, or third) administration of said drug. It is particularly preferred that the sample is isolated from the individual in a time period of between 12 months and 1 day after at least the first (e.g. first, second, or third) administration of said drug. It is particularly more preferred that the sample is isolated from the individual in a time period of between 6 months and 1 day after at least the first (e.g. first, second, or third) administration of said drug. It is particularly even more preferred that the sample is isolated from the individual in a time period of between 1 month and 1 day after at least the first (e.g. first, second, or third) administration of said drug. It is particularly most preferred that the sample is isolated from the individual in a time period of between 1 week and 1 day after at least the first (e.g. first, second, or third) administration of said drug. For example, the sample is isolated from the individual 1, 2, 3, 4, 5, 6, day(s), 1, 2, 3 week(s), 1, 2, 3, 4, 5, 6, 7, 8, 9, 10, 11, or 12 month(s) after at least the first (e.g. first, second, or third) administration of said drug.

It is also (alternatively or additionally) preferred that the level of the at least one eIF is compared to a reference level of said at least one eIF. Thus, in one particular embodiment, the present invention relates to a method of determining whether an individual (suffering from colorectal cancer) responds to a therapeutic treatment of colorectal cancer comprising the steps of:
(i) determining the level of at least one eukaryotic Initiation Factor (eIF) in a sample from an individual (suffering from colorectal cancer), wherein the at least one eIF is selected from the group consisting of eIF1, eIF5, and eIF6, and
(ii) comparing the level of the at least one eIF to a reference level of said at least one eIF.

As mentioned above, it is preferred that the individual is an individual to whom at least once (e.g. once, twice, or thrice, or 1, 2, or 3 times) a drug to be used in said therapeutic treatment is administered or has been administered. The drug to be used in said therapeutic treatment may be selected from the group consisting of oxaliplatin, irinotecan, cetuximab, afatinib, avastin, regorafenib, nintedanib, and volitinib. It is further preferred that the sample is isolated from the individual after at least the first (e.g. first, second, or third) administration of said drug.

The reference level may be any level which allows to determine whether the individual suffering from colorectal cancer responds to a therapeutic treatment of colorectal cancer.

It is preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with colorectal cancer, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with colorectal cancer. It is more preferred that the reference level is the level determined by measuring between 2 and 500 reference samples from between 2 and 500 patients with colorectal cancer. It is even more preferred that the reference level is determined by measuring between 50 and 500 reference samples from between 50 and 500 patients with colorectal cancer. It is most preferred that the reference level is determined by measuring between 100 and 500 reference samples from between 100 and 500 patients with colorectal cancer.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

It is also (alternatively or additionally) preferred that the reference level is the level determined in a reference sample isolated from the (same) individual prior to the administration of said drug. It is particularly preferred that the reference sample is isolated from the (same) individual in a time period of between 3 months and immediately prior to the administration of said drug. It is particularly more preferred that the reference sample is isolated from the (same) individual in a time period of between 1 month and immediately prior to the administration of said drug. It is particularly even more preferred that the reference sample is isolated from the (same) individual in a time period of between 3 weeks and immediately prior to the administration of said drug. It is particularly most preferred that the reference sample is isolated from the (same) individual in a time period of between 1 day and immediately prior to the administration of said drug or between 1 hour and immediately prior to the administration of said drug. For example, the reference sample is isolated from the (same) individual immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) prior to the administration of said drug.

Preferably, the individuals/patients, from which the samples/reference samples are, have undergone a wash-out period to remove any pharmaceutical substances from the body. For example, the individuals that receive or have received a drug for therapeutic treatment of colorectal cancer have undergone a 3-month was-out period prior to the administration of said drug.

It is more preferred that the level of the at least one eIF below the reference level indicates that the individual responds to said treatment of colorectal cancer. Said at least one eIF is selected from the group consisting of eIF1, eIF5, and eIF6.

Preferably, the level of the at least one eIF is at least 0.6-fold or 0.7-fold, more preferably at least 0.8-fold or 0.9-fold, even more preferably at least 1.2-fold or 1.5-fold, and most preferably at least 2.0-fold or 3.0-fold below the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold below the reference level.

The therapeutic treatment for colorectal cancer may be selected from the group consisting of the administration of a drug, chemotherapy, radiotherapy, and a combination thereof. Preferably, the therapeutic treatment for colorectal cancer comprises the administration of a drug. The drug is preferably selected from the group consisting of oxaliplatin, irinotecan, cetuximab, afatinib, avastin, regorafenib, nintedanib, and volitinib.

The colorectal cancer is preferably colon cancer (CC) or rectal cancer (RC).

In an eight aspect, the present invention relates to a method of determining the course of colorectal cancer in an individual (suffering from colorectal cancer) comprising the step of:
  determining the level of at least one eukaryotic Initiation Factor (eIF) in a sample from an individual (suffering from colorectal cancer),
  wherein the at least one eIF is selected from the group consisting of eIF1, eIF5, and eIF6.

As to the Gene IDs of the eIFs, it is referred to the first aspect of the present invention.

For example, the level(s) of at least 1, at least 2 eIF(s), or of all of the eIFs mentioned above is (are) determined.

Preferably, the level(s) of (i) eIF1, (ii) eIF5, (iii) eIF6, (iv) eIF1 and eIF5, (v) eIF1 and eIF6, (vi) eIF5 and eIF6, or (vii) eIF1, eIF5, and eIF6 is (are) determined.

In one embodiment, the level of the at least one eIF is compared to a reference level of said at least one eIF. Thus, in one particular embodiment, the present invention relates to a method of determining the course of colorectal cancer in an individual (suffering from colorectal cancer) comprising the steps of:
  (i) determining the level of at least one eukaryotic Initiation Factor (eIF) in a sample from an individual (suffering from colorectal cancer), wherein the at least one eIF is selected from the group consisting of eIF1, eIF5, and eIF6, and
  (ii) comparing the level of the at least one eIF to a reference level of said at least one eIF.

The above comparison allows to determine the course of colorectal cancer in the individual suffering from colorectal cancer. It may be determined that colorectal cancer worsens in the individual, that colorectal cancer does not worsen/is stable in the individual, or that colorectal cancer improves in the individual.

The reference level may be any level which allows to determine the course of colorectal cancer.

It is preferred that the reference level is the level determined by measuring at least one reference sample from
  at least one healthy individual, or
  at least one patient with colorectal cancer.

It is particularly preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one healthy individual, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 healthy individual(s). It is more preferred that the reference level is the level determined by measuring between 2 and 500 reference samples from between 2 and 500 healthy individuals. It is even more preferred that the reference level is determined by measuring between 50 and 500 reference samples from between 50 and 500 healthy individuals. It is most preferred that the reference level is determined by measuring between 100 and 500 reference samples from between 100 and 500 healthy individuals.

It is further particularly preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with colorectal cancer, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with colorectal cancer. It is more preferred that the reference level is the level determined by measuring between 2 and 500 reference samples from between 2 and 500 patients with colorectal cancer. It is even more preferred that the reference level is determined by measuring between 50 and 500 reference samples from between 50 and 500 patients with colorectal cancer. It is most preferred that the reference level is determined by measuring between 100 and 500 reference samples from between 100 and 500 patients with colorectal cancer.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

In one alternative or additional embodiment, said determining comprises determining the level of the at least one eIF in a sample at a first point in time and in at least one further sample at a later point in time and comparing said levels determined at the different time points.

Thus, in one particular embodiment, the present invention relates to a method comprising the steps of:
  (i) determining the level of at least one eIF in a sample from an individual (suffering from colorectal cancer) at a first point in time and in at least one further sample at a later point in time,
    wherein the at least one eIF is selected from the group consisting of eIF1, eIF5, and eIF6, and
  (ii) comparing said levels determined at the different time points.

This proceeding allows to determine the course of colorectal cancer in an individual suffering from colorectal cancer over an extended period of time, such as years.

It is further preferred that the level which
(i) increases over time indicates that colorectal cancer worsens in the individual,
(ii) does not change over time indicates that colorectal cancer does not worsen/is stable in the individual, or
(iii) decreases over time indicates that colorectal cancer improves in the individual.

The increase may be at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold over time. For example, the increase may be at least 0.6-fold over 1 year (12 months) or at least 1.2-fold over 2 years (24 months).

The decrease may be at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold over time. For example, the decrease may be at least 0.6-fold over 1 year (12 months) or at least 1.2-fold over 2 years (24 months).

"Stable", as mentioned above, means that the level varies overtime between 0 and <20%, e.g. 0, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 19.9, 19.99, or 19.999%. "Stable" in this respect may also mean that the detected level variation is within the accuracy of a measurement. The accuracy of a measurement depends on the measurement method used. Preferably, the level is constant over time.

The time period between the first point in time and the later point(s) in time preferably amounts to at least 1 day, at least 2 days, at least 3 days, at least 4 days, at least 5 days, at least 6 days, at least 7 days (1 week), at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months (1 year), at least 24 months (2 years), at least 3 years, at least 4 years, at least 5 years, at least 6 years, at least 7 years, at least 8 years, at least 9 years, or at least 10 years. For example, the individual may be routinely checked, e.g. once or twice a year. The individual may be (re)tested at 2, 3, 4, 5, 6 7, 8, 9, or 10 time points (first point in time and further point(s) in time).

In addition to the determination of the course of colorectal cancer, the treatment of this disease can be monitored. It is namely preferred that the individual receives or has received a treatment, in particular a therapeutic treatment, of colorectal cancer during the determination of the course of colorectal cancer. Thus, it is preferred that the individual receives or has received a therapeutic treatment of colorectal cancer.

Preferably,
(i) the level of the at least one eIF which decreases over time indicates that the individual responds to said treatment,
(ii) the level of the at least one eIF which does not change over time indicates that the individual does not respond to said treatment, or
(iii) level of the at least one eIF which increases over time indicates that the individual does not respond to said treatment.

The treatment of colorectal cancer may be selected from the group consisting of the administration of a drug, chemotherapy, radiotherapy, and a combination thereof. The drug to be used in said therapeutic treatment may be selected from the group consisting of oxaliplatin, irinotecan, cetuximab, afatinib, avastin, regorafenib, nintedanib, and volitinib.

The individual may receive a treatment during the complete determination/monitoring process (e.g. the administration of a drug) or may receive a treatment before, at, or after a first point in time (e.g. the administration of a drug) and may be retested at a later point in time. In particular, said first point in time may be before the initiation of a treatment and said later point in time may be during the treatment and/or after the treatment. If the treatment encompasses the administration of a drug and the individual responds to said treatment, the drug administration may be continued, the dose of the drug may be reduced, or the drug administration may be stopped. If the treatment encompasses the administration of a drug and the individual does not respond to said treatment, the dose of the drug may be increased, the drug may be changed, or the therapy mode may be changed, e.g. from drug administration to surgery or radiotherapy.

The colorectal cancer is preferably colon cancer (CC) or rectal cancer (RC).]

In a ninth aspect, the present invention relates to a method of diagnosing a glioma in an individual (suspected of suffering from a glioma) comprising the step of:
determining the level of at least one eukaryotic Initiation Factor (eIF) in a sample from an individual (suspected of suffering from a glioma),
wherein the at least one eIF is selected from the group consisting of eIF3I, eIF3M, eIF4A, eIF4H, eIF5, and eIF6.

In this respect, it should be noted that eIF4A preferably comprises the isoforms eIF4A1, eIF4A2, and/or eIF4A3.

As to the Gene IDs of the eIFs, it is referred to the first aspect of the present invention.

For example, the level(s) of at least 1, at least 2, at least 3, at least 4, at least 5 eIF(s), or of all of the eIFs mentioned above is (are) determined.

In one embodiment, the level of the at least one eIF is compared to a reference level of said at least one eIF. Thus, in one particular embodiment, the present invention relates to a method of diagnosing a glioma in an individual (suspected of suffering from a glioma) comprising the steps of:
(i) determining the level of at least one eukaryotic Initiation Factor (eIF) in a sample from an individual (suspected of suffering from a glioma), wherein the at least one eIF is selected from the group consisting of eIF3I, eIF3M, eIF4A, eIF4H, eIF5, and eIF6, and
(ii) comparing the level of the at least one eIF to a reference level of said at least one eIF.

The above comparison allows to diagnose a glioma in the individual suspected of suffering from a glioma. The individual may be diagnosed as suffering from a glioma, i.e. being diseased, or as not suffering from a glioma, i.e. being healthy.

The reference level may be any level which allows to determine whether an individual suffers from a glioma or not.

It is preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one healthy individual, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 healthy individual(s). It is more preferred that the reference level is the level determined by measuring between 2 and 500 reference samples from between 2 and 500 healthy individuals. It is even more preferred that the reference level is determined by measuring between 50 and 500 reference samples from between 50 and 500 healthy individuals. It is most preferred that the reference level is determined by measuring between 100 and 500 reference samples from between 100 and 500 healthy individuals.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

It is further preferred that the level of the at least one eIF above the reference level indicates that the individual suffers from a glioma. Said at least one eIF is selected from the group consisting of eIF3I, eIF3M, eIF4A, eIF4H, eIF5, and eIF6.

Preferably, the level of the at least one eIF is at least 1.5-fold or 1.6-fold, more preferably at least 1.8-fold or 1.9-fold, even more preferably at least 2-fold or 2.5-fold, and most preferably at least 2.5-fold, 3.0-fold, 3.5-fold, or 4.0-fold above the reference level. For example, the level of the at least one eIF is at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3.0-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, or at least 4.0-fold above the reference level.

It should be noted that with respect to eIF3I, it is preferred that the level is at least 1.5-fold above the reference level. It is more preferred that the level is at least 3.0-fold above the reference level.

With respect to eIF3M, it is preferred that the level is at least 1.5-fold above the reference level. It is more preferred that the level is at least 2.0-fold above the reference level.

With respect to eIF4A, it is preferred that the level is at least 1.5-fold above the reference level. It is more preferred that the level is at least 2.0-fold above the reference level.

With respect to eIF4H, it is preferred that the level is at least 1.5-fold above the reference level. It is more preferred that the level is at least 2.0-fold above the reference level.

With respect to eIF5, it is preferred that the level is at least 1.5-fold above the reference level. It is more preferred that the level is at least 4.0-fold above the reference level.

With respect to eIF6, it is preferred that the level is at least 1.5-fold above the reference level. It is more preferred that the level is at least 3.0-fold above the reference level.

FIG. 34 shows single eIFs and sets of eIFs which level is preferably determined in a method of diagnosing a glioma in an individual. These sets comprise 2, 3, 4, 5, or 6 eIFs.

The glioma is preferably selected from the group consisting of an astrocytoma, ependymoma, oligodendrogliomas, and brainstem glioma. More preferably, the glioma is an astrocytoma.

In a tenth aspect, the present invention relates to a method of grading a glioma in an individual (suffering from a glioma) comprising the step of
  determining the level of at least one eukaryotic Initiation Factor (eIF) in a sample from an individual (suffering from a glioma),
  wherein the at least one eIF is selected from the group consisting of eIF3I, eIF4A, eIF4H, and eIF6.

In this respect, it should be noted that eIF4A preferably comprises the isoforms eIF4A1, eIF4A2, and/or eIF4A3.

As to the Gene IDs of the eIFs, it is referred to the first aspect of the present invention.

For example, the level(s) of at least 1, at least 2, at least 3 eIF(s), or of all of the eIFs mentioned above is (are) determined.

Preferably, the level(s) of (i) eIF3I, (ii) eIF4A, (iii) eIF4H, (iv) eIF6, (v) eIF3I and eIF4A, (vi) eIF3I and eIF4H, (vii) eIF3I and eIF6, (viii) eIF4A and eIF4H, (ix) eIF4A and eIF6, (x) eIF4H, and eIF6, (xi) eIF3I, eIF4A, and eIF4H, (xii) eIF3I, eIF4H, and eIF6, (xiii) eIF3I, eIF4A, and eIF6, (xiv) eIF4A, eIF4H, and eIF6, and (xv) eIF3I, eIF4A, eIF4H, and eIF6 is (are) determined.

In one embodiment, the level of the at least one eIF is compared to at least one reference level (e.g. to at least 1, 2, 3 reference level(s), or 4 reference levels) of said at least one eIF. Thus, in one particular embodiment, the present invention relates to a method of grading a glioma in an individual (suffering from a glioma) comprising the steps of:
  (i) determining the level of at least one eukaryotic Initiation Factor (eIF) in a sample from an individual (suffering from a glioma), wherein the at least one eIF is selected from the group consisting of eIF3I, eIF4A, eIF4H, and eIF6, and
  (ii) comparing the level of the at least one eIF to at least one reference level (e.g. to at least 1, 2, 3 reference level(s), or 4 reference levels) of said at least one eIF.

The above comparison allows to grade a glioma in the individual. It may be determined that the individual suffers from a glioma of grade I, II, III, or IV.

The reference level may be any level which allows the grading of a glioma in an individual.

It is preferred that the at least one reference level is the level determined by measuring at least one reference sample
  from at least one patient with a glioma of grade I,
  from at least one patient with a glioma of grade II,
  from at least one patient with a glioma of grade III, or
  from at least one patient with a glioma of grade IV.

It is particularly preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with a glioma of grade I, II, III, or IV, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with a glioma of grade I, II, III, or IV. It is more preferred that the reference level is the level determined by measuring between 2 and 500 reference samples from between 2 and 500 patients with a glioma of grade I, II, III, or IV. It is even more preferred that the reference level is determined by measuring between 50 and 500 reference samples from between 50 and 500 patients with a glioma of grade I, II, III, or IV. It is most preferred that the reference level is determined by measuring between 100 and 500 reference samples from between 100 and 500 patients with a glioma of grade I, II, III, or IV.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

In this respect, is should be noted that grades I and II characterize a low-grade (benign) glioma and grades III and IV characterize a high-grade (malignant) glioma. In particular, with respect to a astrocytoma, grade I refers to/means a pilozytic astrocytoma, grade II refers to/means a diffuse astrocytoma, grade III refers to/means an anaplastic astrocytoma, and grade IV refers to/means a glioblastoma multiform.

It is more preferred that
(i) the at least one reference level is the level determined by measuring at least one reference sample from at least one patient with a glioma of grade I, wherein the at least one eIF is selected from the group consisting of eIF3I, eIF4H, and eIF6, and wherein the level of the at least one eIF above the reference level indicates that the individual has a glioma of grade II, III, or IV,
(ii) the at least one reference level is the level determined by measuring at least one reference sample from at least one patient with a glioma of grade II, wherein the at least one eIF is selected from the group consisting of eIF3I, eIF4H, and eIF6, and wherein the level of the at least one eIF above the reference level indicates that the individual has a glioma of grade III or IV, and/or
(iii) the at least one reference level is the level determined by measuring at least one reference sample from at least one patient with a glioma of grade III, wherein the at least one eIF is selected from the group consisting of eIF3I, eIF4H, and eIF6, and
wherein the level of the at least one eIF above the reference level indicates that the individual has a glioma of grade IV.

Preferably, the level of the at least one eIF is at least 1.5-fold or 1.6-fold, more preferably at least 1.8-fold or 1.9-fold, even more preferably at least 2-fold or 2.5-fold, and most preferably at least 2.5-fold, 3.0-fold, 3.5-fold, or 4.0-fold above the reference level. For example, the level of the at least one eIF is at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3.0-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, or at least 4.0-fold above the reference level.

The glioma is preferably selected from the group consisting of an astrocytoma, ependymoma, oligodendrogliomas, and brainstem glioma.

In an eleventh aspect, the present invention relates a method of differentiating between a low-grade (benign) glioma and a high-grade (malignant) glioma in an individual comprising the step of:
determining the level of at least one eukaryotic Initiation Factor (eIF) in a sample from an individual,
wherein the at least one eIF is selected from the group consisting of eIF3I, eIF4H, eIF5, and eIF6.

As to the Gene IDs of the eIFs, it is referred to the first aspect of the present invention.

For example, the level(s) of at least 1, at least 2, at least 3 eIF(s), or of all of the eIFs mentioned above is (are) determined.

Preferably, the level(s) of (i) eIF3I, (ii) eIF4H, (iii) eIF5, (iv) eIF6, (v) eIF3I and eIF4H, (vi) eIF3I and eIF5, (vii) eIF3I and eIF6, (viii) eIF4H and eIF5, (ix) eIF4H and eIF6, (x) eIF5 and eIF6, (xi) eIF3I, eIF4H, and eIF5 (xii) eIF3I, eIF4H, and eIF6, (xiii) eIF3I, eIF5, and eIF6, (xiv) eIF4H, eIF5, and eIF6, and (xv) eIF3I, eIF4H, eIF5, and eIF6 is (are) determined.

In one embodiment, the level of the at least one eIF is compared to a reference level/at least one reference level (e.g. to at least 1, 2, 3 reference level(s), or 4 reference levels) of said at least one eIF. Thus, in one particular embodiment, the present invention relates to a method of differentiating between a low-grade (benign) glioma and a high-grade (malignant) glioma in an individual comprising the steps of:
(i) determining the level of at least one eukaryotic Initiation Factor (eIF) in a sample from an individual, wherein the at least one eIF is selected from the group consisting of eIF3I, eIF4H, eIF5, and eIF6, and
(ii) comparing the level of the at least one eIF to a reference level/at least one reference level (e.g. to at least 1, 2, 3 reference level(s), or 4 reference levels) of said at least one eIF.

The above comparison allows to decide whether an individual suffers from a low-grade (benign) glioma (grades I or II) or a high-grade (malignant) glioma (grades III or IV).

The (at least one) reference level may be any level which allows to differentiate between the above described diseases or conditions, namely a low-grade (benign) glioma (grades I or II) and a high-grade (malignant) glioma (grades III or IV).

It is preferred that the (at least one) reference level is the level determined by measuring at least one reference sample from at least one patient with a low-grade (benign) glioma, or at least one patient with a high-grade (malignant) glioma.

It is particularly preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with a low-grade (benign) glioma, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with a low-grade (benign) glioma. It is more preferred that the reference level is the level determined by measuring between 2 and 500 reference samples from between 2 and 500 patients with a low-grade (benign) glioma. It is even more preferred that the reference level is determined by measuring between 50 and 500 reference samples from between 50 and 500 patients with a low-grade (benign) glioma. It is most preferred that the reference level is determined by measuring between 100 and 500 reference samples from between 100 and 500 patients with a low-grade (benign) glioma.

It is also particularly preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with a high-grade (malignant) glioma, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with with a high-grade (malignant) glioma. It is more preferred that the reference level is the level determined by measuring between 2 and 500 reference samples from between 2 and 500 patients with a high-grade (malignant) glioma. It is even more preferred that the reference level is determined by measuring between 50 and 500 reference samples from between 50 and 500 patients with a high-grade (malignant) glioma. It is most preferred that the reference level is determined by measuring between 100 and 500 reference samples from between 100 and 500 patients with a high-grade (malignant) glioma.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

It is more preferred that
(i) the (at least one) reference level is the level determined by measuring at least one reference sample from at least one patient with a low-grade (benign) glioma, and wherein the level of the at least one eIF selected from the group consisting of eIF3I, eIF4H, eIF5, and eIF6 above the reference level indicates that the individual has a high-grade (malignant) glioma, and/or
(ii) the (at least one) reference level is the level determined by measuring at least one reference sample from at least one patient with a high-grade (malignant) glioma, and wherein the level of the at least one eIF selected from the group consisting of eIF3I, eIF4H, eIF5, and eIF6 below the reference level indicates that the individual has a low-grade (benign) glioma.

Preferably, the low-grade (benign) glioma is a glioma of grades I or II and the high-grade (malignant) glioma is a glioma of grades III or IV.

In this case, it is further preferred that the at least one reference level is the level determined by measuring at least one reference sample from
from at least one patient with a glioma of grade I,
from at least one patient with a glioma of grade II,
from at least one patient with a glioma of grade III, or
from at least one patient with a glioma of grade IV.

It is particularly preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with a glioma of grade I, II, III or IV, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with a glioma of grade I, II, III or IV. It is more preferred that the reference level is the level determined by measuring between 2 and 500 reference samples from between 2 and 500 patients with a glioma of grade I, II, III or IV. It is even more preferred that the reference level is determined by measuring between 50 and 500 reference samples from between 50 and 500 patients with a glioma of grade I, II, III or IV. It is most preferred that the reference level is determined by measuring between 100 and 500 reference samples from between 100 and 500 patients with a glioma of grade I, II, III or IV.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

It is most preferred that
(i) the at least one reference level is the level determined by measuring at least one reference sample from at least one patient with a glioma of grade II, and wherein the level of eIF3I above the reference level indicates that the individual has a high-grade (malignant) glioma, in particular a glioma of grades III or IV,
(ii) the at least one reference level is the level determined by measuring at least one reference sample from at least one patient with a glioma of grade II, and wherein the level of eIF4H above the reference level indicates that the individual has a high-grade (malignant) glioma, in particular a glioma of grades III or IV,
(iii) the at least one reference level is the level determined by measuring at least one reference sample from at least one patient with a glioma of grade I, and wherein the level of eIF5 above the reference level indicates that the individual has a high-grade (malignant) glioma, in particular a glioma of grades III or IV,
(iv) the at least one reference level is the level determined by measuring at least one reference sample from at least one patient with a glioma of grades I or II, and wherein the level of eIF6 above the reference level indicates that the individual has a high-grade (malignant) glioma, in particular a glioma of grades III or IV,
(v) the at least one reference level is the level determined by measuring at least one reference sample from at least one patient with glioma of grade III, and wherein the level of eIF3I below the reference level indicates that the individual has a low-grade (benign) glioma, in particular a glioma of grades I or II,
(vi) the at least one reference level is the level determined by measuring at least one reference sample from at least one patient with a glioma of grade III, and wherein the level of eIF4H below the reference level indicates that the individual has a low-grade (benign) glioma, in particular a glioma of grades I or II,
(vii) the at least one reference level is the level determined by measuring at least one reference sample from at least one patient with a glioma of grade III, and wherein the level of eIF5 below the reference level indicates that the individual has a low-grade (benign) glioma, in particular a glioma of grades I or II, and/or
(viii) the at least one reference level is the level determined by measuring at least one reference sample from at least one patient with a glioma of grade III, and wherein the level of eIF6 below the reference level indicates that the individual has a low-grade (benign) glioma, in particular a glioma of grades I or II.

The glioma is preferably selected from the group consisting of an astrocytoma, ependymoma, oligodendrogliomas, and brainstem glioma.]

In a twelfth aspect, the present invention relates a method of providing a prognosis to an individual suffering from a glioma comprising the step of:
  determining the level of at least one eukaryotic Initiation Factor (eIF) in a sample from an individual,
  wherein the at least one eIF is selected from the group consisting of eIF3I, eIF4G, and eIF4H.

In this respect, it should be noted that eIF4G preferably comprises the isoforms eIF4G1, eIF4G2, and/or eIF4G3.

As to the Gene IDs of the eIFs, it is referred to the first aspect of the present invention.

For example, the level(s) of at least 1, at least 2 eIF(s), or of all of the eIFs mentioned above is (are) determined.

Preferably, the level(s) of (i) eIF3I, (ii) eIF4G, (iii) eIF4H, (iv) eIF3I and eIF4G, (v) eIF3I and eIF4H, (vi) eIF4G and eIF4H, and (vii) eIF3I, eIF4G, and eIF4H is (are) determined.

In one embodiment, the level of the at least one eIF is compared to a reference level of said at least one eIF. Thus, in one particular embodiment, the present invention relates to a method of providing a prognosis to an individual suffering from a glioma comprising the steps of:
  (i) determining the level of at least one eukaryotic Initiation Factor (eIF) in a sample from an individual suffering from a glioma,
    wherein the at least one eIF is selected from the group consisting of eIF3I, eIF4G, and eIF4H, and
  (ii) comparing the level of the at least one eIF to a reference level of said at least one eIF.

The above comparison allows to provide a prognosis to an individual suffering from a glioma. It may be determined that the individual suffering from a glioma has a good prognosis or poor prognosis.

The reference level may be any level which allows to provide a prognosis to an individual suffering from a glioma. Said prognosis may a good prognosis or poor prognosis.

It is preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with a glioma, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with a glioma. It is more preferred that the reference level is the level determined by measuring between 2 and 500 reference samples from between 2 and 500 patients with a glioma. It is even more preferred that the reference level is determined by measuring between 50 and 500 reference samples from between 50 and 500 patients with a glioma. It is most preferred that the reference level is determined by measuring between 100 and 500 reference samples from between 100 and 500 patients with a glioma.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

It is more preferred that the level of the at least one eIF below the reference level indicates a good prognosis. Said at least one eIF is selected from the group consisting of eIF3I, eIF4G, and eIF4H.

Preferably, the level of the at least one eIF is at least 0.6-fold or 0.7-fold, more preferably at least 0.8-fold or 0.9-fold, even more preferably at least 1.2-fold or 1.5-fold, and most preferably at least 2.0-fold or 3.0-fold below the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold below the reference level.

The glioma is preferably a low-grade glioma or a high-grade glioma. Preferably, the low-grade glioma is a glioma of grades I or II and the high-grade glioma is a glioma of grades III or IV.

In a thirteenth aspect, the present invention relates a method of determining whether an individual (suffering from a glioma) responds to a therapeutic treatment of a glioma comprising the step of:
  determining the level of at least one eukaryotic Initiation Factor (eIF) in a sample from an individual (suffering from a glioma),
  wherein the at least one eIF is selected from the group consisting of eIF3D, eIF3H, eIF3I, eIF3J, eIF3K, eIF3M, eIF4A, eIF4B, preferably peIF4B, eIF4E, eIF4H, and eIF6.

In this respect, it should be noted that eIF4A preferably comprises the isoforms eIF4A1, eIF4A2, and/or eIF4A3. Further, eIF4E preferably comprises the isoforms eIF4ET, eIF4E2, and/or eIF4E3. Furthermore, peIF4B is the phosphorylated form of eIF4B. peIF4B may also be designated as phoshpo-eIF4B.

As to the Gene IDs of the eIFs, it is referred to the first aspect of the present invention.

For example, the level(s) of at least 1, at least 2, at least 3, at least 4, at least 5, at least 6, at least 7, at least 8, at least 9, at least 10 eIF(s), or of all of the eIFs mentioned above is (are) determined.

It is preferred that the individual is an individual to whom at least once (e.g. once, twice, or thrice/1, 2, or 3 times) a drug to be used in said therapeutic treatment is administered or has been administered. The drug to be used in said therapeutic treatment may be selected from the group consisting of temozolomide, regorafenib, thalidomide, and bevacizumab. Preferably, the drug is selected from the group consisting of temozolomide and regorafenib. The way of administration may be oral, nasal, rectal, parenteral, vaginal, or topical. Parental administration includes subcutaneous, intracutaneous, intramuscular, intravenous or intraperitoneal administration.

It is further preferred that the sample is isolated from the individual after at least the first (e.g. first, second, or third) administration of said drug. It is particularly preferred that the sample is isolated from the individual in a time period of between 12 months and 1 day after at least the first (e.g. first, second, or third) administration of said drug. It is particularly more preferred that the sample is isolated from the individual in a time period of between 6 months and 1 day after at least the first (e.g. first, second, or third) administration of said drug. It is particularly even more preferred that the sample is isolated from the individual in a time period of between 1 month and 1 day after at least the first (e.g. first, second, or third) administration of said drug. It is particularly most preferred that the sample is isolated from the individual in a time period of between 1 week and 1 day after at least the first (e.g. first, second, or third) administration of said drug. For example, the sample is isolated from the individual 1, 2, 3, 4, 5, 6, day(s), 1, 2, 3 week(s), 1, 2, 3, 4, 5, 6, 7, 8, 9, 10, 11, or 12 month(s) after at least the first (e.g. first, second, or third) administration of said drug.

It is also (alternatively or additionally) preferred that the level of the at least one eIF is compared to a reference level of said at least one eIF. Thus, in one particular embodiment, the present invention relates to a method of determining whether an individual (suffering from a glioma) responds to a therapeutic treatment of a glioma comprising the steps of:
(i) determining the level of at least one eukaryotic Initiation Factor (eIF) in a sample from an individual (suffering from a glioma), wherein the at least one eIF is selected from the group consisting of eIF3D, eIF3H, eIF3I, eIF3J, eIF3K, eIF3M, eIF4A, eIF4B, preferably peIF4B, eIF4E, eIF4H, and eIF6, and
(ii) comparing the level of the at least one eIF to a reference level of said at least one eIF.

As mentioned above, it is preferred that the individual is an individual to whom at least once (e.g. once, twice, or thrice, or 1, 2, or 3 times) a drug to be used in said therapeutic treatment is administered or has been administered. The drug to be used in said therapeutic treatment may be selected from the group consisting of temozolomide, regorafenib, thalidomide, and bevacizumab. Preferably, the drug is selected from the group consisting of temozolomide and regorafenib. It is further preferred that the sample is isolated from the individual after at least the first (e.g. first, second, or third) administration of said drug.

The reference level may be any level which allows to determine whether the individual suffering from a glioma responds to a therapeutic treatment of glioma.

It is preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with a glioma, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with a glioma. It is more preferred that the reference level is the level determined by measuring between 2 and 500 reference samples from between 2 and 500 patients with a glioma. It is even more preferred that the reference level is determined by measuring between 50 and 500 reference samples from between 50 and 500 patients with a glioma. It is most preferred that the reference level is determined by measuring between 100 and 500 reference samples from between 100 and 500 patients with a glioma.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

It is also (alternatively or additionally) preferred that the reference level is the level determined in a reference sample isolated from the (same) individual prior to the administration of said drug. It is particularly preferred that the reference sample is isolated from the (same) individual in a time period of between 3 months and immediately prior to the administration of said drug. It is particularly more preferred that the reference sample is isolated from the (same) individual in a time period of between 1 month and immediately prior to the administration of said drug. It is particularly even more preferred that the reference sample is isolated from the (same) individual in a time period of between 3 weeks and immediately prior to the administration of said drug. It is particularly most preferred that the reference sample is isolated from the (same) individual in a time period of between 1 day and immediately prior to the administration of said drug or between 1 hour and immediately prior to the administration of said drug. For example, the reference sample is isolated from the (same) individual immediately, 10, 20, 30, 40, 50 minutes, 1, 2, 3, 4, 5, 6, 7, 8, 9, 10, 11, 12, 13, 14, 15, 16, 17, 18, 19, 20, 21, 22, 23 hour(s), 1, 2, 3, 4, 5, 6 day(s), 1, 2, 3 week(s), 1, 2, or 3 month(s) prior to the administration of said drug.

Preferably, the individuals/patients, from which the samples/reference samples are, have undergone a wash-out period to remove any pharmaceutical substances from the body. For example, the individuals that receive or have received a drug for therapeutic treatment of a glioma have undergone a 3-month was-out period prior to the administration of said drug.

It is more preferred that the level of the at least one eIF below the reference level indicates that the individual responds to said treatment of a glioma. Said at least one eIF is selected from the group consisting of eIF3D, eIF3H, eIF3I, eIF3J, eIF3K, eIF3M, eIF4A, peIF4B, eIF4E, eIF4H, and eIF6.

Preferably, the level of the at least one eIF is at least 0.6-fold or 0.7-fold, more preferably at least 0.8-fold or 0.9-fold, even more preferably at least 1.2-fold or 1.5-fold, and most preferably at least 2.0-fold or 3.0-fold below the reference level. For example, the level of the at least one eIF is at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold below the reference level.

The therapeutic treatment for a glioma may be selected from the group consisting of the administration of a drug, chemotherapy, radiotherapy, and a combination thereof. Preferably, the therapeutic treatment for colorectal cancer comprises the administration of a drug. The drug may be selected from the group consisting of temozolomide, regorafenib, thalidomide, and bevacizumab. Preferably, the drug is selected from the group consisting of temozolomide and regorafenib.

The glioma is preferably a high-grade glioma (malignant), in particular a glioma of grades III or IV.

In a fourteenth aspect, the present invention relates a method of determining the course of a glioma in an individual (suffering from a glioma) comprising the step of:
  determining the level of at least one eukaryotic Initiation Factor (eIF) in a sample from an individual (suffering from a glioma),
  wherein the at least one eIF is selected from the group consisting of eIF2α, preferably peIF2α, eIF3D, eIF3H, eIF3I, eIF3J, eIF3K, eIF3M, eIF4A, eIF4B, preferably peIF4B, eIF4E, eIF4H, and eIF6.

In this respect, it should be noted that eIF4A preferably comprises the isoforms eIF4A1, eIF4A2, and/or eIF4A3. Further, eIF4E preferably comprises the isoforms eIF4E1, eIF4E2, and/or eIF4E3. Furthermore, peIF2α is the phosphorylated form of eIF2α. In addition, peIF4B is the phosphorylated form of eIF4B. peIF4B may also be designated as phoshpo-eIF4B.

As to the Gene IDs of the eIFs, it is referred to the first aspect of the present invention.

For example, the level(s) of at least 1, at least 2, at least 3, at least 4, at least 5, at least 6, at least 7, at least 8, at least 9, at least 10, at least 11 eIF(s), or of all of the eIFs mentioned above is (are) determined.

In one embodiment, the level of the at least one eIF is compared to a reference level of said at least one eIF. Thus, in one particular embodiment, the present invention relates to a method of determining the course of a glioma in an individual (suffering from a glioma) comprising the steps of
(i) determining the level of at least one eukaryotic Initiation Factor (eIF) in a sample from an individual (suffering from a glioma),
  wherein the at least one eIF is selected from the group consisting of eIF2α, preferably peIF2α, eIF3D, eIF3H, eIF3I, eIF3J, eIF3K, eIF3M, eIF4A, eIF4B, preferably peIF4B, eIF4E, eIF4H, and eIF6, and
(ii) comparing the level of the at least one eIF to a reference level of said at least one eIF.

The above comparison allows to determine the course of a glioma in the individual suffering from a glioma. It may be determined that the glioma worsens in the individual, that the glioma does not worsen/is stable in the individual, or that the glioma improves in the individual.

The reference level may be any level which allows to determine the course of a glioma.

It is preferred that the reference level is the level determined by measuring at least one reference sample from
at least one healthy individual, or
at least one patient with a glioma.

It is particularly preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one healthy individual, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 healthy individual(s). It is more preferred that the reference level is the level determined by measuring between 2 and 500 reference samples from between 2 and 500 healthy individuals. It is even more preferred that the reference level is determined by measuring between 50 and 500 reference samples from between 50 and 500 healthy individuals. It is most preferred that the reference level is determined by measuring between 100 and 500 reference samples from between 100 and 500 healthy individuals.

It is further particularly preferred that the reference level is the level determined by measuring at least one reference sample, e.g. at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 reference sample(s), from at least one patient with a glioma, e.g. from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 250, 300, 400, 500, or 1.000 patient(s) with a glioma. It is more preferred that the reference level is the level determined by measuring between 2 and 500 reference samples from between 2 and 500 patients with a glioma. It is even more preferred that the reference level is determined by measuring between 50 and 500 reference samples from between 50 and 500 patients with a glioma. It is most preferred that the reference level is determined by measuring between 100 and 500 reference samples from between 100 and 500 patients with a glioma.

It is practicable to take one reference sample per subject for analysis. If additional reference samples are required, e.g. to determine the reference level in different reference samples, the same subject may be (re)tested. Said reference level may be an average reference level. It may be determined by measuring reference levels and calculating the "average" value (e.g. mean, median or modal value) thereof.

In one alternative or additional embodiment, said determining comprises determining the level of the at least one eIF in a sample at a first point in time and in at least one further sample at a later point in time and comparing said levels determined at the different time points.

Thus, in one particular embodiment, the present invention relates to a method comprising the steps of:
(i) determining the level of at least one eIF in a sample from an individual (suffering from a glioma) at a first point in time and in at least one further sample at a later point in time, wherein the at least one eIF is selected from the group consisting of eIF2α, preferably peIF2α, eIF3D, eIF3H, eIF3I, eIF3J, eIF3K, eIF3M, eIF4A, eIF4B, preferably peIF4B, eIF4E, eIF4H, and eIF6, and
(ii) comparing said levels determined at the different time points.

This proceeding allows to determine the course of a glioma in an individual suffering from a glioma over an extended period of time, such as years.

It is further preferred that the level which
(i) increases over time indicates that the glioma worsens in the individual,
(ii) does not change over time indicates that the glioma does not worsen/is stable in the individual, or
(iii) decreases over time indicates that the glioma improves in the individual.

The increase may be at least 1.5-fold or 1.6-fold, more preferably at least 1.8-fold or 1.9-fold, even more preferably at least 2-fold or 2.5-fold, and most preferably at least 2.5-fold, 3.0-fold, 3.5-fold, or 4.0-fold above the reference level. For example, the level of the at least one eIF is at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, at least 3.0-fold, at least 3.1-fold, at least 3.2-fold, at least 3.3-fold, at least 3.4-fold, at least 3.5-fold, at least 3.6-fold, at least 3.7-fold, at least 3.8-fold, at least 3.9-fold, or at least 4.0-fold over time. For example, the increase may be at least 1.5-fold over 1 year (12 months) or at least 3.0-fold over 2 years (24 months).

The decrease may be at least 0.6-fold, at least 0.7-fold, at least 0.8-fold, at least 0.9-fold, at least 1.0-fold, at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2.0-fold, at least 2.1-fold, at least 2.2-fold, at least 2.3-fold, at least 2.4-fold, at least 2.5-fold, at least 2.6-fold, at least 2.7-fold, at least 2.8-fold, at least 2.9-fold, or at least 3.0-fold over time. For example, the decrease may be at least 0.6-fold over 1 year (12 months) or at least 1.2-fold over 2 years (24 months).

"Stable", as mentioned above, means that the level varies overtime between 0 and <20%, e.g. 0, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 19.9, 19.99, or 19.999%. "Stable" in this respect may also mean that the detected level variation is within the accuracy of a measurement. The accuracy of a measurement depends on the measurement method used. Preferably, the level is constant over time.

The time period between the first point in time and the later point(s) in time preferably amounts to at least 1 day, at least 2 days, at least 3 days, at least 4 days, at least 5 days, at least 6 days, at least 7 days (1 week), at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months (1 year), at least 24 months (2 years), at least 3 years, at least 4 years, at least 5 years, at least 6 years, at least 7 years, at least 8 years, at least 9 years, or at least 10 years. For example, the individual may be routinely checked, e.g. once or twice a year. The individual may be (re)tested at 2, 3, 4, 5, 6 7, 8, 9, or 10 time points (first point in time and further point(s) in time).

In addition to the determination of the course of a glioma, the treatment of this disease can be monitored. It is namely preferred that the individual receives or has received a treatment, in particular a therapeutic treatment, of a glioma during the determination of the course of a glioma. Thus, it is preferred that the individual receives or has received a therapeutic treatment of a glioma. Preferably,
 (i) the level of the at least one eIF which decreases over time indicates that the individual responds to said treatment,
 (ii) the level of the at least one eIF which does not change over time indicates that the individual does not respond to said treatment, or
 (iii) level of the at least one eIF which increases over time indicates that the individual does not respond to said treatment.

Therapeutic treatment of a glioma may be selected from the group consisting of the administration of a drug, chemotherapy, radiotherapy, and a combination thereof. The drug to be used in said therapeutic treatment may be selected from the group consisting of temozolomide, regorafenib, thalidomide, and bevacizumab. Preferably, the drug is selected from the group consisting of temozolomide and regorafenib.

The glioma is preferably a high-grade glioma (malignant), in particular a glioma of grades III or IV.

In the methods of the third to fourteenth aspect of the present invention, it is preferred that the sample is a biological sample, in particular a (tumor) tissue or a body fluid sample. It is also preferred that the reference sample is a reference biological sample, in particular a tumor tissue or a body fluid sample.

Preferably, the body fluid sample is selected from the group consisting of a blood sample, a urine sample, a lymph sample, a saliva sample and a combination thereof. More preferably, the blood sample is a whole blood sample or a blood fraction sample. Even more preferably, the blood fraction sample is a blood cell fraction sample, a blood serum sample, or a blood plasma sample.

Preferably, the aforementioned samples are pre-treated before they are used in the methods according to the third to fourteenth aspect of the present invention. Said pre-treatment may include treatments required to separate the at least one eIF described herein, or to remove excessive material or waste. Furthermore, pre-treatments may aim at sterilizing samples and/or removing contaminants such as undesired cells, bacteria or viruses. Suitable techniques comprise centrifugation, extraction, fractioning, ultrafiltration, protein precipitation followed by filtration and purification and/or enrichment of compounds. Moreover, other pre-treatments are carried out in order to provide the at least one eIF described herein in a form or concentration suitable for analysis.

In one embodiment of the methods according to the third to fourteenth aspect of the present invention, the sample used to determine the level of the at least one eIF can be a (tumor) tissue (obtainable e.g. by biopsy) or a body fluid. The body fluid is preferably whole blood, serum, lymph or saliva. The eIF markers of the present invention can be found in the tissue affected with the tumor and in body fluids like blood and blood components (e.g. serum), lymph and saliva.

According to another preferred embodiment of the methods according to the third to fourteenth aspect of the present invention, the level of the at least one eIF is determined by measuring mRNA or protein levels.

The levels of the eIFs in the methods according to the third to fourteenth aspect of the present invention can be determined either by measuring mRNA molecules encoding said eIFs or the eIFs as such in form of proteins. Methods to determine mRNA levels and protein levels in a sample are well known.

mRNA expression levels are usually measured by polymerase chain reaction (PCR), in particular by reverse transcription quantitative polymerase chain reaction (RT-PCR and qPCR) or real-time PCR. RT-PCR is used to create a cDNA from the mRNA. The cDNA may be used in a qPCR assay to produce fluorescence as the DNA amplification process progresses. This fluorescence is proportional to the original mRNA amount in the samples. Other methods to be used include Northern blots, Fluorescence in situ hybridization (FISH), microarrays, and RT-PCR combined with capillary electrophoresis.

Protein levels of eIFs are preferably determined using immunoassays. Such methods are based on the binding of an antibody, a derivative or a fragment thereof to its corresponding target (i.e. eIF). Polyclonal and monoclonal antibodies can be used in such methods. Derivatives or fragments of antibodies include Fab fragments, F(ab')$_2$ fragments, Fv fragments, single chain antibodies and single domain antibodies. Preferred immunoassays include Western blot, Immunohistochemistry, ELISA (enzyme-linked immunosorbent assay), radioimmunoassays, fluorescence resonance energy transfer (FRET) or time resolved-FRET (TR-FRET). Immunoassays detection is possible in lymphoma and HCC. Already for Westernblot used antibodies in the laboratory of the present inventors include, e.g., eIF-2a (Cell Signaling), eIF3c (Cell Signaling), eIF-4B (Cell Signaling), eIF-4G (Cell Signaling), 4E-BPT (Cell Signaling), eIF3b (Santa Cruz Biotechnology, INC.), eIF3d (Santa Cruz Biotechnology, INC.) and eIF-5 (GeneTex).

It is particularly preferred to use antibodies and derivatives or fragments of antibodies which have been obtained from a non-human source. These antigen binding molecules can be of porcine, rabbit, murine, camel or rat origin. Of course, it is also possible to use antibodies and derivatives or fragments thereof which are recombinantly produced in plants or cell cultures, in particular microbial cell cultures (e.g. bacteria, yeast).

In a fifteenth aspect, the present invention relates to a kit comprising means for determining the level of at least one eIF in a sample from an individual, wherein the at least one eIF is selected from the group consisting of.

(i) eIF1A and eIF6,
(ii) eIF6,
(iii) eIF1, eIF5, and eIF6,
(iv) eIF3I, eIF3M, eIF4A, eIF4H, eIF5, and eIF6,
(v) eIF3I, eIF4A, eIF4H, and eIF6,
(vi) eIF3I, eIF4H, eIF5, and eIF6,
(vii) eIF3I, eIF4G, and eIF4H,
(viii) eIF3D, eIF3H, eIF3I, eIF3J, eIF3K, eIF3M, eIF4A, eIF4B, preferably peIF4B, eIF4E, eIF4H, and eIF6, and/or
(ix) eIF2α, preferably peIF2α, eIF3D, eIF3H, eIF3I, eIF3J, eIF3K, eIF3M, eIF4A, eIF4B, preferably peIF4B, eIF4E, eIF4H, and eIF6.

In this respect, it should be noted that eIF4A preferably comprises the isoforms eIF4A1, eIF4A2, and/or eIF4A3. Further, eIF4E preferably comprises the isoforms eIF4ET, eIF4E2, and/or eIF4E3. Furthermore, eIF4G preferably comprises the isoforms eIF4G1, eIF4G2, and/or eIF4G3. In addition, peIF2α is the phosphorylated form of eIF2α and peIF4B is the phosphorylated form of eIF4B. peIF4B may also be designated as phoshpo-eIF4B.

As to the Gene IDs of the eIFs, it is referred to the first aspect of the present invention.

As to the specific (preferred) eIF combinations, it is referred to the third to fourteenth aspect of the present invention.

Said means may be primers or primer pairs allowing the detecting of the above mentioned eIFs on the RNA transcript, e.g. mRNA, level and/or antibodies, antibody derivatives or fragments of antibodies allowing the detection of the above mentioned eIFs on the protein level.

In addition, said means encompass dipstrips or dipsticks, e.g. urine or blood dipstrips or dipsticks. Said means are tools used to determine changes in individual's urine or blood. A dipstrip or dipstick comprises different chemical pads or reagents which react (e.g. change color, in particular by applying an immune assay) when immersed in (e.g. blood or urine), and then removed from the biological sample (e.g. urine or blood sample). The result can be read after a few minutes, preferably after a few seconds.

The kit is useful for conducting the methods according to the third to fourteenth aspect of the present invention. In particular, the kit comprising the eIFs referred to in
(i) (mentioned above) is useful for carrying out the method of diagnosing lung cancer in an individual,
(ii) (mentioned above) is useful for carrying out the method of providing a prognosis to an individual suffering from lung cancer,
(iii) (mentioned above) is useful for carrying out the method of diagnosing colorectal cancer in an individual, the method of differentiating between colon cancer (CC) and rectum cancer (RC) in an individual, the method of determining whether an individual responds to a therapeutic treatment of colorectal cancer, or the method of determining the course of colorectal cancer in an individual,
(iv) (mentioned above) is useful for carrying out the method of diagnosing a glioma in an individual,
(v) (mentioned above) is useful for carrying out the method of grading a glioma in an individual,
(vi) (mentioned above) is useful for carrying out the method of differentiating between a low-grade (benign) glioma and a high-grade (malignant) glioma in an individual,
(vii) (mentioned above) is useful for carrying out the method of providing a prognosis to an individual suffering from a glioma,
(viii) (mentioned above) is useful for carrying out the method of determining whether an individual (suffering from a glioma) responds to a therapeutic treatment of glioma, and/or
(ix) (mentioned above) is useful for carrying out the method of determining the course of a glioma in an individual.

The kit may further comprise
(i) a container, and/or
(ii) a data carrier.

Said data carrier may be a non-electronical data carrier, e.g. a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database. The access code may also allow access to an application software that causes a computer to perform tasks for computer users or a mobile app which is a software designed to run on smartphones and other mobile devices.

Said data carrier may further comprise a reference level of the at least one eIF referred to herein. In case that the data carrier comprises an access code which allows the access to a database, said reference level is deposited in this database.

In addition, the data carrier may comprise information or instructions on how to carry out the methods according to the third to fourteenth aspect of the present invention.

In a further aspect, the present invention relates to the use of at least one eIF selected from the group consisting of eIF1A and eIF6 for diagnosing lung cancer in an individual (suspected of having lung cancer).

In a further aspect, the present invention relates to the use of eIF6 for providing a prognosis to an individual suffering from lung cancer.

In a further aspect, the present invention relates to the use of at least one eIF selected from the group consisting of eIF1, eIF5, and eIF6 for diagnosing colorectal cancer in an individual (suspected of having colorectal cancer).

In a further aspect, the present invention relates to the use of at least one eIF selected from the group consisting of eIF1, eIF5, and eIF6 for differentiating between colon cancer (CC) and rectum cancer (RC) in an individual.

In a further aspect, the present invention relates to the use of at least one eIF selected from the group consisting of eIF1, eIF5, and eIF6 for determining whether an individual (suffering from colorectal cancer) responds to a therapeutic treatment of colorectal cancer.

In a further aspect, the present invention relates to the use of at least one eIF selected from the group consisting of eIF1, eIF5, and eIF6 determining the course of colorectal cancer in an individual (suffering from colorectal cancer).

In a further aspect, the present invention relates to the use of at least one eIF selected from the group consisting of eIF3I, eIF3M, eIF4A, eIF4H, eIF5, and eIF6 diagnosing a glioma in an individual (suspected of suffering from a glioma).

In a further aspect, the present invention relates to the use of at least one eIF selected from the group consisting of eIF3I, eIF4A, eIF4H, and eIF6 for grading a glioma in an individual (suffering from a glioma).

In a further aspect, the present invention relates to the use of at least one eIF selected from the group consisting of eIF3I, eIF4H, eIF5, and eIF6 for differentiating between a low-grade (benign) glioma and a high-grade (malignant) glioma in an individual.

In a further aspect, the present invention relates to the use of at least one eIF selected from the group consisting of eIF3I, eIF4G, and eIF4H for providing a prognosis to an individual suffering from a glioma.

In a further aspect, the present invention relates to the use of at least one eIF selected from the group consisting of eIF3D, eIF3H, eIF3I, eIF3J, eIF3K, eIF3M, eIF4A, eIF4B, preferably peIF4B, eIF4E, eIF4H, and eIF6 for determining whether an individual (suffering from a glioma) responds to a therapeutic treatment of glioma.

In a further aspect, the present invention relates to the use of at least one eIF selected from the group consisting of eIF2α, preferably peIF2α, eIF3D, eIF3H, eIF3I, eIF3J, eIF3K, eIF3M, eIF4A, eIF4B, preferably peIF4B, eIF4E, eIF4H, and eIF6 for determining the course of a glioma in an individual (suffering from a glioma).

In this respect, it should be noted that eIF4A preferably comprises the isoforms eIF4A1, eIF4A2, and/or eIF4A3. Further, eIF4E preferably comprises the isoforms eIF4E1, eIF4E2, and/or eIF4E3. Furthermore, preferably eIF4G comprises the isoforms eIF4G1, eIF4G2, and/or eIF4G3. In addition, peIF2α is the phosphorylated form of eIF2α and peIF4B is the phosphorylated form of eIF4B. peIF4B may also be designated as phoshpo-eIF4B.

As to the Gene IDs of the eIFs, it is referred to the first aspect of the present invention.

For the above mentioned uses, the level of the above mentioned eIFs is determined in a sample, in particular in a biological sample, from an individual to be tested. It is preferred that the biological sample is a body fluid sample or a (tumor) tissue sample. Preferably, the body fluid sample is selected from the group consisting of a blood sample, a urine sample, and a combination thereof. More preferably, the blood sample is a whole blood sample or a blood fraction sample.

Even more preferably, the blood fraction sample is a blood cell fraction sample, a blood serum sample, or a blood plasma sample. Most preferably, the biological sample is a blood plasma sample.

Regarding the specific (preferred) eIF combinations, it is referred to the third to fourteenth aspect of the present invention.

Test first and the second aspect of the present invention is summarized as follows:

1. A eukaryotic initiation factor (eIF) modulating compound for use in the treatment of a tumor.
2. Compound for the use according to embodiment 1, wherein the eIF modulating compound is selected from the group consisting of an eIF and an eIF inhibiting molecule.
3. Compound for the use according to embodiment 2, wherein an eIF inhibiting molecule is selected from the group consisting of an eIF binding molecule, a small interfering RNA (siRNA) and a short hairpin RNA (shRNA) for inhibiting expression of an eIF.
4. Compound for the use according to embodiment 3, wherein the eIF binding molecule is a polypeptide or a peptide comprising at least one eIF binding site.
5. Compound for the use according to embodiment 3 or 4, wherein the eIF binding molecule is an antibody or an antibody fragment binding to an eIF.
6. Compound for the use according to embodiment 5, wherein the antibody fragment is a Fab fragment, a F(ab')2 fragment, an Fv fragment or a scFv.
7. Compound for the use according to embodiment 1, wherein the eIF modulating compound is a nucleic acid molecule encoding an eIF.
8. Compound for the use according to embodiment 7, wherein the nucleic acid molecule is a DNA or RNA molecule.
9. Compound for the use according to embodiment 8, wherein the DNA molecule is comprised in an expression vector, preferably an expression plasmid.
10. Compound for the use according to any one of embodiments 1 to 9, wherein the eIF is selected from the group consisting of eIF1, eIF1A, eIF2AK3, eIF2AK4, eIF2B4, eIF2C 3, eIF2d, eIF-2a, eIF2S2, eIF3A, eIF3b, eIF3c, eIF3d, eIF3f, eIF3g, eIF3H, eIF3I, eIF3J, eIF3K, eIF3l, eIF3M, eIF4A, eIF-4B, eIF-4E, 4E-BP1, eIF-4G1, eIF4G, eIF4H, eIF-5A, eIF-5 and EIF6.
11. Compound for the use according to any one of embodiments 1 to 10, wherein the tumor is selected from the group consisting of lymphoma, glioma, colorectal carcinoma, hepatocellular carcinoma, cholangiocellullar carcinoma, pancreatic cancer and lung cancer.
12. Compound for the use according to any one of embodiments 1 to 11, wherein the compound is eIF-5 and/or a nucleic acid molecule encoding said eIF according to any one of embodiments 7 to 9 and the tumor to be treated is lymphoma, colorectal carcinoma, a glioma or hepatocellular carcinoma.
13. Compound for the use according to any one of embodiments 1 to 11, wherein the compound is eIF3M and/or a nucleic acid molecule encoding said eIF according to any one of embodiments 7 to 9 and the tumor to be treated is a glioma or colorectal carcinoma.
14. Compound for the use according to any one of embodiments 1 to 11, wherein the compound is eIF6 and/or a nucleic acid molecule encoding said eIF according to any one of embodiments 7 to 9 and the tumor to be treated is colorectal carcinoma, a glioma or hepatocellular carcinoma.
15. Compound for the use according to any one of embodiments 1 to 11, wherein the compound is selected from the group consisting of eIF3H, eIF3M, eIF4B, eIF4E, eIF4G, eIF5, eIF6, eIF1 and combinations thereof and/or a nucleic acid molecule encoding one or more of said eIF according to any one of embodiments 7 to 9 and the tumor to be treated is colorectal carcinoma.
16. Compound for the use according to any one of embodiments 1 to 11, wherein the compound is eIF2α, eIF5 or a combination thereof and/or a nucleic acid molecule encoding one or more of said eIF according to any one of embodiments 7 to 9 and the tumor to be treated is hepatocellular carcinoma.
17. Compound for the use according to any one of embodiments 1 to 11, wherein the compound is selected from the group consisting of eIF2AK3, eIF-4E3, eIF-5 and combinations thereof and/or a nucleic acid molecule encoding one or more of said eIF according to any one of embodiments 7 to 9 and the tumor to be treated is lymphoma.
18. Compound for the use according to any one of embodiments 1 to 11, wherein the compound is selected from the group consisting of eIF3A, eIF3B, eIF3C, eIF3I, eIF3M, eIF4A, eIF4H, eIF5, eIF6 and combinations thereof and/or a nucleic acid molecule encoding one or more of said eIF according to any one of embodiments 7 to 9 and the tumor to be treated is a glioma.

19. Compound for the use according to any one of embodiments 1 to 11, wherein the compound is selected from the group consisting of eIF1A, eIF3J, eIF3K, eIF6 and combinations thereof and/or a nucleic acid molecule encoding one or more of said eIF according to any one of embodiments 7 to 9 and the tumor to be treated is lung cancer.

20. Compound for the use according to any one of embodiments 1 to 11, wherein the eIF binding molecule and/or the shRNA and/or the siRNA for inhibiting expression of an eIF binds to or inhibits the expression of eIF2AK4, eIF2B4, eIF2C 3, eIF2d, eIF-2a, eIF2S2, eIF3b, eIF3c, eIF3d, eIF3f, eIF3g, eIF3l, eIF-4B, 4E-BP1, eIF-4G1 or eIF-5A and the tumor to be treated is lymphoma.

21. Compound for the use according to any one of embodiments 1 to 11, wherein the eIF binding molecule and/or the shRNA and/or the siRNA for inhibiting expression of an eIF binds to or inhibits the expression of eIF3A, eIF3B, eIF3C, eIF3I, eIF3M, eIF4A1, eIF4A2, eIF4A3, eIF5 or eIF6 and the tumor to be treated is a glioma.

22. Compound for the use according to any one of embodiments 1 to 11, wherein the eIF binding molecule and/or the shRNA and/or the siRNA for inhibiting expression of an eIF binds to or inhibits the expression of eIF1A, eIF3J, eIF3K or eIF6, preferably eIF1A or eIF6, and the tumor to be treated is lung carcinoma.

23. Compound for the use according to any one of embodiments 1 to 11, wherein the eIF binding molecule and/or the shRNA and/or the siRNA for inhibiting expression of an eIF binds to or inhibits the expression of eIF3H, eIF5 or eIF6 and the tumor to be treated is hepatocellular carcinoma.

24. Compound for the use according to any one of embodiments 1 to 11, wherein the eIF binding molecule and/or the shRNA and/or siRNA for inhibiting expression of an eIF binds to or inhibits the expression of eIF1, eIF3H, eIF3M, eIF4B, eIF4E, eIF4E2, eIF4E3, eIF4G1, eIF4G2, eIF4G3, eIF5 or eIF6 and the tumor to be treated is colorectal carcinoma.

25. Composition comprising at least one compound according to any one of embodiments 1 to 10 for use in the treatment of a tumor.

26. Composition according to embodiment 25, wherein said composition comprises pharmaceutically acceptable excipients.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

The present invention is further illustrated in the following figures, embodiments and examples, however, without being restricted thereto.

BRIEF DESCRIPTION OF THE FIGURES

FIGS. 7A-7L shows mRNA expression of eIFs in gliomas compared to non tumor controls (Ctrl) using qRT-PCR. eIF mRNA expression is represented in x-fold change to the non tumor control for eIF3A (FIG. 7A), eIF3B (FIG. 7B), eIF3C (FIG. 7C), eIF3I (FIG. 7D), eIF3M (FIG. 7E), eIF4A1 (FIG. 7F), eIF4E (FIG. 7G), eIF4EBP1 (FIG. 7H), eIF4G1 (FIG. 7I), eIF4H (FIG. 7J), eIF5 (FIG. 7K) and eIF6 (FIG. 7L). As housekeeping genes GAPDH and SDHA were used. Bars represent group means+SEM. Statistical analyses: One-way ANOVA followed by DUNN's or Bonferroni post-hoc test. Significance levels: $*p<0.05$; $p<0.01$, $*p<0.001$. Numbers: Control (Ctrl): n=7, grade I: n=7, grade II: n=9, grade III: n=6, grade IV: n=14.

FIGS. 9A-9E shows the immunohistochemical evaluation of eIF protein expression in astrocytomas (grade I-IV) compared to healthy control tissue. Graphs show the TIS of eIF3C (FIG. 9A), eIF4G (FIG. 9B), eIF4H (FIG. 9C), eIF5 (FIG. 9D) and eIF6 (FIG. 9E). Bars represent group means+SEM. Statistical analyses: One-way ANOVA followed by DUNN's post-hoc test. Significance levels: $*p<0.05$; $p<0.01$, $*p<0.001$. Numbers: Control: n=11, grade I: n=19, grade II: n=24, grade III: n=21, grade IV: n=13.

[FIG. 20A] Association of eIF2α expression with survival time in HCC. The eIF3h expression in HCC shows in patients with high score of eIF2α. [FIG. 20B] The eIF3h expression shows in patients with high score of eIF3h.

FIG. 21 shows Kaplan Meier Curves, in particular of HCC patients, to various eIFs. FIG. 21A shows the overall survival of patients with a score of 2 or 3 for eIF5 is better than with a score below 2. FIG. 21B Overall survival of patients with a high score of eIF6 is better than patients with a sore below 2 for eIF6.

FIGS. 22A-22B shows Kaplan Meier Curves, in particular of HCC patients, to various eIFs. [FIG. 22A] Association of eIF3p (eIF3c) expression with overall survival time in HCC patients. The eIF3p expression in HCC shows in 37 patients with high score of eIF3p, 37 patients represents a score below 3, 72 patients shows a score of 1 and no staining intensity for 88 patients. FIG. 22B Overall survival for eIF4e in patients with HCC. 19 patients with a high eIF4e expression level, 11 patients with a sore of 2, and 81 patients with a score of 1.

FIG. 23A shows IHC of eIF3 subunits in CRC, FIG. 23B shows protein expression of eIF3 subunits in CRC, and FIG. 23C shows mRNA expression of eIF3 subunits in CRC.

[FIGS. 24A and 24B] Significant upregulation on protein level for peIF4B, eIF4B and eIF4G in CRC samples compared to normal mucosa. eIF4E shows high expression in RC samples compared to normal mucosa. [FIG. 24C] Upregulation of eIF4B on mRNA level in CRC samples. Significant upregulation of eIF4G in RC samples. No changes of eIF4E on mRNA level. In particular, FIG. 24A shows IHC of eIF4 subunits in CRC, FIG. 24B shows protein expression of eIF4 subunits in CRC, and FIG. 24C shows mRNA expression of eIF4 subunits in CRC.

[FIGS. 25A and 25B] Significant upregulation on protein level for peIF2α and eIF2α in CC samples compared to RC and normal mucosa. Increase of eIF5 and eIF6 on protein level in CRC samples compared to normal mucosa. [FIG. 25C] Upregulation of eIF2α and eIF5 on mRNA level in RC samples. Significant increase of eIF6 on mRNA in CRC compared to normal mucosa. In particular, FIG. 25A shows IHC of, eIF2α and eIF6 in CRC, FIG. 25B shows Protein expression of p eIF2α, eIF2α, eIF5 and eIF6 in CRC, and FIG. 25C shows mRNA expression of eIF2α, eIF5 and eIF6 in CRC.

FIG. 29 shows polysomal profiles of eIF1, eIF5 and eIF6. [FIG. 26] Significant reduction of the protein expression after eIF1 silencing in HCT116 cells. Significant reduction of the mRNA expression after eIF1 silencing in HCT116 cells. Significant reduction of the cell viability after 24h, 48h and 72h of eIF1 silencing in HCT116 cells. Significant reduction of apoptosis after 24h, 48h and 72h of eIF1 silencing in HCT116 cells. [FIG. 27] Significant reduction of the protein expression after eIF5 silencing in HCT116 cells. Significant reduction of the mRNA expression after eIF5 silencing in HCT116 cells. Significant reduction of the cell viability after 24h, 48h and 72h of eIF5 silencing in HCT116 cells. Significant reduction of apoptosis after 24h, 48h and 72h of eIF5 silencing in HCT116 cells. FIG. 28 Significant reduction of the protein expression after eIF6 silencing in HCT116 cells. Significant reduction of the mRNA expression after eIF6 silencing in HCT116 cells. Significant reduction of the cell viability after 24h, 48h and 72h of eIF6 silencing in HCT116 cells. Significant reduction of apoptosis after 24h, 48h and 72h of eIF6 silencing in HCT116 cells. [FIGS. 29A-29C] Polysome associated fraction analysis of eIF1, eIF5 and eIF6. Polysomal profiles of HCT116 cells transfected with eIF1 (Si eIF1) and control (MOK). Increased formation of functional 60S and reduced 80S ribosomes recorded after knockdown of eIF1. Polysomal profiles of HCT116 cells transfected with eIF5 (Si eIF5) and control (MOK). Increased formation of functional 40S and 60S ribosomes recorded after knockdown of eIF5. Polysomal profiles of HCT116 cells transfected with eIF6 (Si eIF6) and control (MOK). Increased formation of functional 40S and 60S and reduced 80S ribosomes recorded after knockdown of eIF6.

FIG. 30A shows the effect of eIF1 knockdown on invasiveness and clonogenicity in HCT 116 cells, and FIG. 30B shows the effect of eIF5 knockdown on invasiveness and clonogenicity in HCT 116 cells. Clonogenicity is dramatically reduced after eIF1 knockdown in HCT 116 cells compared to the scrambled control cell. Clonogenicity is dramatically reduced at all three time points after eIF5 knockdown in HCT 116 cells compared to the scrambled control cell.

FIG. 33 shows single eIFs and a set of eIFs which level is preferably determined in a method of diagnosing a lung cancer in an individual.

FIG. 34 shows single eIFs and sets of eIFs which level is preferably determined in a method of diagnosing a glioma in an individual. These sets comprise 3, 4, 5, or 6 eIFs.

FIGS. 37A-37R shows eIF protein expression in murine xenograft models after chemosensitivity testings. The effect of Everolimus (FIG. 37B), Sorafenib (FIG. 37C), Bevacizumab (FIG. 37D), Irinotecan (FIG. 37E), Salinomycin (FIG. 37F) and Temozolomide (FIG. 37G) on eIF protein expression was analyzed in comparison to the PBS control group (FIG. 37A) using immunoblot analyses. Six different murine xenograft models were investigated (X5, X6, X7, X8, X9, X11). In all xenograft models except for X5, Temozolomide drastically reduced tumor growth. Densitometric analyses of immunoblots were performed using ImageJ software (NIH, MD, United States). For relative densities, expression of eIF1A (FIG. 37a), p-eIF2α (FIG. 37b), eIF2α (FIG. 37c), eIF3A (FIG. 37d), eIF3B (FIG. 37e), eIF3C (FIG. 37f), eIF3D (FIG. 37g), eIF3H (FIG. 37h), eIF3I (FIG. 37i), eIF3J (FIG. 37j), eIF3K (FIG. 37k), eIF3M (FIG. 37l), eIF4A (FIG. 37m), p-eIF4B (FIG. 37n), eIF4E (FIG. 37o), eIF4G (FIG. 37p), eIF4H (FIG. 37q) und eIF6 (FIG. 37r) was normalized to the loading control (Actin). Scatter dot blot+SEM. Statistical analysis: 1-way ANOVA with Bonferroni posttest ($*p<0.05$; $**p<0.01$).

FIGS. 38A-38O shows eIF protein expression in murine xenograft models after chemosensitivity testings using either monotherapies or combination therapies. The effect of Temozolomide (FIG. 38B), Thalidomide (FIG. 38C), Temozolomide/Thalidomide (FIG. 38D), Everolimus (FIG. 38E), Temozolomide/Everolimus (FIG. 38F), Regorafenib (FIG. 38G) und Temozolomide/Regorafenib (FIG. 38H) on eIF protein expression was analyzed in comparison to the PBS control group (FIG. 38A) using immunoblot analyses. Two different murine xenograft models were investigated (X3, X4). Densitometric analyses of immunoblots were performed using ImageJ software (NIH, MD, United States). For relative densities, expression of p-eIF2α (FIG. 38a), eIF2α (FIG. 38b), eIF3A (FIG. 38c), eIF3B (FIG. 38d), eIF3H (FIG. 38e), eIF3I (FIG. 38g), eIF3J (FIG. 38h), eIF3K (FIG. 38i), eIF3M (FIG. 38j), eIF4A (FIG. 38k), p-eIF4B (FIG. 38l), eIF4E (FIG. 38m), eIF4G (FIG. 38n) und eIF4H (FIG. 38o) was normalized to the loading control (Actin). Scatter dot blot+SEM. Statistical analysis: 1-way ANOVA with Bonferroni posttest ($*p<0.05$; $**p<0.01$)

EXAMPLES

Figure 1:
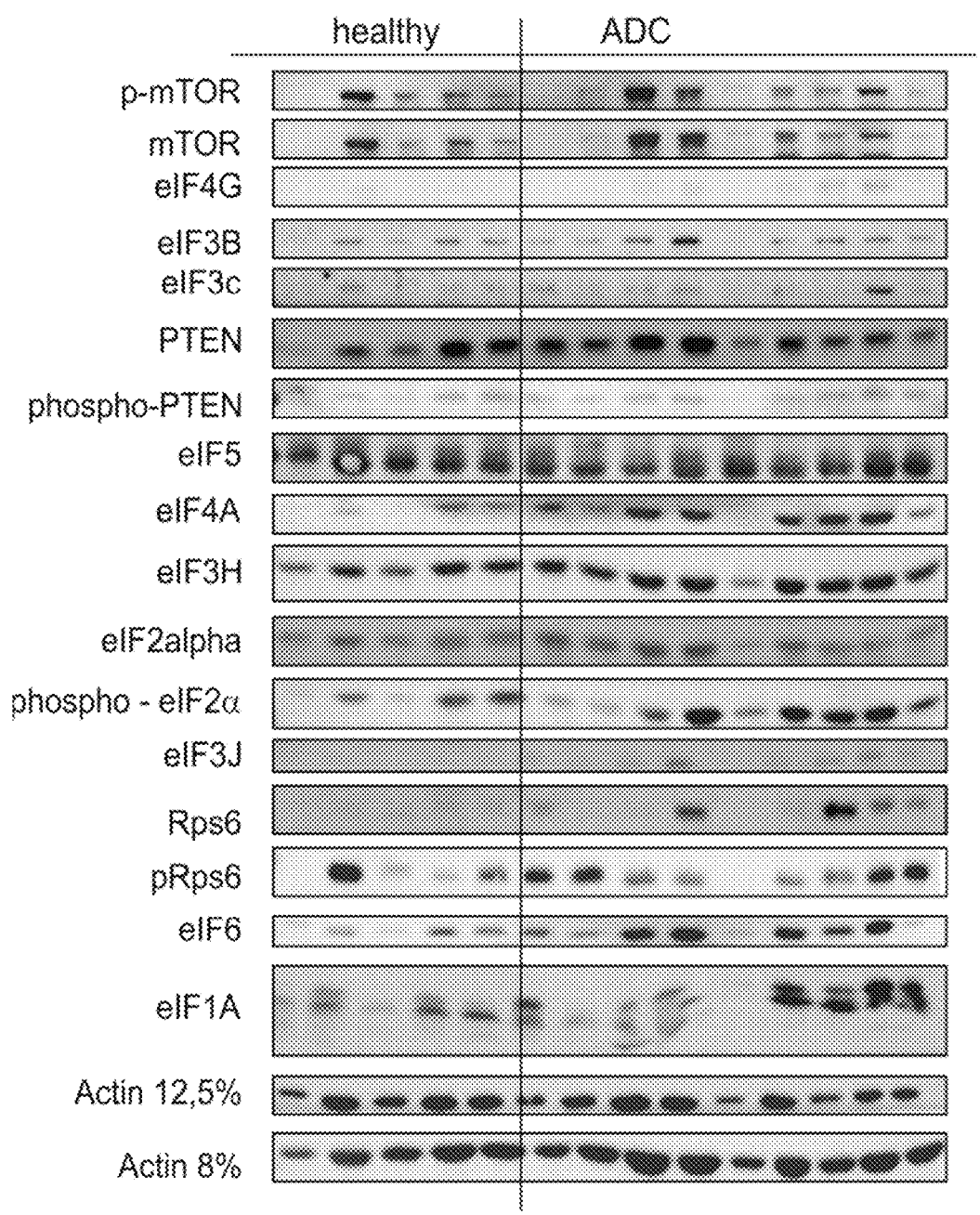
FIG. 1 shows protein expression levels of eIFs and mTOR pathway members in adenocarcinoma (lung cancer) samples compared to healthy tissue samples. eIF6 and eIF1A are upregulated in adenocarcinoma tissue compared to healthy lung tissue.

Materials & Methods
Immunoblot Analyses

Protein expression was analyzed in NP-40 tissue lysates. Therefore normalized protein amounts were loaded onto 8% or 12.5% polyacrylamide gels in consideration of the molecular mass of the protein of interest. Electrophoresis was performed for 1.5 h at 120 V in SDS Running Buffer with the Mini-vertical electrophoresis unit (Amersham Biosciences). Then separated proteins were transferred to PVDF-membranes (Immobilin-P Transfer Membran; Millipore) using a Semi Dry Blotting Unit (JH BioInnovations) at 160 mA for 1.5 hours. Membranes were blocked with 5% non-fat dried milk (AppliChem) in Tris-buffered saline- Tween (TBS-T; 0.2 M Tris, 1.4 M NaCl, pH 7.4, 0.1% Tween) for 1 h, followed by a primary antibody incubation (overnight at 4° C.) and an 1 h secondary antibody incubation (1:3000 dilution, GE Healthcare). All primary antibodies were diluted in 5% bovine serum albumin diluted in TBS-T. Between incubation steps membranes were washed 3 times in TBS-T for 10 min. Membranes were then developed with an enhanced chemiluminescence (ECL) Western blotting system (GE healthcare) using the ChemiImager™ System (Alpha Innotech). Immunoblots were evaluated semi-quantitative using ImageJ (Schneider C A, et al. Nat Meth. 9(2012):671-5) software for densitometric analyses. Relative densities were then calculated by normalizing density values for each protein to the loading control (Actin).

TABLE 1

Primary antibodies used for immunoblot analyses

| Primary Antibody | Manufacturer | Dilution |
| --- | --- | --- |
| eIF1A | Abcam | 1:10000 |
| eIF2α (D7D3) XP | Cell Signaling | 1:1000 |
| Phospho-eIF2α (Ser51)(D9G8) | Cell Signaling | 1:1000 |
| eIF3A | Cell Signaling | 1:1000 |
| eIF3B (=eIF3η (D-9)) | Santa Cruz | 1:1000 |
| eIF3C | Cell Signaling | 1:1000 |
| eIF3D (=eIF3ζ (H-300)) | Santa Cruz | 1:1000 |
| eIF3H (D9C1) XP | Cell Signaling | 1:1000 |
| eIF3J | Cell Signaling | 1:1000 |
| eIF3K (2313C2a) | Santa Cruz | 1:1000 |
| eIF3M | Santa Cruz | 1:1000 |
| eIF3Q (H-300) | Santa Cruz | 1:200 |
| eIF3θ (H-300) | Santa Cruz | 1:1000 |
| eIF4A1 | Cell Signaling | 1:1000 |
| eIF4B | Cell Signaling | 1:1000 |
| Phospho-eIF4B | Cell Signaling | 1:1000 |
| eIF4E | Cell Signaling | 1:1000 |
| eIF4G | Cell Signaling | 1:1000 |
| eIF4H | Cell Signaling | 1:1000 |
| eIF5 | Gene Tex | 1:1000 |
| eIF6 | Cell Signaling | 1:1000 |

RNA Isolation and qRT-PCR

Total RNA was isolated from deep-frozen brain tissue using Trizol reagent (Life Technologies). Tissue pieces were homogenized in 1 ml Trizol for 30 seconds at 6500 rpm with the MagNA Lyser (Roche). The lysate was incubated for 10 minutes at RT. Next, 200 µl chloroform were added, mixed, incubated for 3 minutes at RT and centrifuged at 10 000 rpm for 15 minutes at 4° C. The upper phase containing the RNA was carefully transferred into a fresh tube, mixed with 500 µl isopropanol and again centrifuged at 10 000 rpm for 20 minutes at 4° C. The supernatant was discarded and the pellet washed with 1 ml 75% ethanol. The pellet was then dried at 37° C. to completely remove the ethanol and then dissolved in 100-200 µl DEPC treated water at 58° C. RNA concentration and quality were determined with the Nano-Drop 1000 Spectrophotometer (PeqLab) and subsequently 1 µg RNA is transcribed from total RNA with the High-Capacity cDNA Reverse Transcription Kit (Applied Biosystems) according to the manufacturer's instructions.

The obtained cDNA was used for quantitative real time RT-PCR (qRT-PCR) using the 7900HT Fast Real-Time PCR System cycler (Applied Biosystems). Oligonucleotides were self-designed using Primer-BLAST software (10) and synthesized by Eurofins Genomics. Efficiencies of all self-designed primers were calculated with known cDNA concentrations. For the qRT-PCR reaction the Power SYBR® Green PCR Master Mix (Life technologies) is used. Parameters for the qRT-PCR program are set according to the manuals. Threshold cycles (C(t)) were automatically calculated by the 7900HT Fast Real-Time PCR System software (Applied Biosystems). Relative RNA expression was evaluated using the $\Delta\Delta C(t)$-method.

Tissue Microarrays (TMA)

All tumor tissue samples were acquired at the time of surgery and immediately frozen in liquid nitrogen and stored at −80° C.

Every sample was stained for haematoxylin-eosin and examined to determine relevant tumor areas which were marked on the slide. Tissue cones of the chosen tumor regions were punched out, assembled in an array structure and embedded into a fresh paraffin block, according to a specific pattern. The sections taken were 5 µm thick, mounted on a specific adhesive-coated glass slide, compatible for immunohistochemical staining and analysis.

Immunohistochemistry (IHC)

A summary of all used antibodies and the dilution to determine the expression of different eIFs is shown in Table 2. Staining was performed using the Ventana Immunostainer XT (Ventana Medical Systems, USA). The endogenous peroxidase activity was inactivated in 3% hydrogen peroxide for 5 minutes. The primary antibodies were applied at different dilutions (Table 1) for 60 minutes, followed by incubation with a peroxidase-labelled secondary antibody for 30 minutes and substrate-chromogen 3.3'-diaminobenzidine tetrahydrochloride for 8 minutes. Counterstaining was performed with haematoxylin.

The intensity of IHC staining was evaluated by light microscopy. Density and intensity of each TMA spot was scored in a semi-quantitative manner by differentiating nuclear and cytoplasmic staining. The Total Immunostaining Score (TIS) was calculated in percent. No staining was termed as 0, weak staining as 1, moderate staining as 2 and strong staining as 3.

TABLE 2

Primary antibodies used for immunohistochemistry

| Primary Antibody | Company | Dilution | Second Antibody |
| --- | --- | --- | --- |
| Phospho-mTOR | Cell Signalling (#5536) | 1:1000 | Rabbit |
| mTOR | Cell Signalling (#2983) | 1:1000 | Rabbit |
| Phospho-PTEN | Cell Signalling (#9551) | 1:1000 | Rabbit |
| PTEN | Cell Signalling (#9559) | 1:1000 | Rabbit |
| Phospho-P70S6K | Cell Signalling (#9204) | 1:1000 | Rabbit |
| P70S6K | Cell Signalling (#9202) | 1:1000 | Rabbit |
| Phospho Akt | Cell Signalling (#4058) | 1:1000 | Rabbit |
| Akt | Cell Signalling (#9272) | 1:1000 | Rabbit |
| GAPDH | Cell Signalling (#2118) | 1:3000 | Rabbit |
| Phospho 4E-BP1 | Cell Signalling (#9456) | 1:1000 | Rabbit |
| 4E-BP1 | Cell Signalling (#9452) | 1:1000 | Rabbit |
| Anti-Actin | Sigma (A2103) | 1:1000 | Rabbit |

TABLE 2-continued

Primary antibodies used for immunohistochemistry

| Primary Antibody | Company | Dilution | Second Antibody |
|---|---|---|---|
| eIF1 | Sigma (HPA043003) | 1:500 | Rabbit |
| Phospho-eIF2α (Ser51)(D9G8) | Cell Signalling (#3398) | 1:1000 | Rabid |
| eIF2α (D7D3) XP | Cell Signalling (#5324) | 1:1000 | Rabbit |
| eIF3A | Cell Signalling (#2538) | 1:1000 | Rabbit |
| eIF3β(A-8) = eIF3I | Santa Cruz (sc-374155) | 1:1000 | Mouse |
| eIF3C | Cell Signalling (#2068) | 1:1000 | Rabbit |
| eIF3H (D9C1)XP | Cell Signalling (#3413) | 1:1000 | Rabbit |
| eIF3J | Cell Signalling (#3261) | 1:1000 | Rabbit |
| eIF3K (2313C2a) | Santa Cruz (sc-81262) | 1:1000 | Mouse |
| eIF3M (V-21) | Santa Cruz (sc-133541) | 1:500 | Rabbit |
| eIF3B = eIF3ηD-9 | Santa Cruz (sc-137215) | 1:1000 | Mouse |
| eIF3P110 (B-6) | Santa Cruz (sc-74507) | 1:500 | Mouse |
| eIF3θ (H-300) | Santa Cruz (sc-30149) | 1:1000 | Rabbit |
| eIP3ζ (H-300) = eIF3D | Santa Cruz (sc-28856) | 1:1000 | Rabbit |
| Phospho eIF4b (Ser406) | Cell Signalling (#5399) | 1:1000 | Rabbit |
| eIF4B | Cell Signalling (#3592) | 1:1000 | Rabbit |
| eIF4E | Cell Signalling (#9742) | 1:1000 | Rabbit |
| eIF4G | Cell Signalling (#2498) | 1:1000 | Rabbit |
| eIF5 | GeneTex (GTX114923) | 1:500 | Rabbit |
| eIF6 | GeneTex (GTX63642) | 1:1000 | Rabbit |

Generation of Xenograft Models

Samples of patients suffering from colon cancer or GBMs were transplanted into 3 to 6 immunodeficient NOD/SCID mice. The tumor growth was monitored in a daily rhythm. At a size of about 1 cm$^3$, the tumors were removed and transferred to naive NMRI:nu/nu mice for chemosensitivity testing. Xenotransplanted carcinomas and metastases were treated with different standard and novel chemotherapeutic drugs. During chemosensitivity testing the tumor volume was measured regularly and used to generate growth curves. After a time period of 30-40 days the tumors were excised and analyzed by Immunoblot and Real-Time-PCR. Chemosensitivity data were kindly provided by EPO Berlin-Buch GmbH. Tumor volume of treatment in comparison to control (T/C) was calculated in percent.

Cell Culture siRNA transfection in: We targeted the gene of interest by using small interfering RNAs (siRNAs) from QIAGEN (Hilden, Germany). For each gene of interest, two target sequences were used. For eIF1; 5'-GACCAGA-CATATCCTAGCTAA-3' (SEQ ID NO: 1) and 5'-AAGCAATACCGTCATGTTTCA-3' (SEQ ID NO: 2), for eIF5; 5'-AGGCGCTTAATCGGCCTCCAA-3' (SEQ ID NO: 3) and 5'-CAGCCAGAAGTGCAACATGTA-3' (SEQ ID NO: 4); for eIF6; 5'-CTGCTTTGCCAAGCTCACCAA-3' (SEQ ID NO: 5) and 5'-CTGGTGCATCCCAA-GACTTCA-3' (SEQ ID NO: 6). For eIF3I: 5'-ATAAAT-TGGTTTGGTAATAAA-3' (SEQ ID NO: 7) and 5'-AAGGACCCTATCGTCAATGTA-3'(SEQ ID NO: 8). For eIF1AX; 5'-CCGAGACTACCAGGATAACAA-3' (SEQ ID NO: 9) and 5'-ATCAATGAAACTGATACATTT-3' (SEQ ID NO: 10).

Transfection experiments for: Were performed using MetafecteneRsi+transfection reagent (Biontex, Munich, Germany) according to manufacturer's instructions. For the transfection, 1×SI buffer, Metafectene SI+ and siRNA were mixed into a drop. After an incubation of 15 min at room temperature 500 μl cells (80 000 cells/well) were seeded onto a 24-well plate. Cells with transfection mix were cultured at 37° C. in a humidified atmosphere of 5% CO$_2$. The cells were collected after incubation for 24h, 48h and 72h.

Proliferation Assay for: Transfected cells and MOK were seeded in 96-well plates (80 000 cells/well) and cultivated under low serum conditions (1% FCS) for 24h, 48h and 72h. Viable cell number was determined on the basis of mitochondrial conversion of 3-(4,5-dimethylthiazol-2-yl)-2,5-diphenyltetrazolium bromide (MTT, Sigma Aldrich, Missouri, USA) to formazine. Cells were incubated with MTT for 2h at 37° C., the medium supernatant was removed and the cells were lysed with sodium dodecyl sulfate for 15 min at room temperature. The MTT formazan crystals were resolved with isopropanol/HCl under shaking for 15 min at room temperature. Optical density was measured at 570 nm (SynergyTM4, BioTek, Winooski, USA). Each assay was executed in six-fold determination and three independent experiments were performed.

Apoptosis for: Apoptotic cells were detected using YO-PRO®-1 (Thermo Fisher Scientific, Massachusetts, USA) reagent. siRNA-transfected and control cells were seeded onto 96-well plates (80 000 cells/well). After 24h, 48h and 72h, cells were incubated with YO-PRO®-1 for 15 min at 37° C., the supernatant was removed, cells were washed with PBS and then measured 485 nm to 535 nm. Each assay was performed in six-fold determination and three independent experiments were carried out.

Invasion Assay for: For analysis of invasiveness of CRC cells, the CytoSelect™ 24-Well Cell Invasion Assay (Cell Biolabs, USA) was used according to the manufacturer's instructions. 1×10$^5$ siRNA transfected cells and control cells were suspended in medium with 10% FCS, placed in the upper chamber and incubated for 48h at 37° C. The cells that had invaded to the lower surface of the filter inserts were stained with crystal violet. The optical density was measured at 560 nm (SynergyTM4, BioTek, USA).

Colony forming assay for: cells transfected with siRNA and scrambled siRNA as control were collected and seeded in six-well plates at a density of 500 cells/well. The medium was changed every three days. After two weeks of culture, cells were washed three times with PBS and fixed in 4% paraformaldehyde (Sigma-Aldrich, Missouri, USA). Fixed cells were stained by adding freshly prepared diluted Giemsa solution (Sigma-Aldrich, USA) for 20 min. Then the cells were rinsed with distilled water and colonies were analysed using a microscope (Nikon™S—Inverted Microscope, Japan).

Sucrose-gradient fractionation, polysome associated fraction analysis: Sucrose density-gradient centrifugation was used to analyzed the cellular distribution of polysomes, 80S ribosomes and free 40S and 60S subunits. Cells were cultured in 100 mm dishes and transfected with siRNA and control for 24h, 48h and 72h. 15 minutes prior to lysis, cells were incubated with 100 μg/ml cycloheximide (Sigma-Aldrich, Missouri, USA) to stall ribosomes on the mRNA strand. Lysis was performed on ice by washing cells in ice-cold PBS containing 100 μg/ml cycloheximide followed by suspension in lysis buffer (20 mM HEPES pH 7.4, 15 mM $MgCl_2$, 200 mM KCl, 1% Triton X-100, 2 mM DTT and 100 μg/ml cycloheximide), and nuclei were removed by centrifugation (14000g, 10 min, 4° C.). The supernatant was layered onto 15%-40% sucrose gradients (50 mM NH4Cl, 50 mM Tris-acetate pH 7.0, 12 mM $MgCl_2$, 100 μg/ml cycloheximide and freshly added 1 mM DTT) and centrifuged in a SW41Ti rotor (Beckman, Villepinte, France) for 150 min at 160000g, 4° C. without breaking. Polysomal profiles were analysed via an ISCO density gradient analyser unit, which analyses and simultaneously blots ribosomal distribution measured by an UA6 detector with 254 nm filter (Teledyne ISCO, Nebraska, USA).

All fractions were TCA (Trichloroacetic acid) precipitated over night at −20° C. to concentrate proteins for gel electrophoresis.

Statistical Analysis

All values are represented as means±standard error of the mean if not indicated otherwise. Statistical significance was evaluated using one-way ANOVA followed by the Bonferroni's multiple comparison tests. All calculations were performed using GraphPad Prism software (La Jolla, USA).

Example 1: Lung Cancer

Non Small Cell Lung Cancer (NSCLC) is among the most frequently diagnosed cancer entities and is the leading cause of cancer related death worldwide. In recent years, protein synthesis has turned out to be tightly linked to cancer. Translating mRNA to the corresponding protein is one of the major activities in each cell and is a strictly regulated process. Crucial for this translation process are eukaryotic initiation factors (eIFs), which are themselves regulated by the mammalian target of Rapamycin (mTOR)-pathway. Dysregulation of translation initiation may lead to alterations in protein synthesis resulting in uncontrolled cell growth and cancer formation. Thus, eIFs represent crossroads for carcinogenesis.

Methods

Paired NSCLC and Non Neoplastic Lung Tissue (NNLT) from 28 individuals were studied on protein expression level for eIFs and mTOR pathway members by Immunoblot analyses. qRT-PCR As housekeeping gene (HKG) for adenocarcinoma a combination of importin 8(IPO8) and succinate dehydrogenase A (SDHA) was used. For squamous cell carcinoma succinate dehydrogenase A (SDHA) and beta actin was used. Therefore the mean of the C(t) values of both HKGs was calculated and used for the ΔΔC(t))-calculation.

Transfection of A549

Carcinoma cell line A549 was transfected with Oligofectamin™ tranfection reagent form Invitrogen. Cells were transfected according to manufacturer's instructions. Cells were serum straved 24h before seeding in 12 well plates. We seeded 20.000 cell per well and transfected them after 24h. Cells with tranfection solution were cultured at 37° C. in a humidified atmosphere of 5% $CO_2$. The cells were collected after incubation for 72h and 120h.

For A549 we used small interfering RNAs (siRNAs) from QIAGEN (Hilden, Germany). For each gene of interest, two target sequences were used. For eIF6; 5'-CTGCTTTGC-CAAGCTCACCAA-3'(SEQ ID NO: 5) and 5'-CTGGTG-CATCCCAAGACTTCA-3' (SEQ ID NO: 6). For eIF1AX; 5'-CCGAGACTACCAGGATAACAA-3' (SEQ ID NO: 9) and 5'-ATCAATGAAACTGATACATTT-3' (SEQ ID NO: 10).

Proliferation Measurements

A549 viable cells were counted at 72h and 120h with Guava ViaCount Reagent for Flow Cytometry from Merck Millipore according to manufacturer's instructions.

Apoptosis Measurements

Apoptosis in eIF silenced A549 cells were measured with Annexin V: FITC Apoptosis Detection Kit I from Becton Dickinson Austria GmbH according to manufacturer's instructions, at 72h and 120h.

Affimetrix Data Analysis

The gene expression data of eIF6 in NSCLC, ADC and SQC were downloaded from RMA (Robust Multi-Array Average) normalized counts from Affymetrix platform for NSCLC on 20 Feb. 2017. The number of NSCLC was 1926 patients, for ADC 720 patient and for SQC 524 patients. The patient survival data was also obtained from Affimetrix data set and analyzed with log-rank test. To analyze the association between gene expression (stratified by median) and survival gene expression values were used in all cancer types.

Immunohistochemistry of eIF6

Immunohistochemistry on an adenocarcinoma (ADC) and squamous cell carcinoma (SQCC) tissue microarray (TMA) was performed. Following antibody was used in a 1:100 dilution, eIF6 Antibody, Bethyl, A303-030A.

Results

Adenocarcinoma

Figure 3:
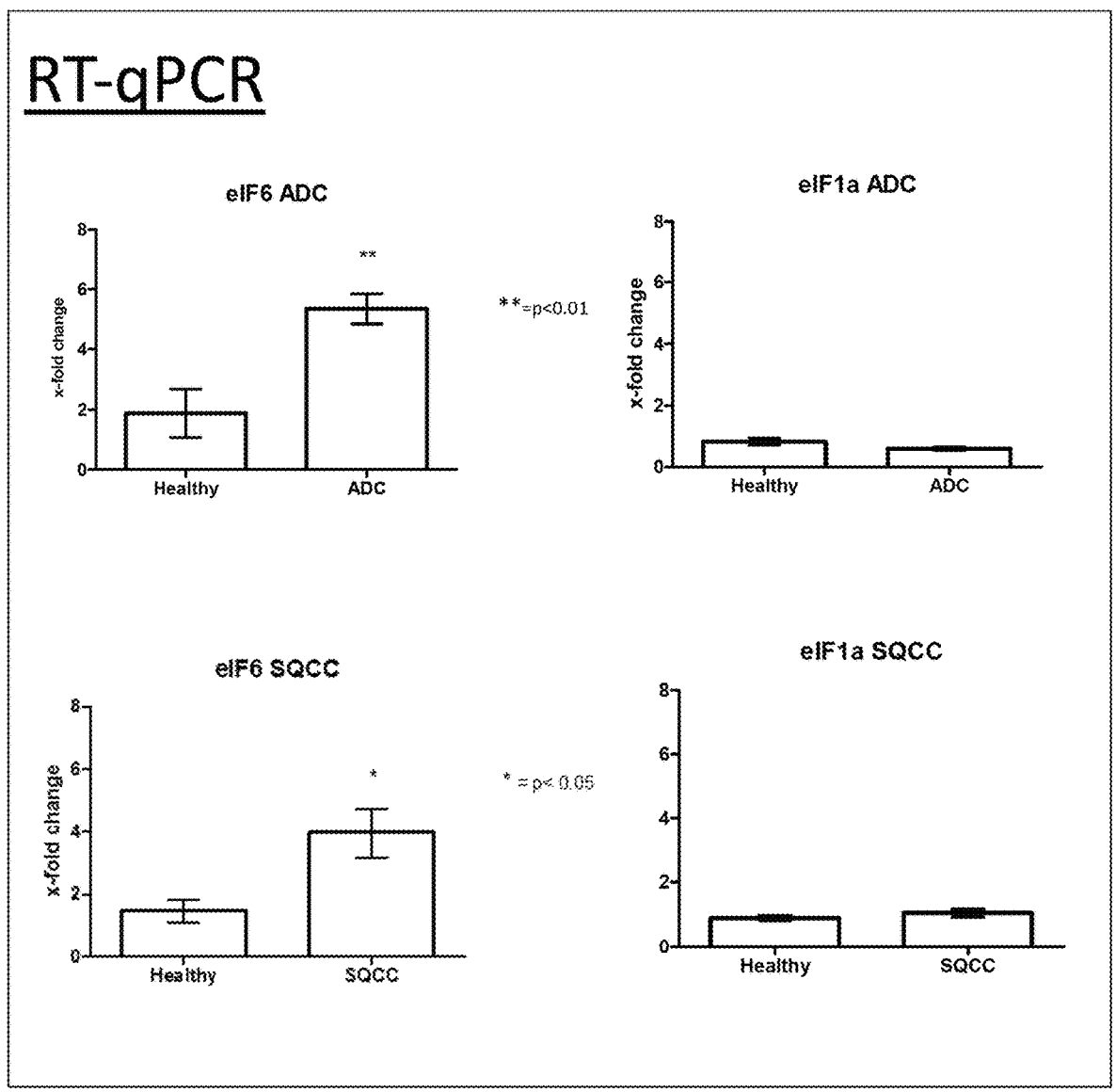
FIG. 3 shows mRNA expression levels of eIFs in adenocarcinoma and squamous cell carcinoma (lung cancer) samples compared to healthy tissue samples using qRT-PCR. The mRNA levels of eIF6 are upregulated in tumor tissue compared to healthy control. eIF1A is not altered in tumor samples compared to healthy controls.

In FIG. 1 a basic characterization of eIFs and mTOR pathway members in 9 adenocarcinoma patients is shown. The factors eIF1A, eIF6 and eIF4A are upregulated compared to healthy lung tissue. This finding is not described in literature. In FIG. 3 mRNA levels of eIF6 and eIF1A was investigated in adenocarcinoma (ADC) patients. The mRNA levels of eIF6 are upregulated in tumor tissue compared to healthy control. eIF1A is not altered in tumor samples compared to healthy controls.

Immunohistochemistry data from an ADC TMA show that eIF6 is significantly (p>0,001) upregulated in ADC patient tissue (n=307) compared to healthy parenchymal tissue (n=156) (data not shown).

Squamous Cell Carcinoma

Figure 2:
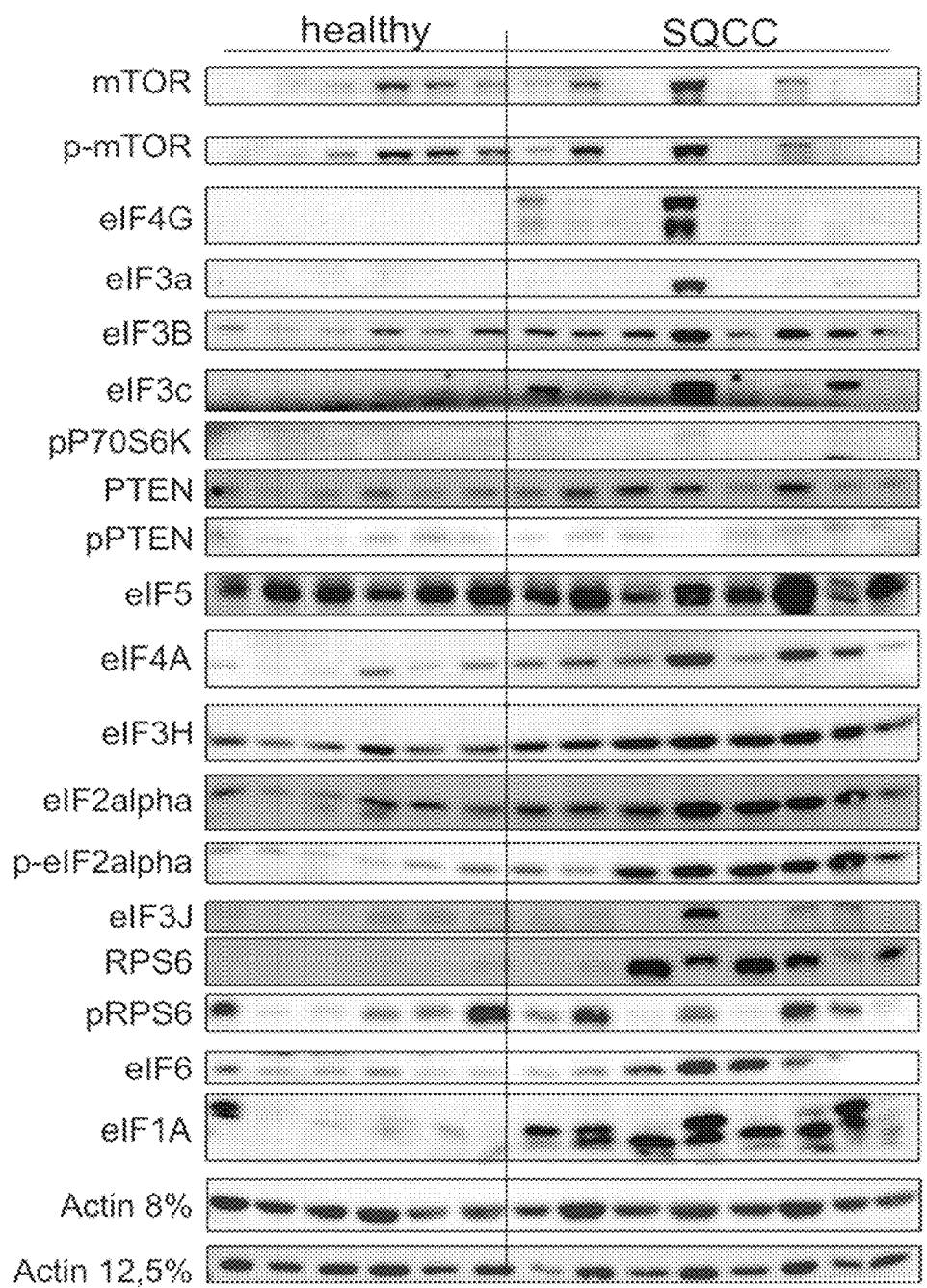
FIG. 2 shows protein expression levels of eIFs and mTOR pathway members in squamous cell carcinoma (lung cancer) samples compared to healthy tissue samples. The factors eIF1A, eIF6 and eIF4A are upregulated in squamous cell carcinoma compared to healthy lung tissue.

In FIG. 2 a basic characterization of eIF protein expression levels in squamous cell carcinoma patients is shown. eIFs are altered in squamous cell carcinoma tissue compared to non neoplastic tissue (FIG. 2). The factors eIF1A, eIF4A, Rps6 and eIF6 are upregulated which is a new finding. In FIG. 3 mRNA levels of eIF6 and eIF1A was investigated in squamous cell carcinoma (SQCC) patients. The mRNA levels of eIF6 are upregulated in tumor tissue compared to healthy control. eIF1a is not altered in tumor samples compared to healthy controls.

Immunohistochemistry data from a SQCC TMA show that eIF6 is significantly (p>0,001) upregulated in SQCC patient tissue (n=61) compared to healthy parenchymal tissue (n=31) (data not shown).

Knock Down of eIF6 and eIF1A

Figure 4A:
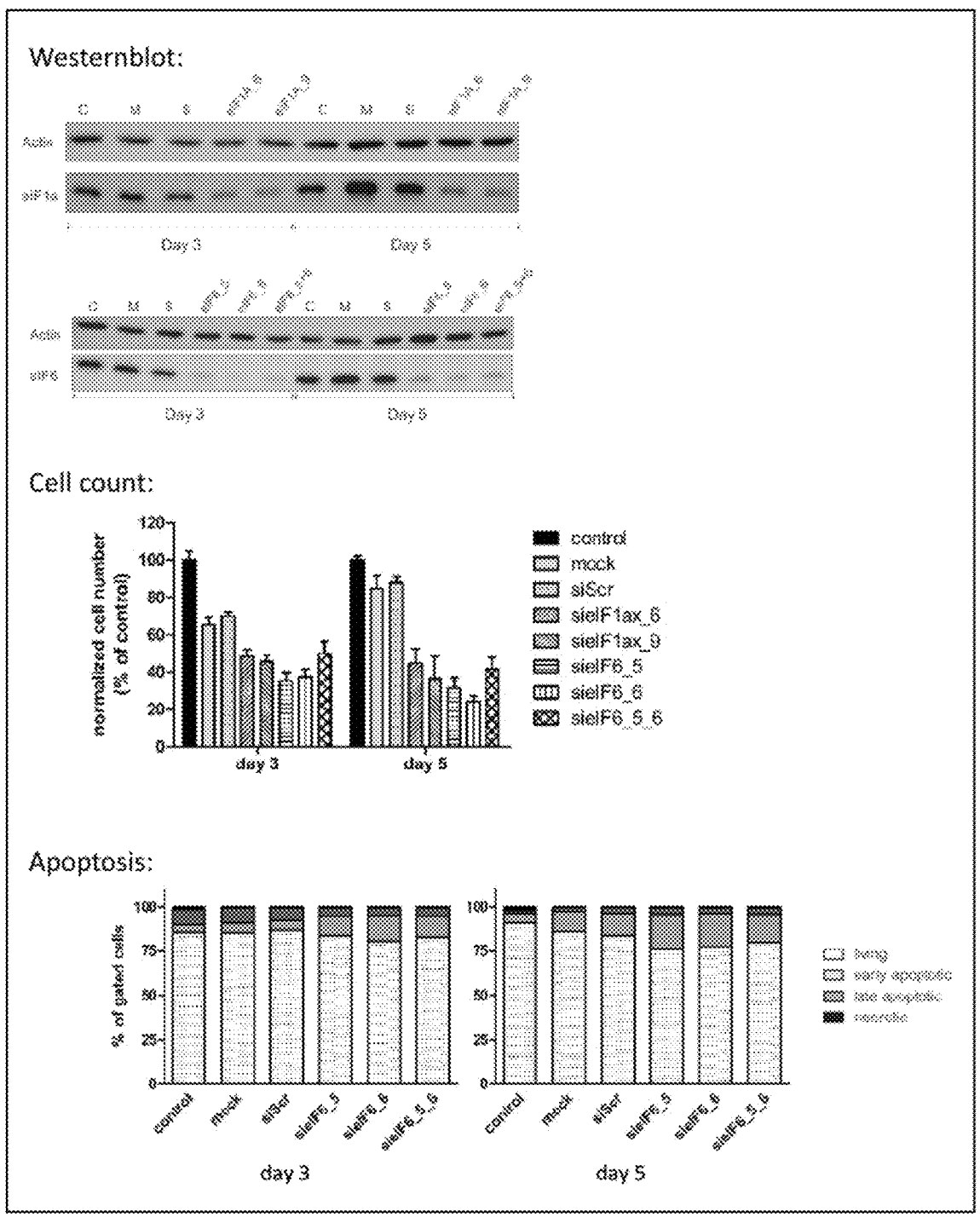
FIG. 4A shows silencing experiments in lung carcinoma cell line A549, where eIF6 and eIF1aX were knocked down.
Figure 4B:
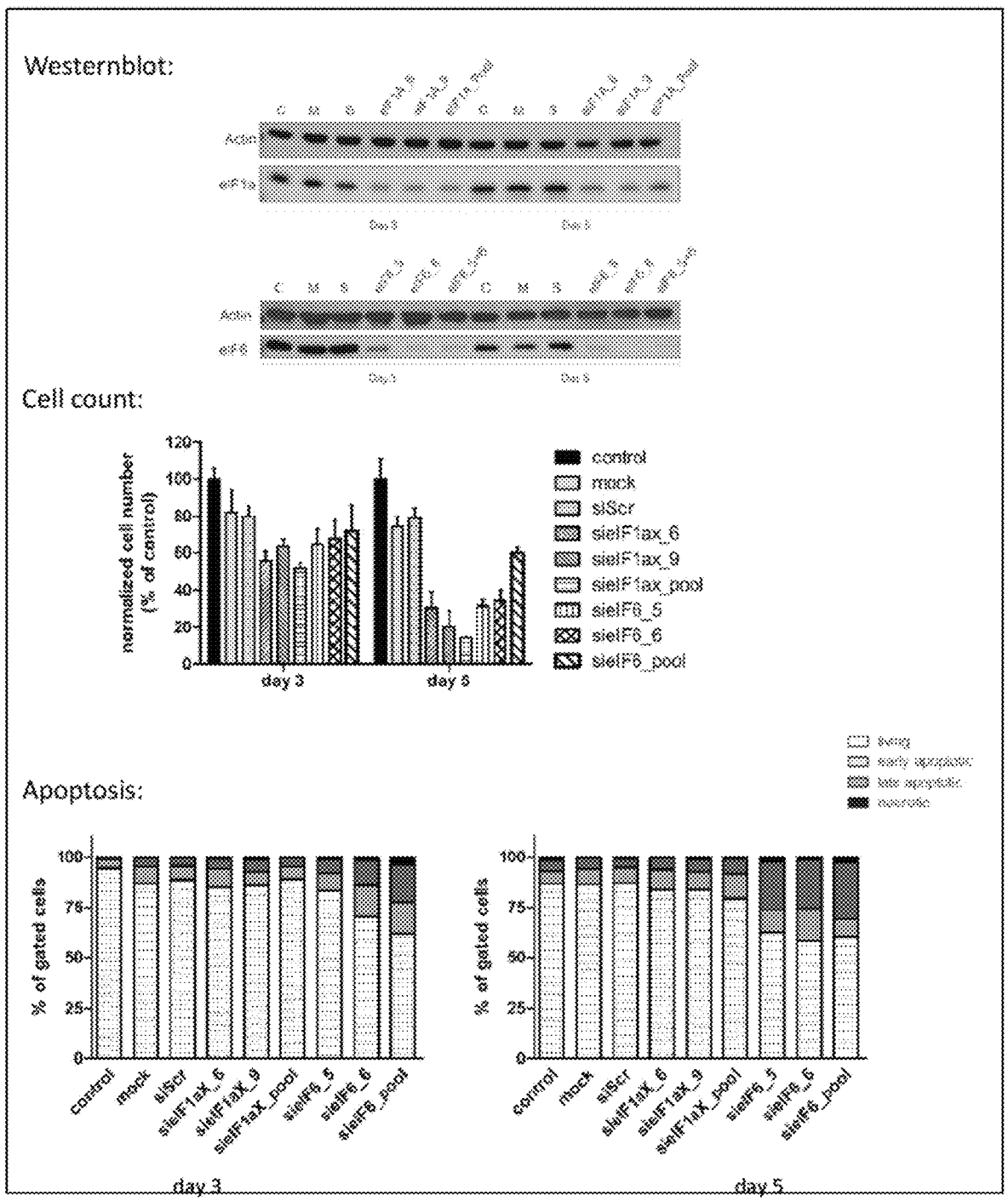
FIG. 4B shows reproduced silencing experiment in lung carcinoma cell line A549, where eIF6 and eIF1AX were knocked down. Both experiments inhibited proliferation. Knock down of eIF6 leads to higher apoptosis in A549.

In FIGS. 4A and 4B results of eIF6 and eIF1A knockdown in A549 cells are displayed. Cell proliferation is significant reduced in silenced cells. eIF6 knock down in A549 cells leads to apoptosis. eIF1A knock down in A549 does not show significant more apoptosis then controls.

Affimetrix Gene Expression Analysis of eIF6

Figure 35:
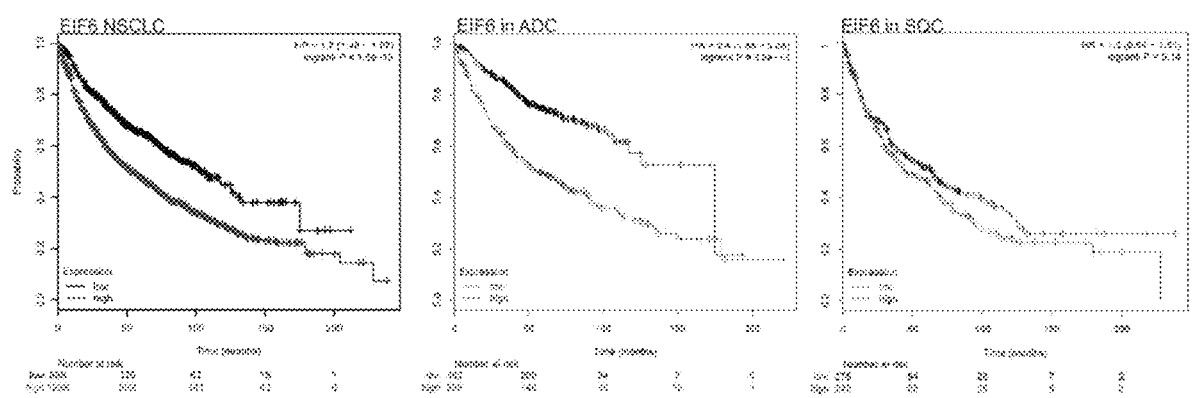
FIG. 35 shows Affimetrix gene expression analysis of eIF6 in NSCLC, ADC and SQC in correlation to patient overall survival. Survival is significantly influenced by eIF6 expression all three analysis. For NSCLC with a p-value of $1.5*10^{-13}$, ADC with a p-value of $3.8*10^{-13}$ and SQC with a p-value of 0.14.

In FIG. 35, the gene expression analysis and the influence on patient overall survival of eIF6 in NSCLC, ADC and SQC is displayed. High expression in NSCLC of eIF6 shows a significant worse outcome for patient overall survival ($p=1.5*10^{-13}$). The detailed analysis of eIF6 gene expression in ADC patients also significantly correlates with patient overall survival, high eIF6 expression leads to worse survival ($p=3.8*10^{-13}$). Also in SQC eIF6 gene expression shows a significant impact on patient overall survival ($p=0.14$).

Conclusion

As eIFs are significantly altered in lung tumors they potentially represent an oncological biomarker. The present data indicate a major contribution of eIFs and mTOR signaling to the development and progression of lung carcinomas. 2 eIFs which are upregulated in NSCLC and not mentioned in literature have been identified. Knock down of eIF6 and eIF1A leads to proliferation inhibition. eIF6 knock down leads to apoptosis. High gene expression of eIF6 in NSCLC has significantly worse outcome for patient overall survival. Analysing the subgroups ADC and SQC, it also influences SQC significantly but has more significant impact on ADC.

It is possible to stain eIF6 on immunohistochemistry (IHC) and determine eIF6 expression on routinely pathological bases and determine eIF6 protein expression level of Non Small Cell Lung Cancer (NSCLC) patients.

Example 2: Glioma

Gliomas are brain tumors deriving from glial cell origin. They are classified in four tumor grades according to their neoplastic behavior by the World Health Organization (WHO): pilozytic astrocytoma (grade I), diffuse astrocytoma (grade II), anaplastic astrocytoma (grade III) and glioblastoma multiform (GBM, grade IV). Out of these grades, low-grade gliomas (LGG, grades I and II) account for rather benign neoplasias, whereas high-grade gliomas (HGG, grades III and IV) represent malignant tumor forms.

GBMs have with more than 50% of all gliomas the highest occurrence of all gliomas. Although current GBM treatment strategies have improved over the past years by combining surgical resection, adjuvant radiotherapy and chemotherapy, the outcome is still very poor. The median survival of patients is approximately one year. One reason for the bad prognosis is the highly infiltrative nature of malignant gliomas which also leads to frequent recurrences. Therefore the development of novel therapeutic targets and treatments is strongly required.

Materials & Methods qRT-PCR

As housekeeping gene (HKG) a combination of glycerinaldehyd-3-phosphat-dehydrogenase (GAPDH) and succinate dehydrogenase A (SDHA) was used. Therefore the mean of the C(t) values of both HKGs was calculated and used for the $\Delta\Delta C(t)$-calculation.

In Silico Analyses

For bioinformatical analyses two different online databases were evaluated regarding eIF gene expression in glioma patients: REMBRANDT (Repository of Molecular Brain Neoplasia Data) and The Cancer Genome Atlas (TCGA). REMBRANDT is an online data portal that comprises molecular research and clinical trial data related to brain cancers, including gliomas (https://rembrandt.nci.nih.gov/). It allows a molecular classification of tumors based on gene expression and genomic data from tumors of patients. eIF gene expression was then analyzed using R package 'stats' (version 2.15.3) software (http://www.r-project.org/). Numbers: Non tumor n=21, WHO grade II n=61, grade III n=47, grade IV n=191.

The TCGA database is a collaborative project between the National Cancer Institute (NCI) and the National Human Genome Research Institute and comprises a collection of biomolecular investigations and clinical studies in the field of brain tumors (Tomczak K, et al. Contemporary Oncology. 19(2015):A68-A77). eIF gene expression in GBM patients was analysed in the TCGA database and correlated to the total patient survival in low grade glioma (LGG) and GBM patients. Additionally, the impact of temozolomide treatment was included in survival analyses. Statistical analyses were performed using the log-Rank test with defined significance values. Numbers: LGG n=389, GBM n=123, total n=535, without TMZ n=230.

Chemosensitivity Testings in Murine Xenograft Models

TABLE 3

Chemotherapeutic drugs used for chemosensitivity testings in vivo.

| | Application | Function |
|---|---|---|
| Temozolomide (Temodal) | First-line treatment GBM<br>Second-line treatment astrocytoma | Alkylating agent |
| Bevacizumab (Avastin) | Second-line treatment for GBM | Anti-VEGF monoclonal antibody (angiogenesis inhibitor) |
| Irinotecan | First-line treatment colon carcinomas<br>Clinical trials for GBM treatment | Topoisomerase inhibitor |
| Sorafenib | Clinical trials for GBM treatment | Protein kinase inhibitor |
| Everolimus | Clinical trials for LGG treatment | mTOR inhibitor |
| Salinomycin | Experimentally tested for glioma therapy | Polyether antibiotic |
| Regorafenib | Clinical trials for relapsed GBMs | Tyrosine kinase inhibitor |
| Thalidomide | Clinical trials for recurrent GBMs<br>Clinical trials in combination with temozolomide and irinotecan | Immunomodulatory drug (VEGF inhibitor) |

Additionally to single treatments with each compound, combination therapies for Temozolomide/Everolimus, Temozolomide/Regorafenib and Temozolomide/Thalidomide were investigated.

Chemosensitivity Testings in Human Glioma Cell Lines

For in vitro chemosensitivity testings, same compounds were used as for in vivo testings. Additionally, three compounds were added to the in vitro testing panel (listed in table 4).

TABLE 4

Chemotherapeutic drugs additionally used for in vitro chemosensitivity testings.

| | Application | Function |
|---|---|---|
| Etoposide | Clinical trials for GBM treatment | Topoisomerase inhibitor |
| SAHA (Vorinostat) | Experimentally tested for glioma therapy | Anti-epileptic drug |
| Valproic acid | Clinical trials for GBM treatment | Histone-deacetylase inhibitor |

3 distinct human neuroglioma cell lines were used for chemosensitivity testings: A172, U-87 MG (purchased from LGC Standards, Germany) and U251 MG (purchased from Sigma, Germany). A172 and U-251 MG cells were cultured at 37° C., 5% $CO_2$ and 95% humidity in DMEM medium containing 10% fetal bovine serum and 10 mg/ml Penicillin/Streptomycin (growth medium, all Lonza, Belgium). U87-MG were cultured at 37° C., 5% $CO_2$ and 95% humidity in EMEM medium containing 10% fetal bovine serum and 10 mg/ml Penicillin/Streptomycin (growth medium, all Lonza, Belgium).

Chemosensitivity testings were performed over three different time points (1, 3 and 5 days) using three distinct concentrations of each compound (see table 5). As most of the compounds were dissolved in dimethyl sulfoxide (DMSO), DMSO treatment was used as control treatment. Three days before treatment, cells were seeded into 100 mm dishes ($2 \times 10^4$ cells/cm$^2$). On treatment day, growth medium was removed and replaced with growth medium containing the respective compound. During treatment period, media containing the respective compounds were changed every second day. Cells were harvested after 1, 3 and 5 days and cell number and viability were determined. Cell pellets were then snap frozen and analyzed on protein (Immunoblot, immunofluorescence) and mRNA (qRT-PCR) level.

Figure 5:
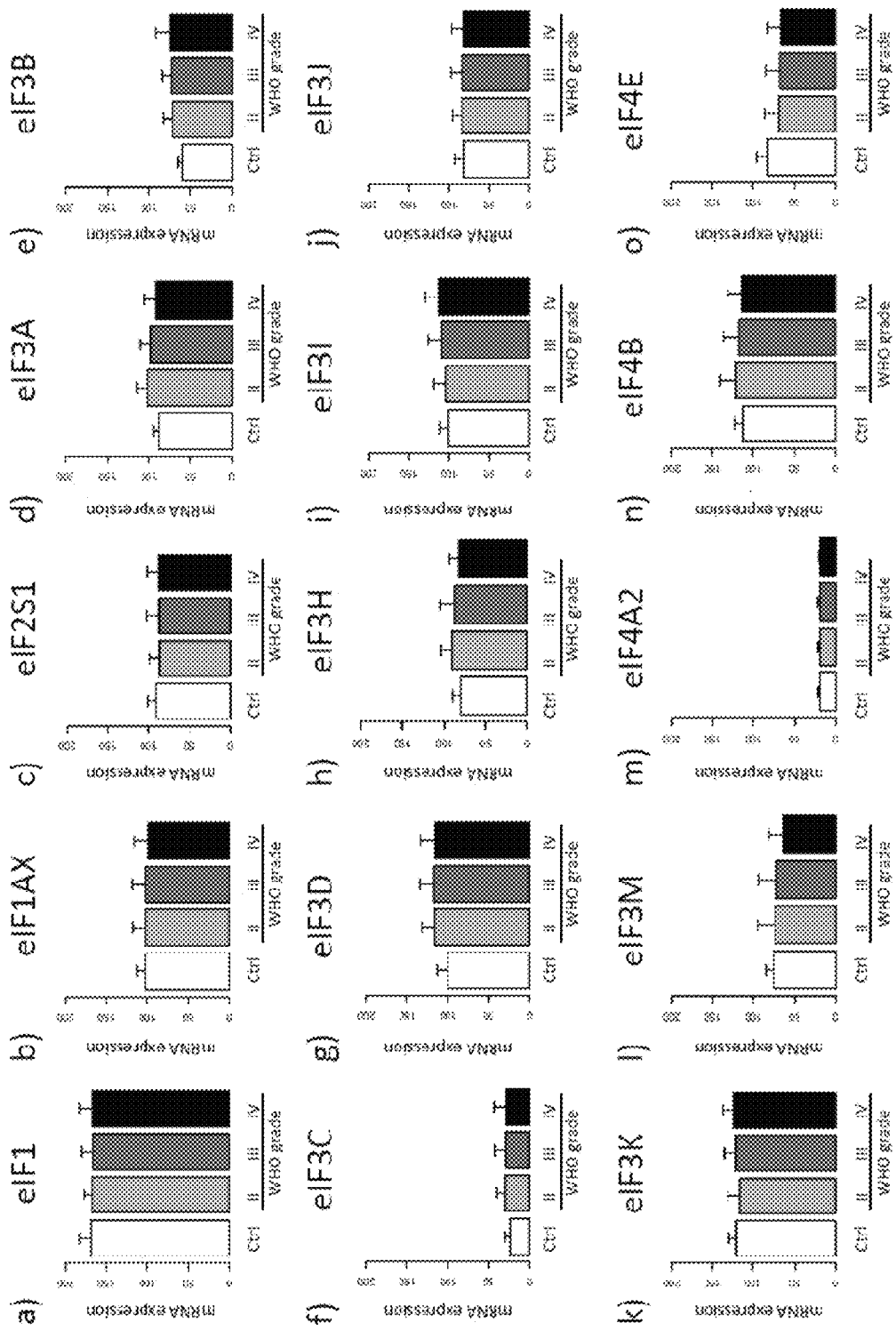
FIG. 5 shows the REMBRANDT gene expression analyses of eIFs in astrocytomas grade II-IV compared to non tumor controls. eIF gene expression represented in bars+SD was analysed for eIF1 (a), eIF1AX (b), eIF2S1 (c), eIF3A (d), eIF3B (e), eIF3C (f), eIF3D (g), eIF3H (h), eIF3I (i), eIF3J (j), eIF3K (k), eIF3M (1), eIF4A2 (m), eIF4B (n), eIF4E (o), eIF4G1 (p), eIF4H (q), eIF5 (r) and eIF6 (s). Numbers: non tumor: n=21, grade II: n=61, grade III: n=47, grade IV: n=191.
Figure 5:
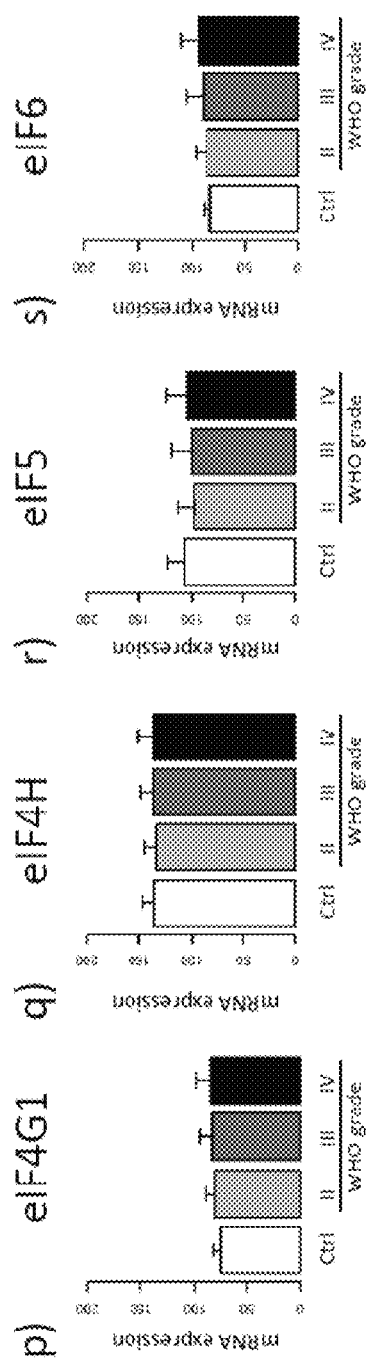

5p) and eIF6 (FIG. 5s). An interesting expression pattern was identified for eIF3A (FIG. 5d) and eIF3H (FIG. 5h) as gene expression was up-regulated compared to controls, but grade II and III tumors showed a higher gene expression compared to grade IV. eIF4E (FIG. 5o) gene expression was down-regulated compared to controls.

Figures 36, 36A, 36B, 36C, 36D, 36E, 36F:
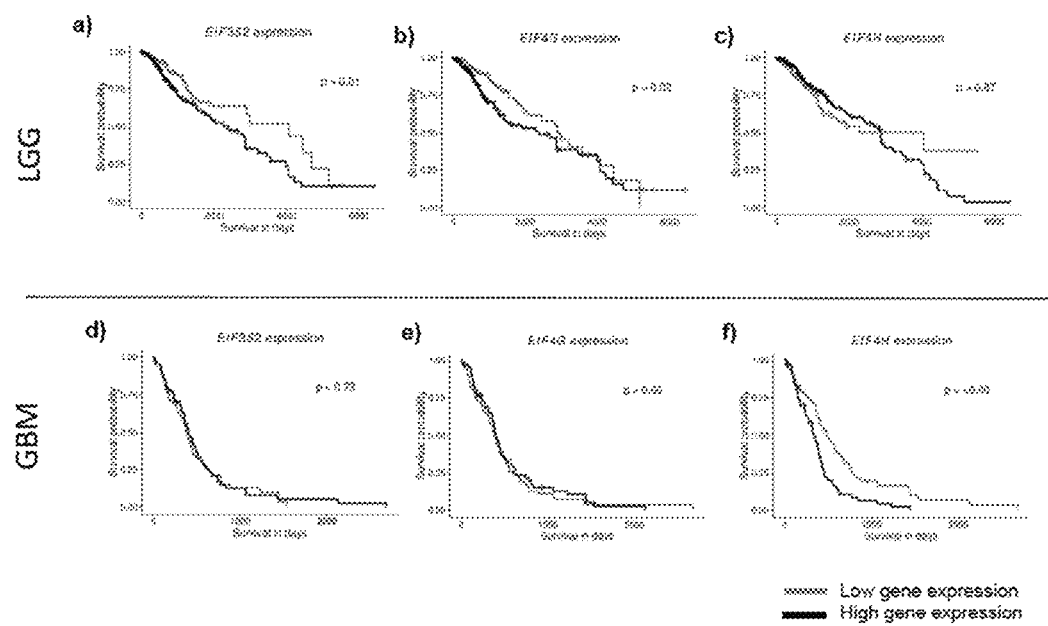
FIGS. 36A-36F shows the impact of eIF gene expression on patients overall survival in LGG and GBM using data from the TCGA database. Kaplan-Meier survival curves were calculated based on eIF3I (FIGS. 36A, 36D) eIF4G (FIGS. 36B, 36E) and eIF4H (FIGS. 36C, 36F) gene expression for patients with LGG (FIGS. 36A-36C) and GBM (FIGS. 36D-36F). Numbers: LGG: n=389, GBM: n=123.

Additionally, eIF gene expression in GBM patients was statistically evaluated in the TCGA data base and correlated with patient survival probabilities. TCGA analyses were performed for LGG and GBM patients (FIG. 36). Interestingly, different eIF subunits significantly affected the survival of LGG and GBM patients. In LGG, low eIF3S2 (=eIF3I, p<0.01; FIG. 36a) and eIF4G (p<0.02; FIG. 36b) expression lead to a significantly increased overall survival in LGG patients. In GBM patients, low eIF4H expression levels (p<0.001) revealed a significantly higher overall survival (FIG. 36f).

Taking all patients of the TCGA database without any exclusion criteria, statistical analyses revealed a higher survival probability for patients with increased eIF4EBP2 expression (leaf 2) in comparison to patients with lower eIF4EBP2 expression (p-value=2e-08). If additionally eIF4H expression is included, survival probabilities of GBM patients increased with low (leaf 6) compared to high eIF4H levels (leaf 7, FIG. 6a, b).

Same analyses were performed with the exclusion of patients treated with temozolomide (TMZ), one of the standard chemotherapeutics for GBMs. Patients treated without TMZ have higher survival probabilities revealing low eIF4H and eIF1AX gene expression (leaf 4, p-value=9.07e−06). High eIF4H levels showed the same outcome in survival (leaf 3) as low eIF4H in addition to high eIF1AX expression (leaf 5, FIG. 6c, d).

TABLE 5

Concentrations for chemosensitivity testings in vitro.

| | Temozolomide | Irinotecan | Etoposid | Sorafenib | Everolimus | SAHA (Vorinostat) | Valproic acid | Salinomycin |
|---|---|---|---|---|---|---|---|---|
| Concentration 1 | 20 μM | 1 μM | 10 nM | 5 μM | 50 nM | 1 μM | 1 mM | 500 nM |
| Concentration 2 | 50 μM | 20 μM | 100 nM | 10 μM | 100 nM | 5 μM | 5 mM | 5 μM |
| Concentration 3 | 100 μM | 50 μM | 10 μM | 20 μM | 1 μM | 10 μM | 10 mM | 10 μM |

Results

In Silico Analyses of eIF Gene Expression in Glioma Patients

Before biochemical analyses, eIF expression was either evaluated in all 4 tumor grades or in grade 2-4 in silico. REMBRANDT data analyses revealed up-regulation in tumor grades 2-4 compared to control samples of following genes: eIF3C (FIG. 5f), eIF3D (FIG. 5g) A gradual increase in eIF gene expression over all three tumor grades could be observed for eIF3B (FIG. 5e), eIF3I (FIG. 5i), eIF4G1 (FIG.

eIF mRNA Expression Patterns in Glioma Tissue eIF mRNA expression was examined using quantitative RT-PCR. Regarding the mRNA expression pattern, an up-regulation of the following genes was observed in all tumor grades compared to healthy control samples: eIF3A (FIG. 7a), eIF3B (FIG. 7b), eIF3C (FIG. 7c), eIF4A1 (FIG. 7f), eIF4G1 (FIG. 7i), eIF4H (FIG. 7j), eIF5 (FIG. 7k) and eIF6 (FIG. 7l). eIF3M (FIG. 7e) solely showed increased mRNA expression in grade II and III tumors. A stepwise increase over all tumor grades was observed for eIF4E (FIG. 7g), 4EBP1 (FIG. 7h) and eIF3I (FIG. 7d).

Figure 8:
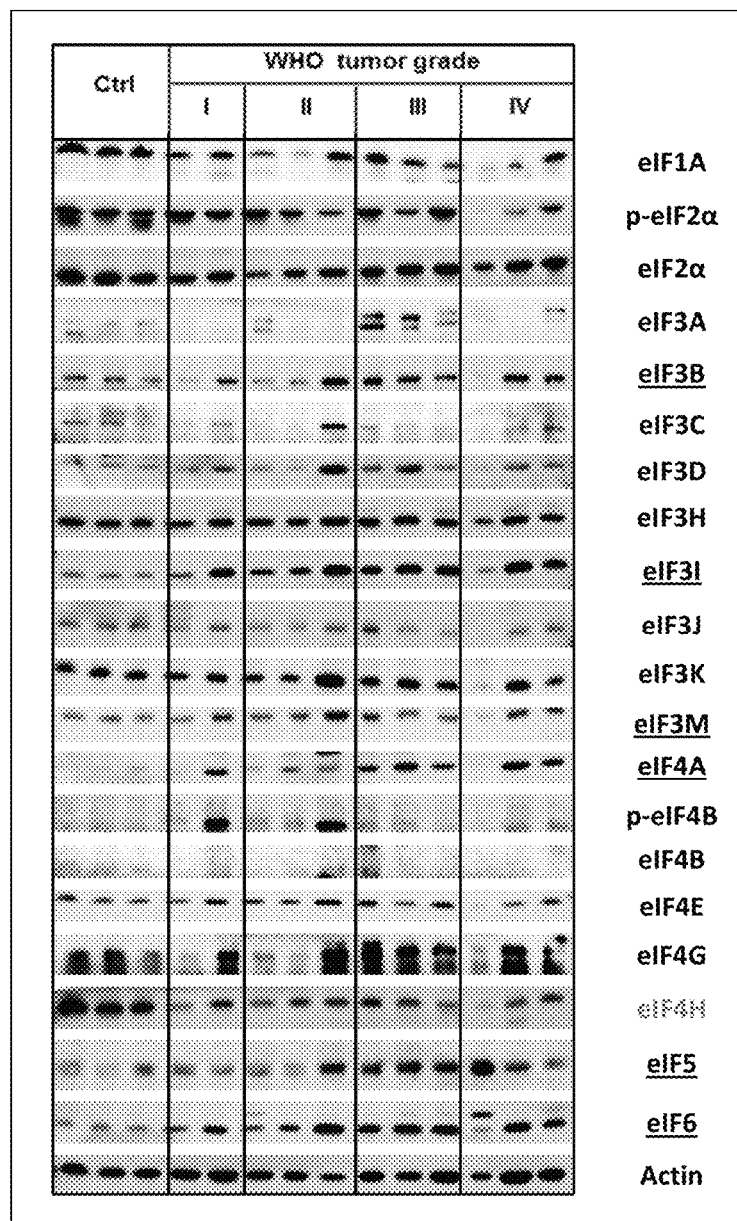
FIG. 8 shows eIF protein expression in astrocytomas (grade I-IV) compared to healthy brain tissue (Ctrl) using immunoblot analyses. eIF subunits up-regulated in tumor tissue compared to healthy control tissue are underlined, down-regulated ones are highlighted in grey. Actin was used as loading control. Numbers: Control (Ctrl): n=3, grade I: n=2, grade II-IV: n=3.

Protein Expression Pattern in Glioma Patients eIF protein expression pattern was analyzed using two distinct methods. Protein expression analyses using immunoblot revealed an up-regulation of various eIF subunits (FIG. 8). eIF3B, eIF3I, eIF3M, eIF4A, eIF5 and eIF6 levels were elevated upon all four tumor grades. eIF3A levels seemed to be increased only in grade III astrocytomas. eIF4H showed decreased protein expression in all tumor tissues compared to healthy controls (FIG. 8).

Additionally to immunoblot analyses, protein expression pattern was investigated immunohistochemically. Besides grade III, eIF3C protein levels are increased in all tumor types compared to healthy control tissue. The difference was even significant between grade II and controls (p<0.05, FIG. 9a. Immunohistochemical analyses of eIF4G protein expression revealed a significant downregulation in all tumor grades (grade II, III p<0.05, grade I p<0.001). eIF4G protein expression though seemed to gradually increase from grade I-IV (FIG. 9b). eIF4H levels were significantly up-regulated in all tumor grades in comparison to the control tissue (grade I, III, IV p<0.01, grade II p<0.001; FIG. 9c), eIF5 levels were slightly elevated in tumor samples, although the difference solely reached a significance level between grade II and controls (p<0.05; FIG. 9d). eIF6 protein expression was very strong within all tested tissue, but no difference between tumor and control tissue was detected (FIG. 9e).

Therapeutic Relevance for eIFs in Glioma

Figure 10:
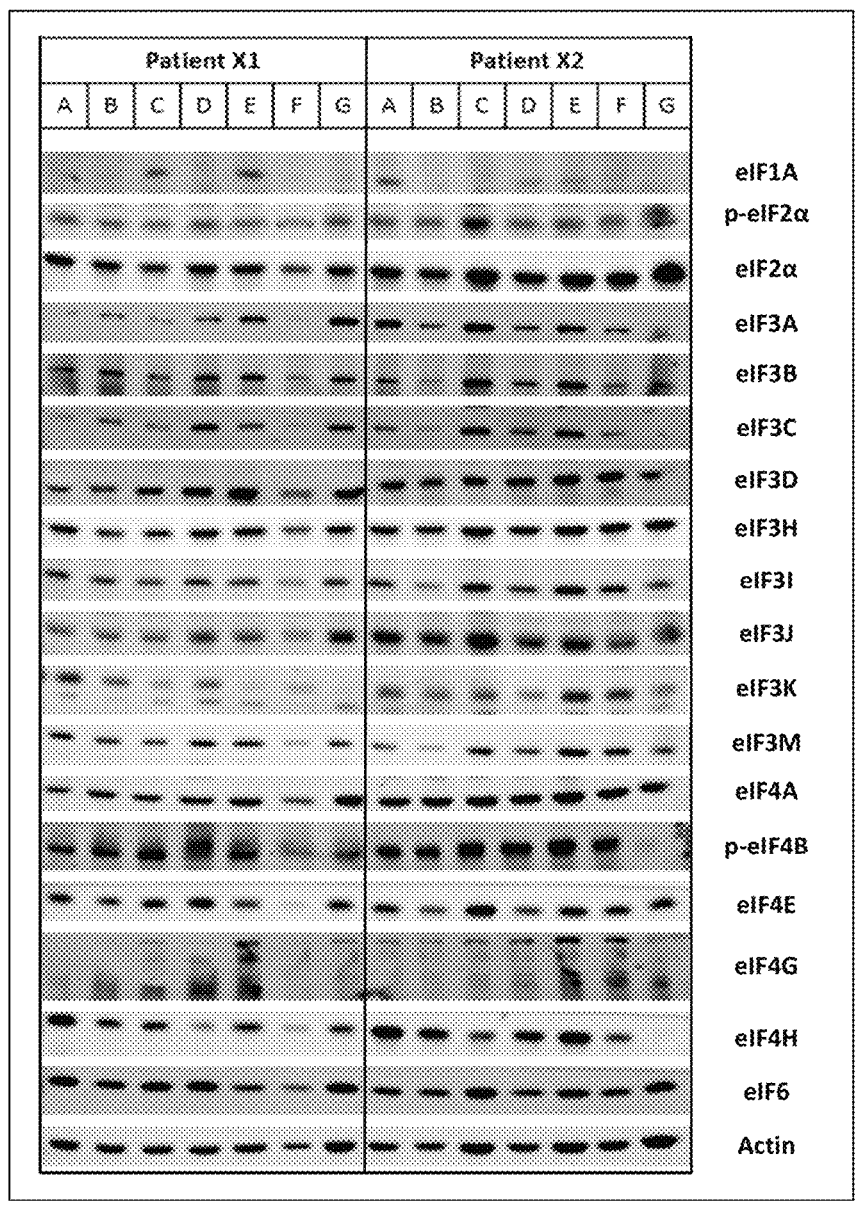
FIG. 10 shows eIF protein expression after chemosensitivity testings in 2 different murine GBM xenografts models (Patient X1 and X2) using immunoblot analyses. Chemosensitivity testings were performed with the following cytostatics: Everolimus (B), Sorafenib (C), Bevacizumab (Avastin) (D), Irinotecan (E), Salinomycin (F) and Temozolomide (G). As control treatment for murine xenografts phosphate buffered saline (PBS, A) was used. Actin was used as loading control. Number: n=2/group.
Figure 11:
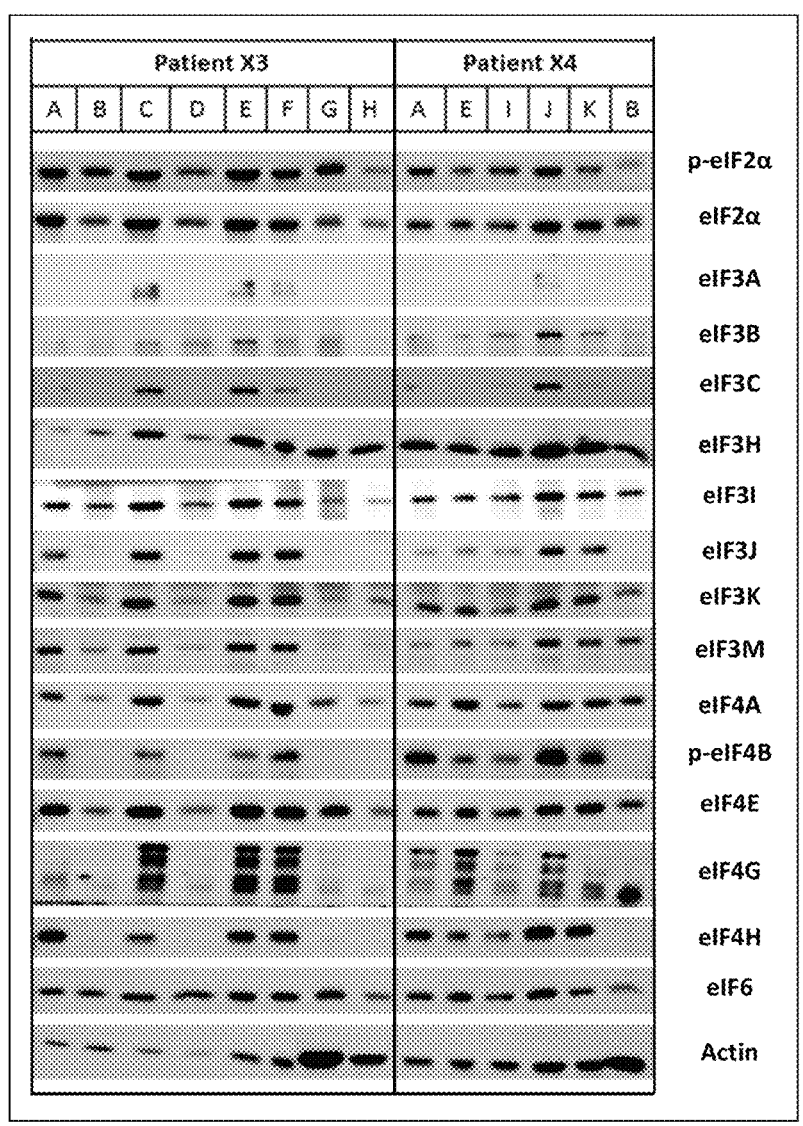
FIG. 11 shows eIF protein expression after chemosensitivity testings in 2 different murine GBM xenografts models (Patient X3 and X4) using immunoblot analyses. Chemosensitivity testings were performed with the following cytostatics: Temozolomide (B), Thalidomide (C), Everolimus (E), Regorafenib (G), Sorafenib (I), Bevacizumab (Avastin) (J) and Irinotecan (K). Temozolomide treatment was combined with Thalidomide (D), Everolimus (F) and Regorafenib (H). As control treatment for murine xenografts phosphate buffered saline (PBS, A) was used. Actin was used as loading control. Number: n=1-2/group.

To evaluate the therapeutic relevance of eIFs in glioma, eIF protein expression was analyzed after chemosensitivity testings in murine GBM xenograft models (FIGS. 10, 11, 37 and 38). For the chemosensitivity testings several cytostatics, which are either already in clinical usage or in clinical trials for glioma treatment, were evaluated regarding their influence on eIF expression. After treatment with Everolimus, Sorafenib or Salinomycin and Thalidomide almost no difference in eIF protein expression was observed compared to PBS treated controls except for eIF3C, which was upregulated (FIGS. 10 and 11). Bevacizumab induced the down-regulation of eIF3K and Irinotecan treatment revealed differential effects. Those effects shown in FIGS. 10 and 11 could be also confirmed in higher xenograft numbers (FIG. 37). After Temozolomide treatment, which effectively reduced tumor growth, p-eIF2α (FIG. 37b), eIF3A (FIG. 37d), eIF3B (FIG. 37e), eIF3C (FIG. 37f), eIF3D (FIG. 37g), eIF3H (FIG. 37h), eIF3I (FIG. 37i), eIF3I (FIG. 37j), p-eIF4B (FIG. 37n), eIF4E (FIG. 37o), eIF4G (FIG. 37p) and eIF4H (FIG. 37q, p<0.01) protein levels were significantly reduced in comparison to the PBS control and other treatments. However, eIF6 (FIG. 37r) and eIF4A (FIG. 37m) did not response to Temozolomide treatment. In the Temozolomide resistant xenograft model X5 eIF6 protein expression was even increased compared to the non-resistant models (FIG. 37r).

Interestingly, after treatment with Regorafenib, which is in clinical trials for relapsed GBMs, almost all eIF subunits were totally down-regulated compared to the PBS control (FIGS. 11 and 38, Patient X3). A similar effect was observed after Temozolomide treatment, which is the standard first-line therapy in GBM patients (FIGS. 10, 11 and 38). Combination treatments of Regorafenib, Everolimus or Thalidomide with Temozolomide did not reveal any differences in eIF protein expression compared to single Temozolomide treatment.

Figure 12:
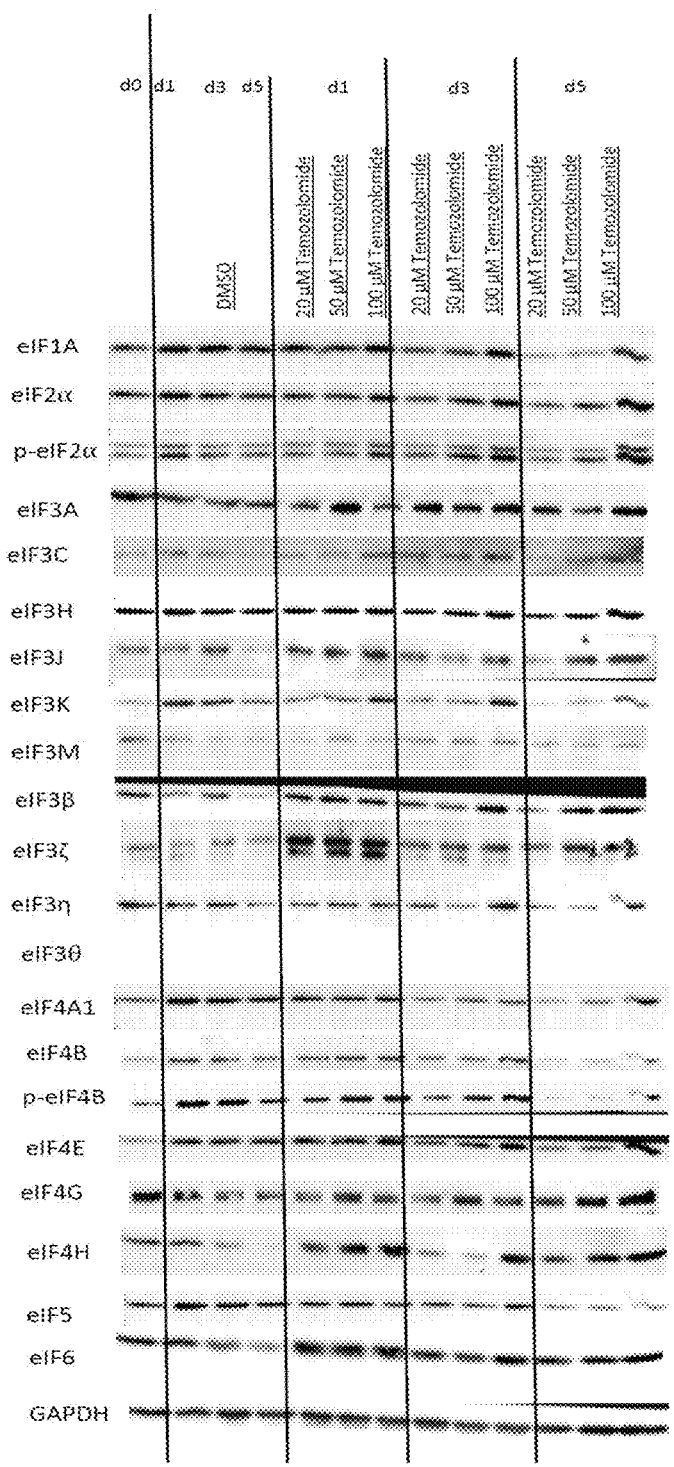
FIG. 12 shows eIF protein expression after Temozolomide treatment in the U-87 MG glioma cell line using immunoblot analyses. U-87 MG cells were treated with Temozolomide for 1 (d1), 3 (d3) and 5 days (d5). 3 distinct concentrations were used for the treatment: 20, 50 and 100 µM. As control, cells without treatment (d0) and cells treated with DMSO were taken. GAPDH was used as loading control.
Figure 13:
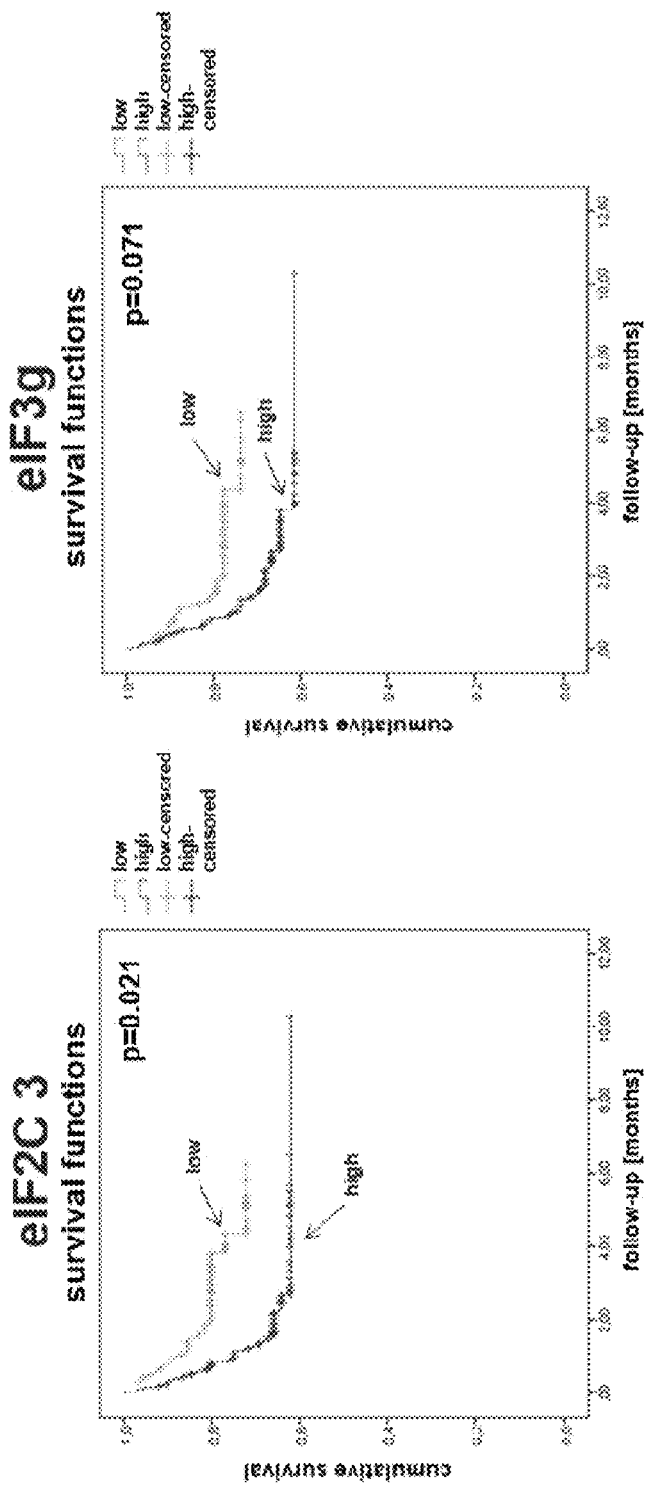
FIG. 13 shows the expression/survival correlation for the $1^{st}$ quartile cut off level between high and low eIF expression, in particular of eIF2C 3, eIF3g, eIF-4G1 and eIF-5, in DLBCL. Analyzed was the correlation between the expression of the mRNA coding for the respective indicated protein and patient outcome.
Figure 13:
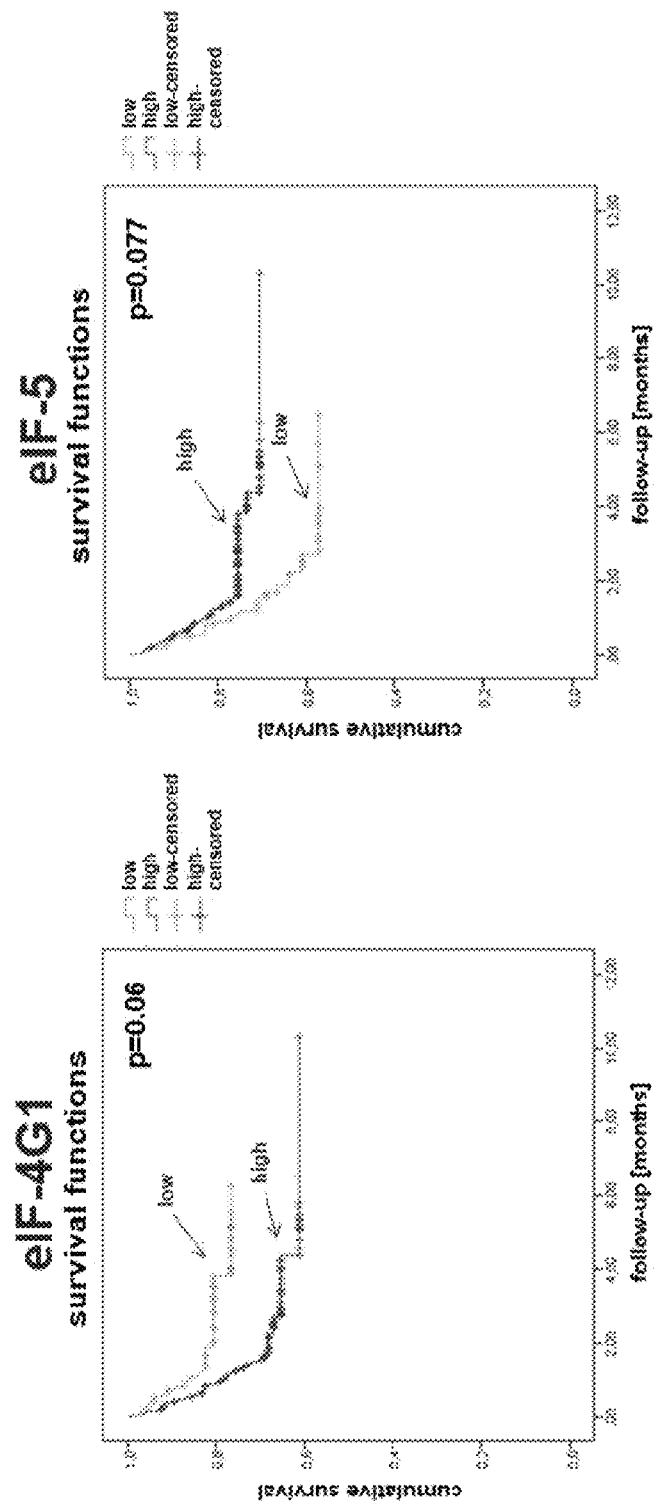
Figure 14:
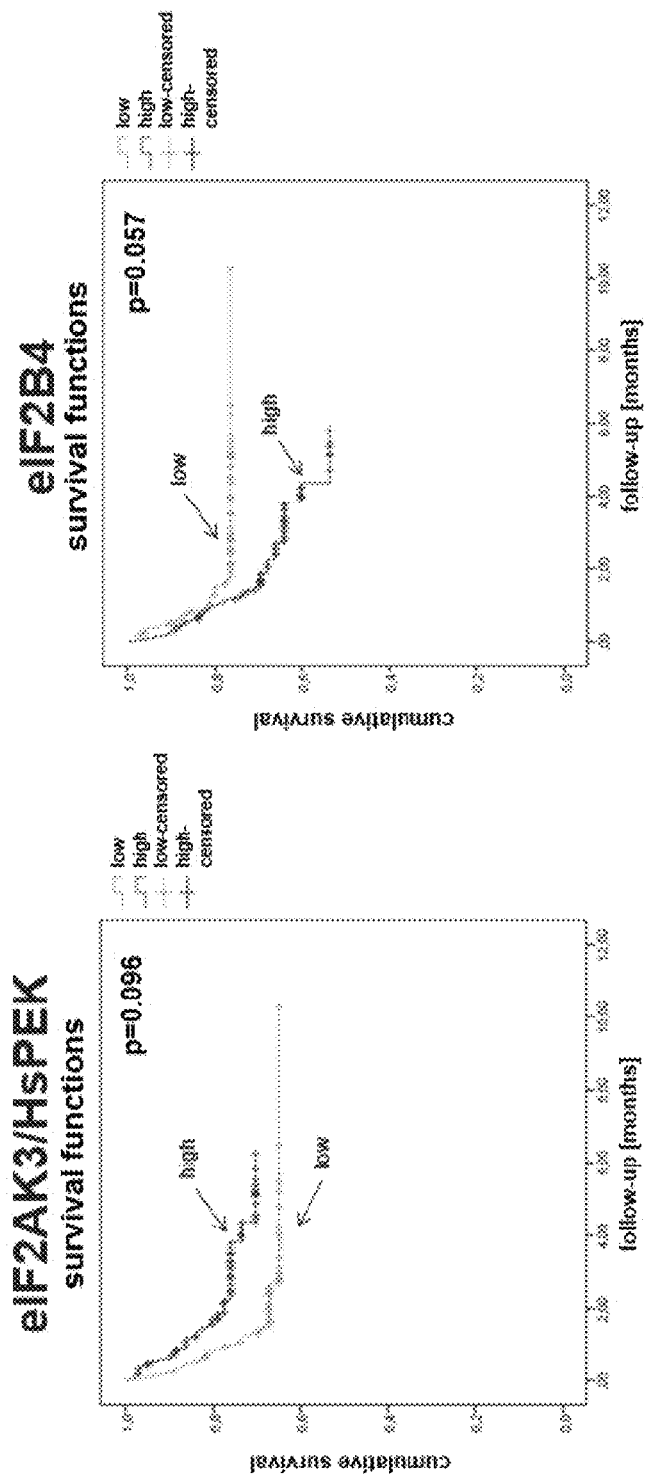
FIG. 14 shows the expression/survival correlation for the Median cut off level between high and low eIF expression, in particular of eIF2AK3/HsPEK, eIF2B4/eIF-2B subunit delta, eIF3c and 4E-BP1, in DLBCL. Analyzed was the correlation between the expression of the mRNA coding for the respective indicated protein and patient outcome.
Figure 14:
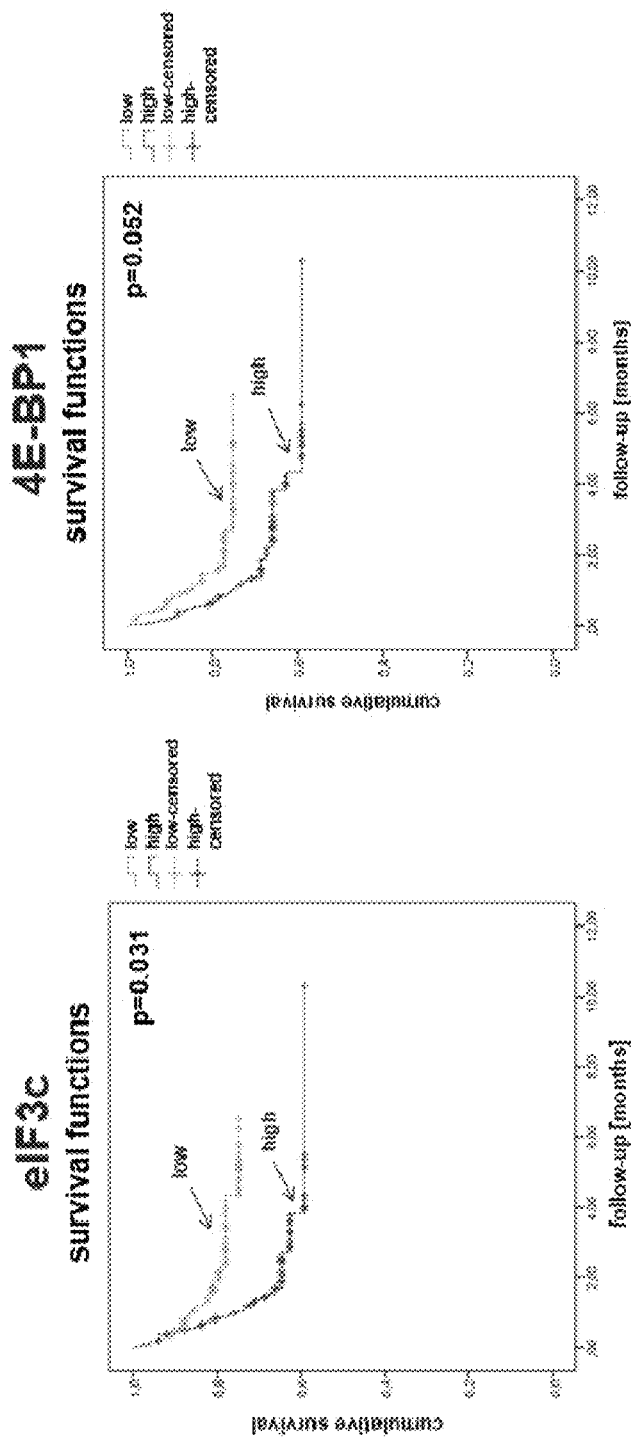
Figure 15:
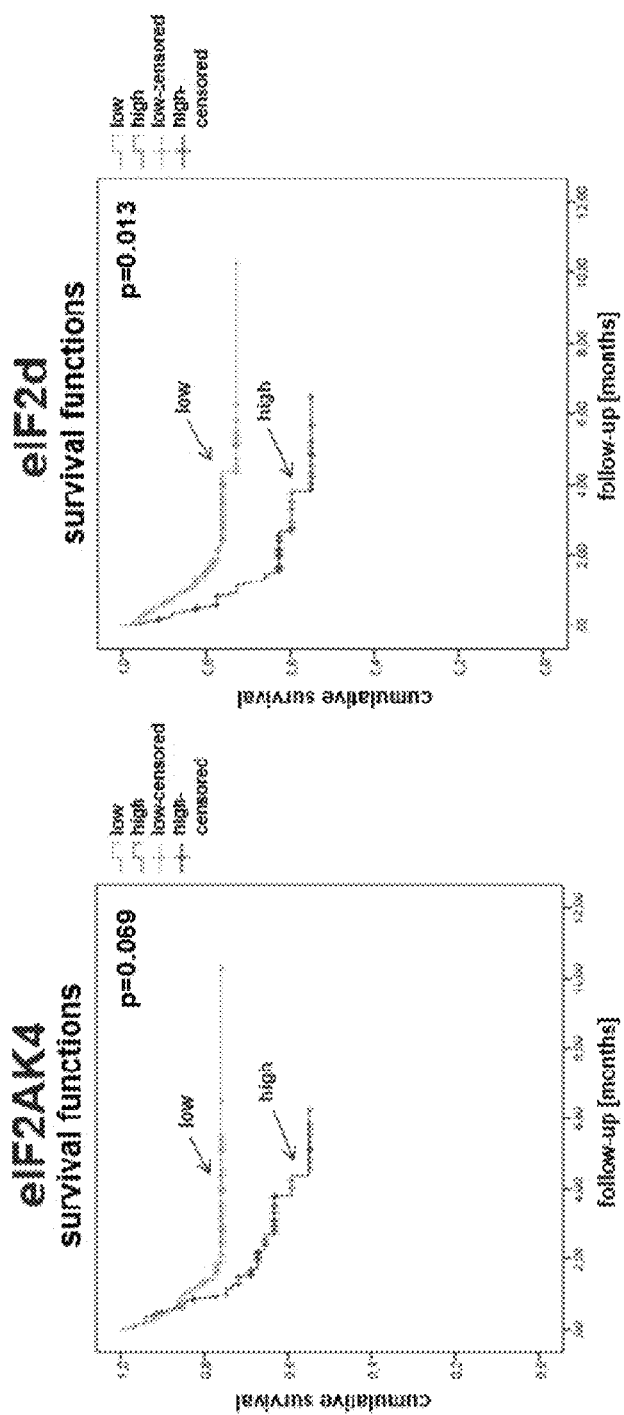
FIG. 15 shows the expression/survival correlation for the $3^{rd}$ quartile cut off level between high and low eIF expression, in particular of eIF2AK4, eIF2d, eIF-2a and eIF-2-beta/eIF2S2, in DLBCL. Analyzed was the correlation between the expression of the mRNA coding for the respective indicated protein and patient outcome.
Figure 15:
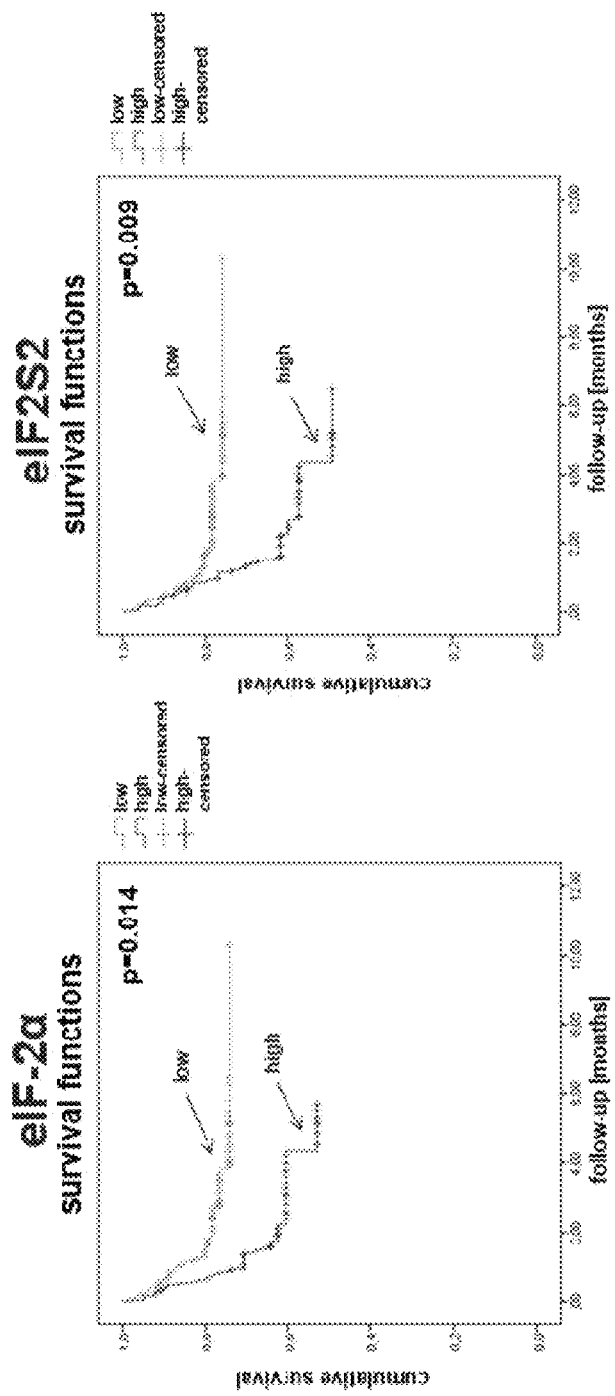
Figure 16:
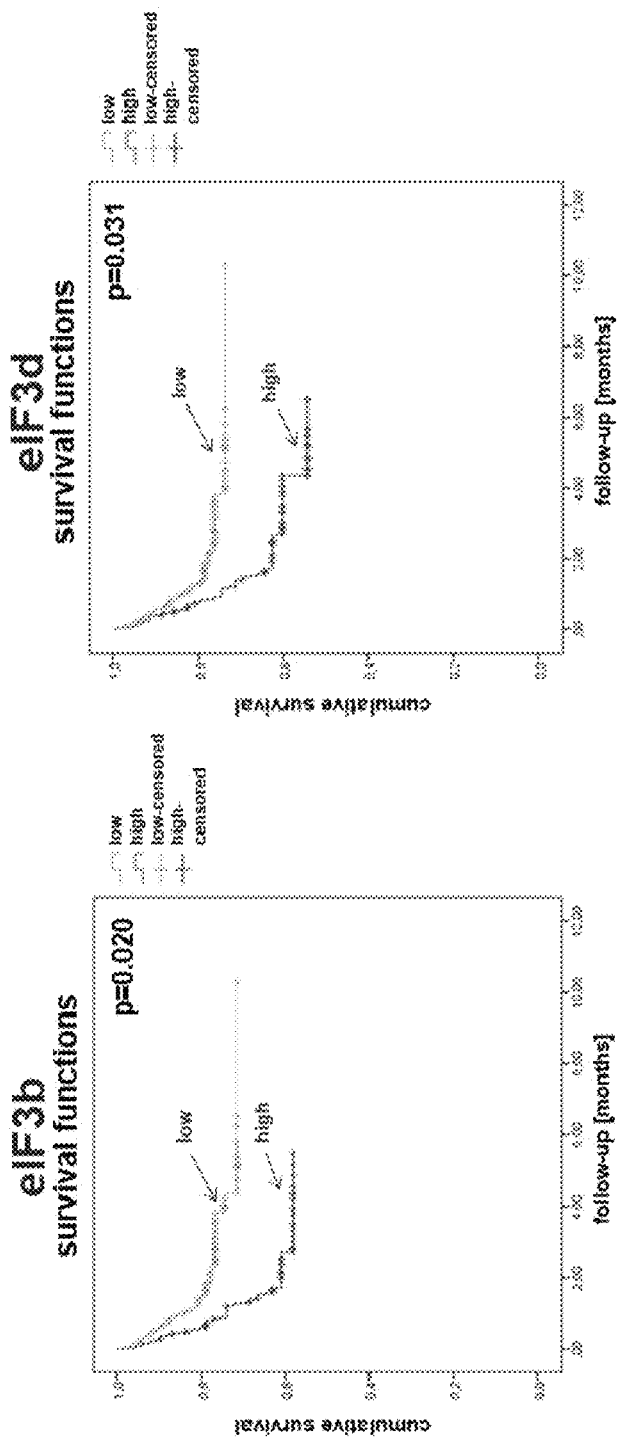
FIG. 16 shows the expression/survival correlation for the $3^{rd}$ quartile cut off level between high and low eIF expression, in particular of eIF3b, eIF3d, eIF3f and eIF3l, in DLBCL (continued). Analyzed was the correlation between the expression of the mRNA coding for the respective indicated protein and patient outcome.
Figure 16:
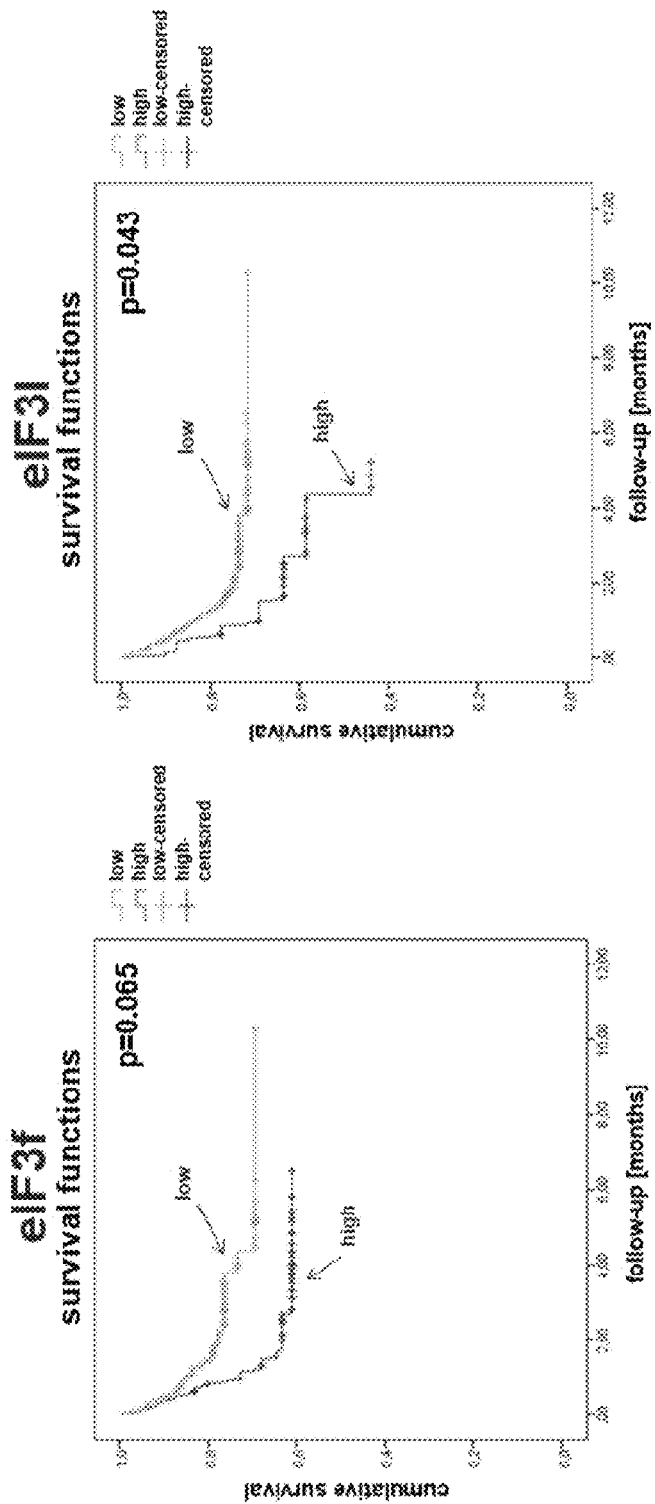
Figure 17:
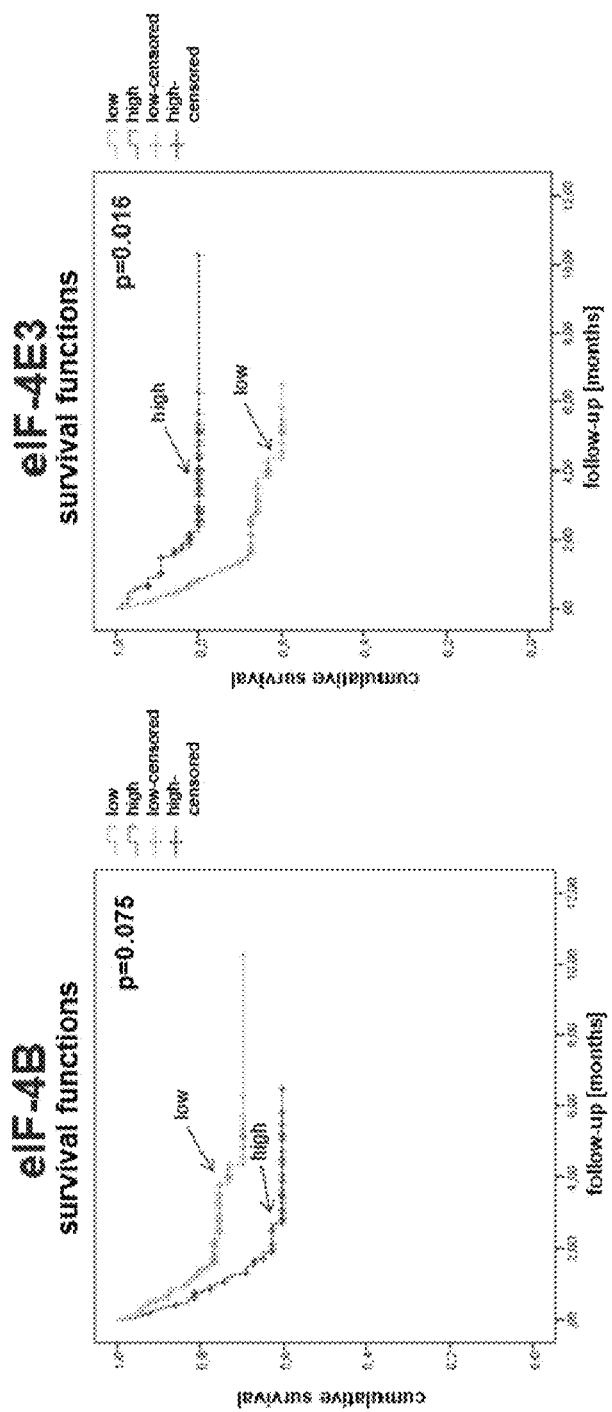
FIG. 17 shows the expression/survival correlation for the $3^{rd}$ quartile cut off level between high and low eIF expression, in particular of eIF-4B, eIF-4E3 and eIF-5A, in DLBCL (continued). Analyzed was the correlation between the expression of the mRNA coding for the respective indicated protein and patient outcome.
Figure 17:
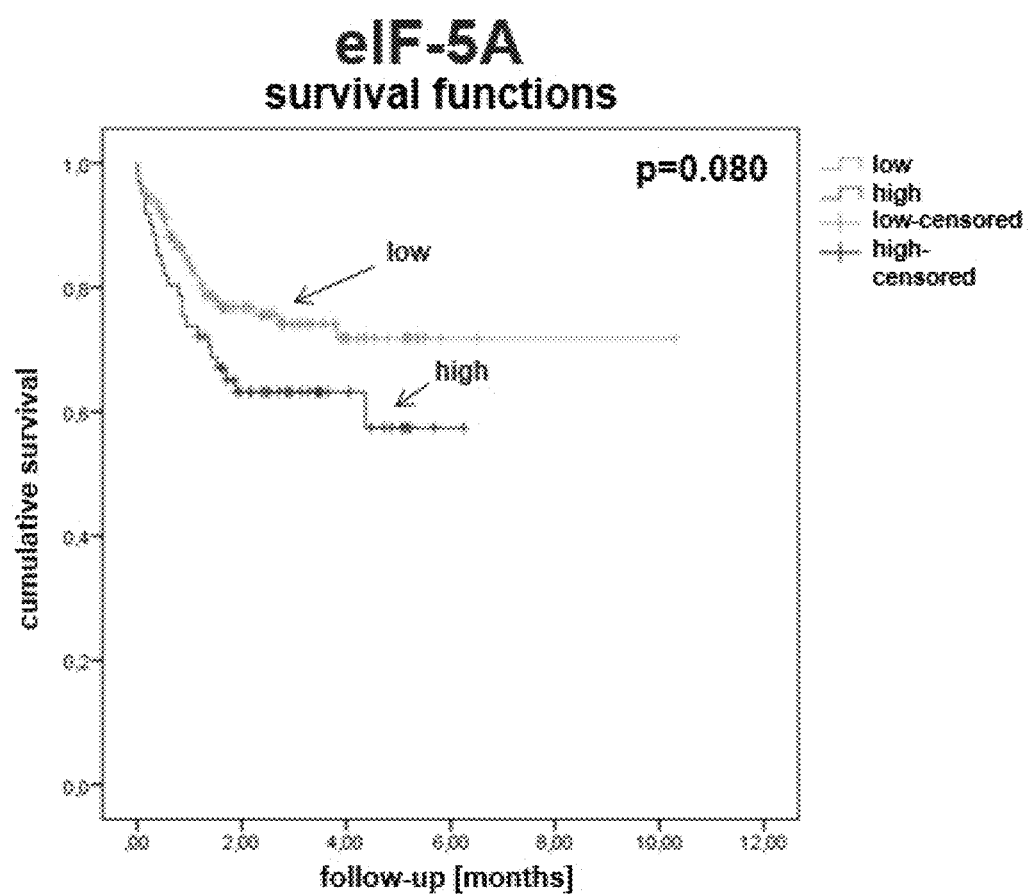

The down-regulation of eIFs after Temozolomide treatment has been also confirmed in the U-87 MG cell line in vitro (FIG. 12). Several eIF subunits were down-regulated after Temozolomide treatment for 3 and 5 days. Almost no effect was observed after the first day of treatment. This implicates that Temozolomide induced down-regulation of eIF subunits is a process of at least 3 days. Interestingly, the highest Temozolomide concentration (100 μM) seemed to block eIF downregulation.

In near future, also other treatments listed in Table 4 will be analyzed regarding their influence on eIF expression in three different glioma cell lines.

Discussion

Besides the already known eIFs, which might be involved in gliomagenesis, novel subunits altered in all glioma grades were found. Elevated levels of eIF3A, eIF3B, eIF3I, eIF3M, eIF4A, eIF5 and eIF6 were observed on protein and mRNA level. Additionally to the up-regulated eIF subunits, eIF4H was found to be down regulated on protein level using immunoblot analyses, but not immunohistochemistry.

Especially eIF4H and eIF3I seemed to have a special role in gliomagenesis. TCGA analyses revealed an impact of eIF4H and eIF3I gene expression on glioma patient overall survival. Contrary results were found for eIF4H protein expression as it was down-regulated using immunoblot analyses and up-regulated in immunohistochemical analyses. This opposite trend has to be evaluated in more detail.

Potential therapeutic relevance for eIFs in glioma treatment was shown after chemosensitivity testings in the murine xenograft model. After Regorafenib and Temozolomide treatment, eIF expression was totally down-regulated in an indirect manner. Down-regulation of various eIF subunits after Temozoloide treatment was also confirmed in human neuroglioma cell lines in vitro. Temozolomide, the most frequent used first-line therapy in high grade glioma, also showed the most effective tumor growth reduction in murine GBM xenografts. Thus, an eIF directed down-regulation via eIF inhibitors or siRNA in GBM patients might also reveal a positive therapeutic effect as Temozolomide.

Example 3: Lymphoma

Blood cancer is one of the most important cancers in Europe. Within the wide-spread group of blood cancer, malignant lymphomas are a heterogeneous group of neoplastic disorders affecting the lymphatic system. 95% are of B-cell origin. Within B-cell lymphomas a further distinction can be made into Hodgkin's (HL) and non-Hodgkin's lymphoma (NHL). NHL comprise neoplasms with diverse biological and clinical manifestations, including the most common lymphoma subtype, the diffuse large B-cell lymphoma (DLBCL). The prognosis for these lymphatic neoplasms is still bad with 35% of affected patients dying of the disease within the first year after diagnosis. Treatment options are limited, mostly focusing on chemotherapeutic approaches.

So far several publications about the impact of eIFs on lymphomagenesis and lymphoma progression exist. However, the involved research groups have mainly focused on the eIF4F complex, the most intensively studied eIF complex in all tumor entities, and its contribution.

Importantly, there are no publications so far analyzing the relationship between the expression of the whole range of eIF-subunits and patient outcome. As mentioned above, the research focus has been mainly concentrated on the eIF4F-complex. Thus, research studies, investigating the complete range of eIFs, are lacking. Our research group intended to fill this gap.

Materials and Methods

Survival Analysis

The survival analysis between respective eIF expression and patient survival was performed based on the Lenz-dataset which was published by Lenz G et al. (New Engl J Med 359(2008):2313-2323).

Gene expression of 56 eIFs (see table 6) was analyzed in 200 Diffuse Large B-cell Lymphoma (DLBCL) patients which were treated with R-CHOP-chemotherapy (Combination therapy composed of the active ingredients: Rituximab, Cyclophosphamide, Hydroxydaunorubicin, Vincristine, Predniso(lo)ne). R-CHOP-chemotherapy is the standard treatment approach to treat this kind of lymphatic cancers. A panel of expert hemato-pathologists confirmed the diagnosis of DLBCL using current World Health Organization criteria. The gene expression was investigated on mRNA level by using Affymetrix U133 plus 2.0 microarrays (Affymetrix, USA).

TABLE 6

| EIF1 | EIF3I | EIF2B5 | EIF4EBP2 |
|---|---|---|---|
| EIF1AD | EIF3J | EIF2D | EIF4EBP3 |
| EIF1AX | EIF3K | EIF2S1 | EIF4ENIF1 |
| EIF1AY | EIF3L | EIF2S2 | EIF4G1 |
| EIF1B | EIF3M | EIF2S3 | EIF4G2 |
| EIF2A | EIF4A1 | EIF2S3L | EIF4G3 |
| EIF2AK1 | EIF4A2 | EIF3A | EIF4H |
| EIF2AK2 | EIF4A3 | EIF3B | EIF5 |
| EIF2AK3 | EIF4B | EIF3C | EIF5A |
| EIF2AK4 | EIF4E | EIF3CL | EIF5A2 |
| EIF2B1 | EIF4E1B | EIF3D | EIF5AL1 |
| EIF2B2 | EIF4E2 | EIF3E | EIF5B |
| EIF2B3 | EIF4E3 | EIF3F | EIF6 |
| EIF2B4 | EIF4EBP1 | EIF3G | EIF3H |

DLBCL is caused by the abnormal multiplication of B-cells, which are very important parts of the lymphatic immune system. Like in other human cancers, this abnormal increase in the cell number of specific cells has detrimental effects on the body—leading eventually to the death of affected patients. Because the lymphatic system includes a great variety of different cell types the to be investigated B-cells have to be first of all isolated to be analyzed:

Cell suspensions from three biopsy specimens were separated by means of flow cytometry into a CD19+ malignant subpopulation and a CD19− nonmalignant subpopulation. Before the gene expression of the isolated B-cells could be investigated by microarray analysis, the RNA samples had to be prepared: Gene expression profiling was performed after two rounds of linear amplification from total RNA. To interpret the microarray results regarding gene expression the following adaptations were performed: After normalization to a median signal of 500, provided in the Affymetrix Microarray Suite software, version 5.0 (MAS5.0, Affymetrix, USA), genes were selected that had a signal value greater than 128 in either the CD19+ or CD19− fractions in at least two of the sorted samples.

The $1^{st}$ quartile, Median and $3^{rd}$ quartile refers to the cut off level for distinguishing high and low expression (see also FIG. 13-17 and Table 6). This means that a patient with an eIF expression higher than the $1^{st}$ quartile has a higher eIF expression than the lowest eIF expressing quarter of the complete range of patients tested. In contrast, a patient with an eIF expression higher than the $3^{rd}$ quartile has an eIF expression higher than three quarters of the tested patients (therefore a very high expression). To define significance a p-value of 0.05 was defined as significant.

Cell Culture

The lymphoma cell lines U-2932, RI-1, KARPAS 422, SU-DHL-4, OCI-Lyl, SU-DHL-10, NUDUL-1, SU-DHL-6 (all six DLBCL), Raji, BL2 (both Burkitt's lymphoma (BL)) and the spontaneously immortalized B-cell line MUG-CC1-LCL, derived from the tissue of a non-neoplastic donor as normal control, were grown in culture flasks and after one week of culture harvested by centrifugation. The pellets were washed with PBS buffer, the supernatant was discarded and the cell pellets stored at −80° C. until further usage.

Cell pellets were homogenized using NP40-lysis buffer. The lysate was centrifuged for 10 minutes at 10 000 rpm and 4° C. Protein concentration of the resulting supernatant was determined with the Bradford protein assay and was adjusted to 3 μg/μL with SDS-Sample Buffer. Samples were stored at −80° C. until further usage.

Immunohistochemistry

Antibodies for immunohistochemistry were diluted as follows: 1:750 (eIF3c) and 1:500 (eIF-2a). To score the stainings only intensity and no density scores were used. No staining was termed as "0", weak staining as "1", moderate staining as "2" and strong staining as "3". We analyzed the staining in tonsil tissue from patients suffering from chronic tonsillitis (non-neoplastic control) and lymph node tissue from patients suffering from DLBCL. Thereby we distinguished in the case of tonsils between the histological regions "mantle zone" and "germinal center" (with its centroblast and centrocyte cell type). Centroblasts are believed to be the progenitors for lymphoma cells. In the case of the DLBCL tissue we only scored the neoplastic B-cells, which infiltrated the major part of the lymph node destroying the original architecture.

Results

As described above a previously published data set comprising gene expression and patient survival profiles in DLBCL (Lenz G et al.) was analyzed for correlations between eIF mRNA expression and patient survival.

Indeed, we detected for several eIF-subunits a link between altered expression and better or worse patient outcome. The expression/survival correlations are illustrated in FIG. 13-17.

In the case of 9 eIF-subunits there was even a significant correlation between lower subunit expression and better patient outcome. In contrast, for eIF-4E3 the data indicate that higher gene expression seems to be significantly more beneficial for patient survival. 10 further eIF-subunits showed expression-survival correlations too, which however were not statistically significant ($p > 0.05$).

The results of the survival analysis are summarized in Table 7.

TABLE 7

Results of the bioinformatic eIF expression-survival analysis. For the eIFs indicated at the left a correlation between altered mRNA expression (higher or lower expression compared to the rest of the patient population) and patient outcome was detected (see also FIG. 13-17). For example, a lower expression of the eIF2AK4-mRNA than the $3^{rd}$ quartile seems to be better for patient survival.

|  | Gene | $1^{st}$ quartile | Survival analysis Median | $3^{rd}$ quartile |
|---|---|---|---|---|
| eIF cascade | eIF2AK4 |  |  | p = 0.069; low better |
|  | eIF2AK3/HsPEK |  | p = 0.096; high better |  |
|  | eIF2B4 |  | p = 0.057; low better |  |
|  | eIF2C 3 | p = 0.021; low better |  |  |
|  | eIF2d |  |  | p = 0.013; low better |
|  | eIF-2α |  |  | p = 0.014; low better |
|  | eIF2S2 |  |  | p = 0.009; low better |
|  | eIF3b |  |  | p = 0.020; low better |
|  | eIF3c |  | p = 0.031; low better |  |
|  | eIF3d |  |  | p = 0.031; low better |
|  | eIF3f |  |  | p = 0.065; low better |
|  | eIF3g | p = 0.071; low better |  |  |
|  | eIF3l |  |  | p = 0.043; low better |
|  | eIF-4B |  |  | p = 0.075; low better |
|  | eIF-4E3 |  |  | p = 0.016; high better |
|  | 4E-BP1 |  | p = 0.052; low better |  |
|  | eIF-4G1 | p = 0.060; low better |  |  |
|  | eIF-5A |  |  | p = 0.080; low better |
|  | eIF-5 | p = 0.077; high better |  |  |

To investigate eIF expression in lymphoma cells also in comparison with healthy B-cells, we performed cell culture studies comparing the immortalized B-cell line MUG-CC1-LCL (non-neoplastic control) with 8 lymphoma cell lines.

Figure 18:
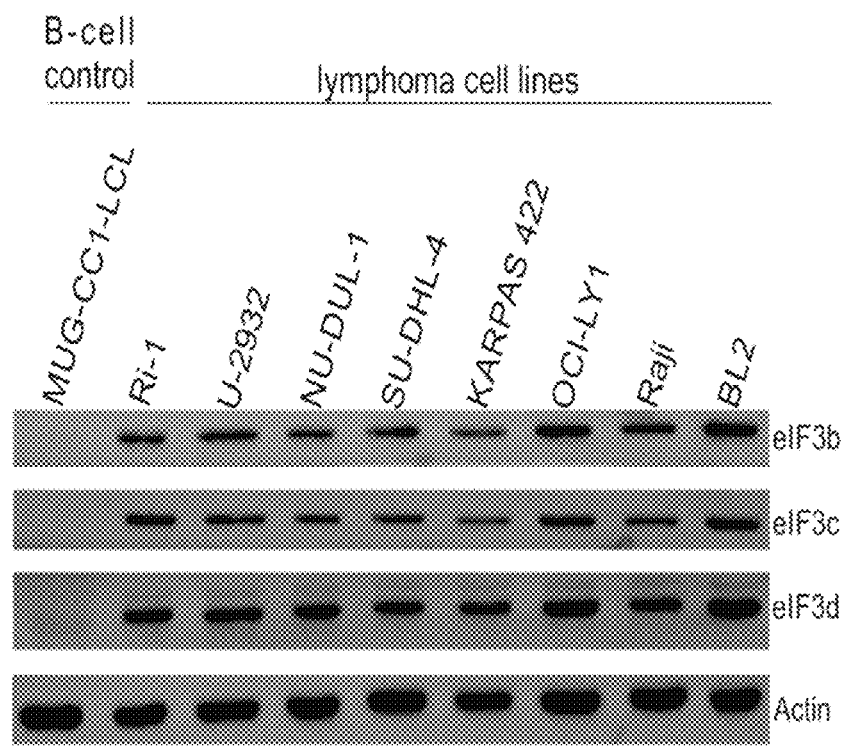
FIG. 18 shows the eIF expression comparison between an immortalized B-cell line (MUG-CC1-LCL) and eight lymphoma cell lines (Ri-1, U-2932, NU-DUL-1, SU-DHL-4, KARPAS 422, OCI-LY1, Raji and BL2). Actin expression was used as a loading control.
Figure 19:
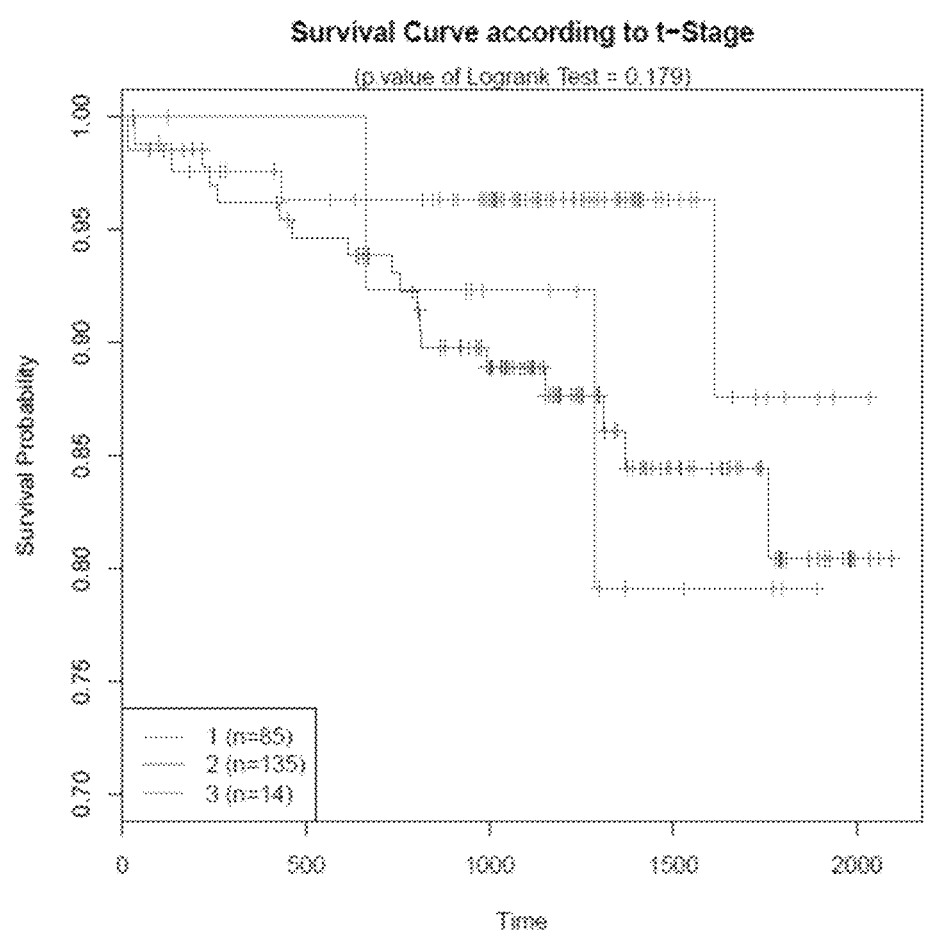
FIG. 19 shows Kaplan Meier Curves, in particular of HCC patients. Survival curve according to t-stage; 14 patients with a score of 3, 135 patients with score 2 and 85 patients with a score of 1. The survival is better with a lower score compared to a score of 3.
Figures 20A, 20B:
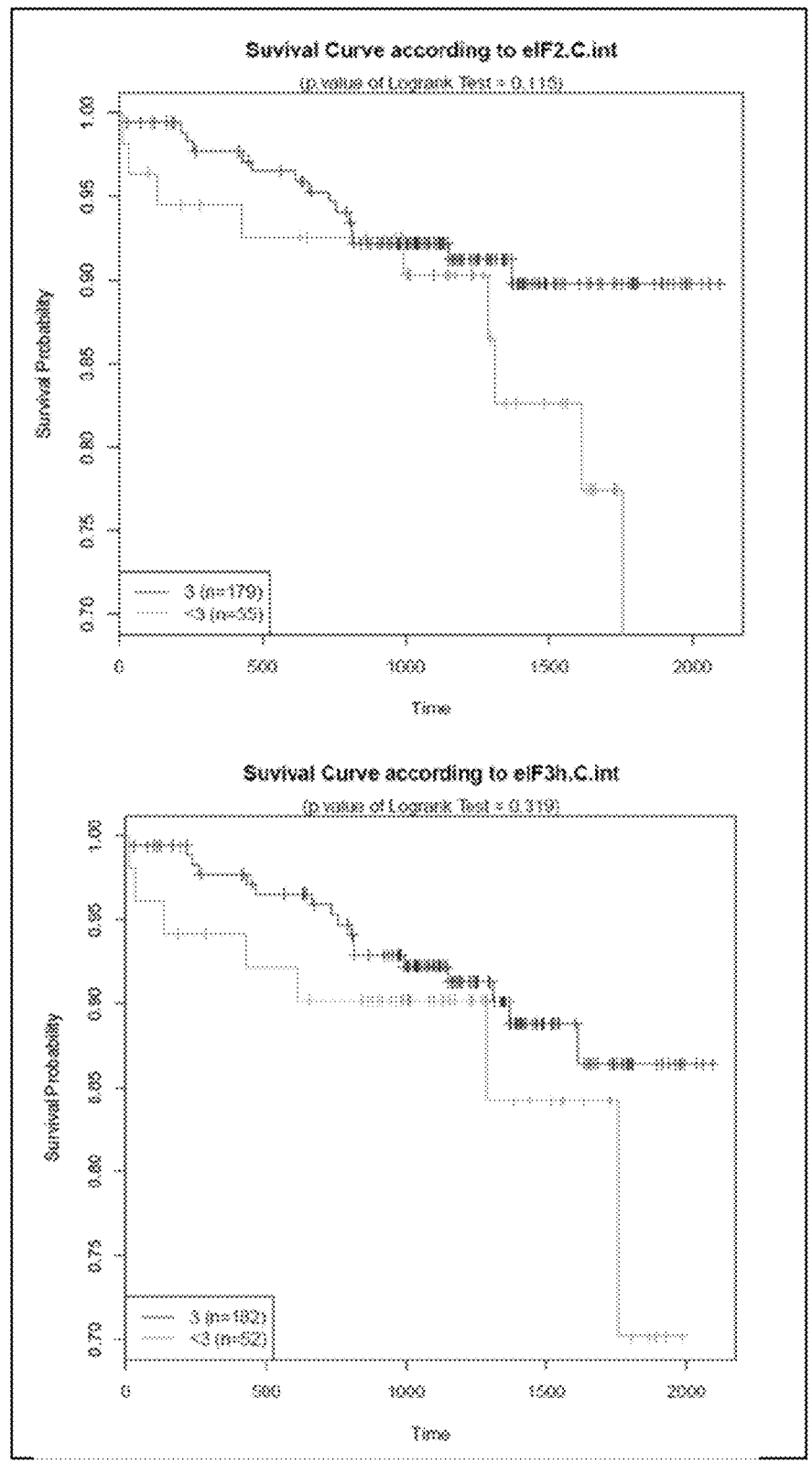
FIGS. 20A-20B shows Kaplan Meier Curves, in particular of HCC patients, to various eIFs.
Figure 23A:
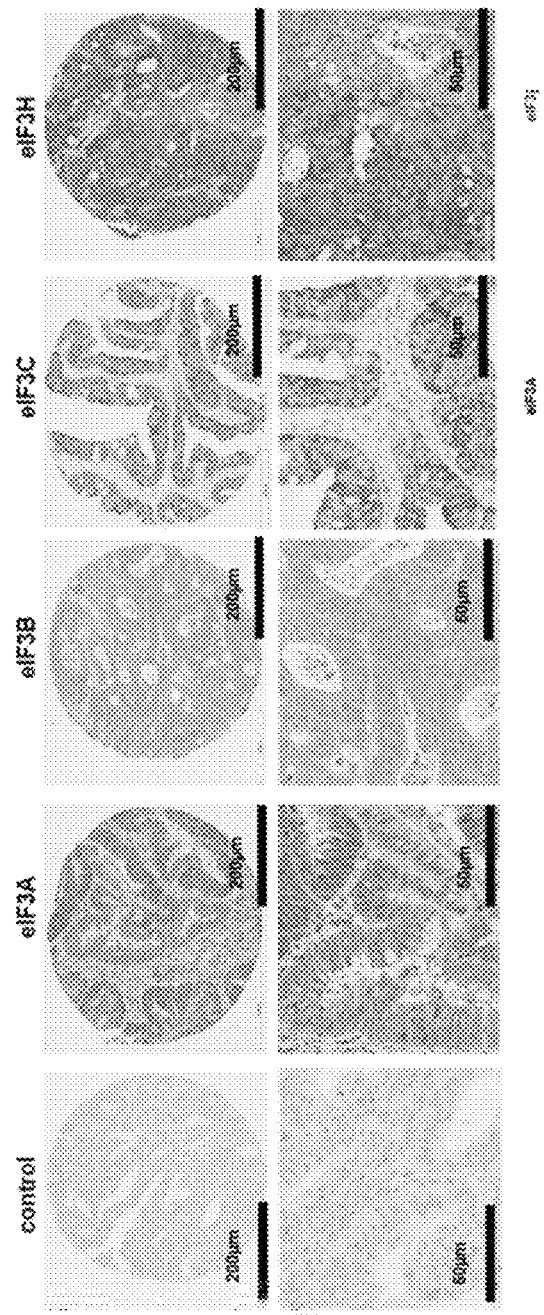
FIGS. 23A-23C shows expression of eIF3 subunits in CRC. [A and B] Significant increase of protein level for eIF3A, eIF3B, eIF3B, eIF3D and eIF3M in CRC samples compared to normal mucosa. Protein expression of eIF3C, eIF3j and eIF3K is significantly upregulated in RC compared to CC and healthy tissue. [C] mRNA expression of eIF3A, eIF3B and eIF3j show an overexpression in RC compared to CC samples. eIF3H and eIF3M overexpressed in CC compared to RC. mRNA expression of eIF3C and eIF3j show an overexpression in RC compared to CC samples. eIF3C show no significant differences on mRNA level in CRC. In particular.
Figure 23B:
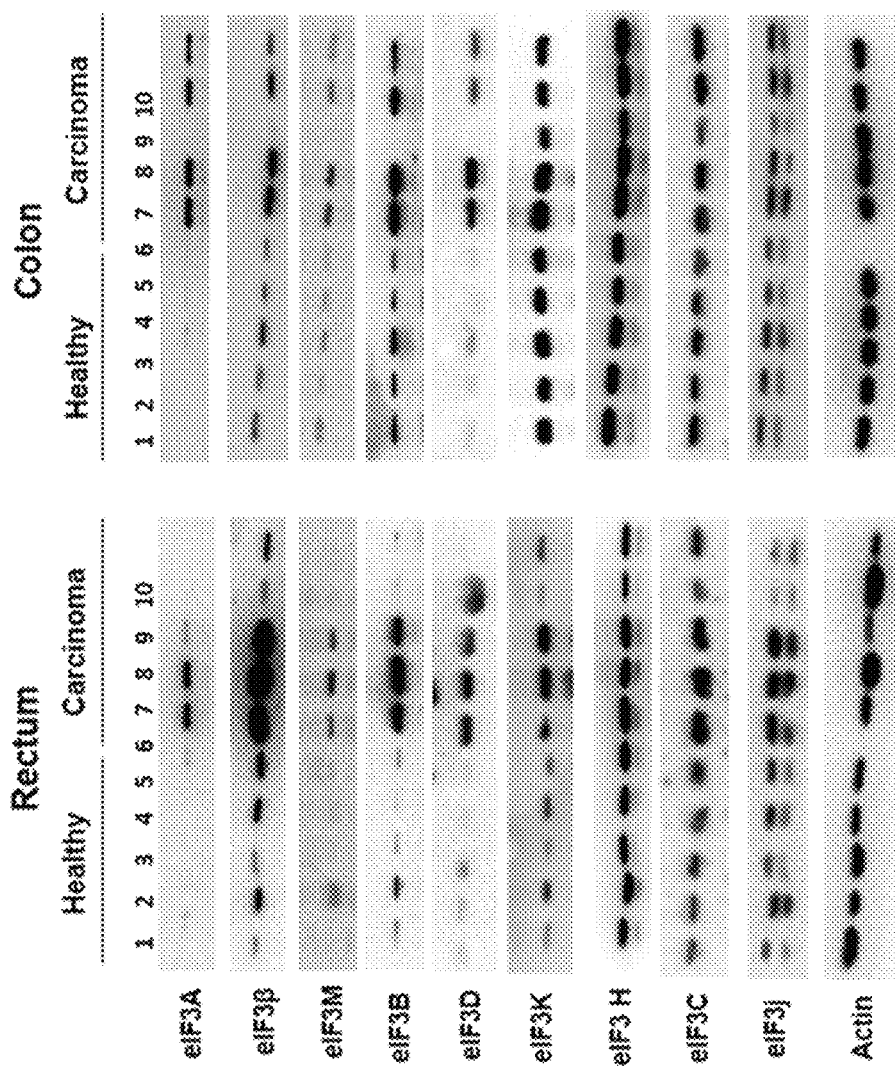
Figure 23C:
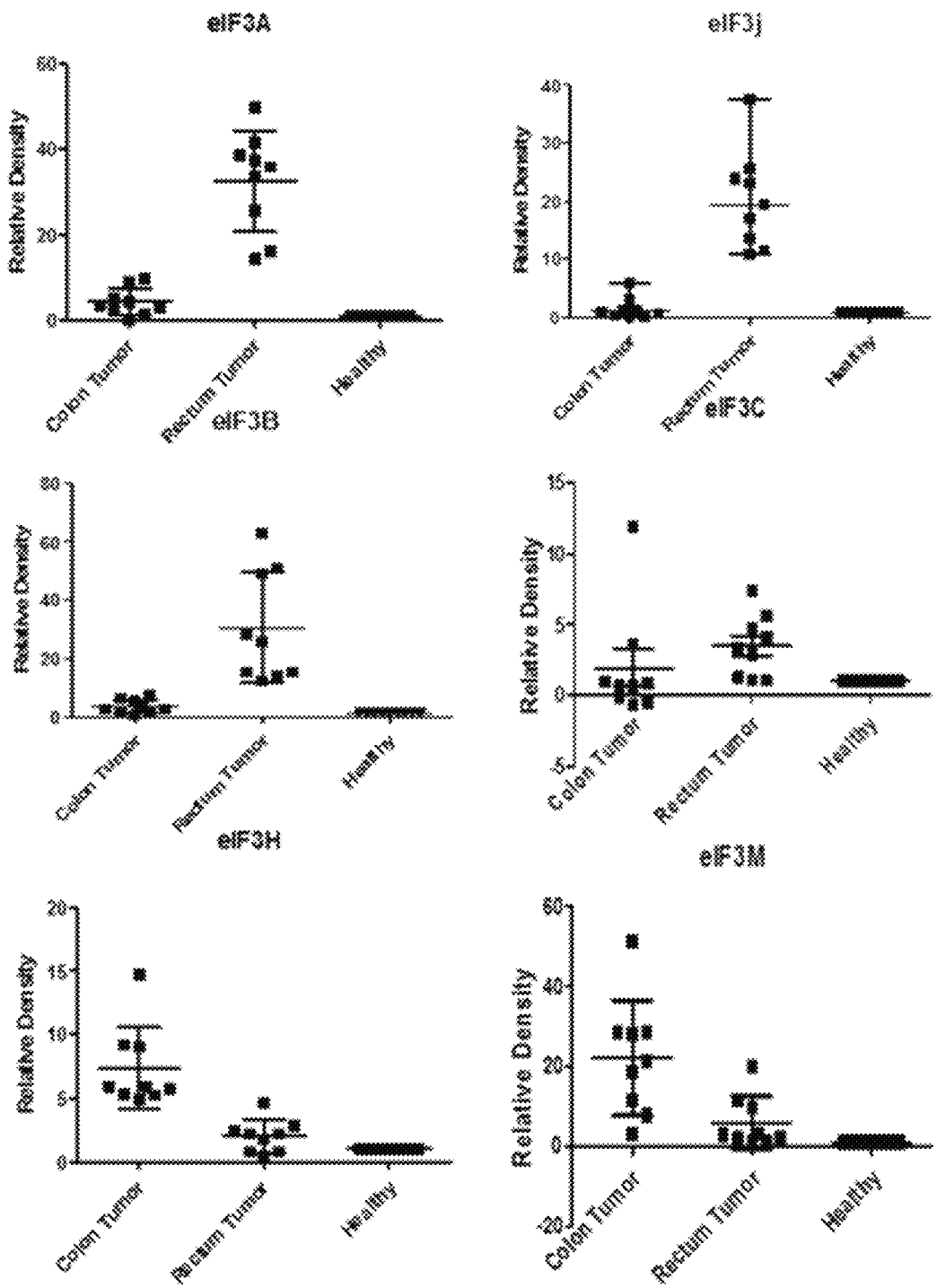
Figure 24A:
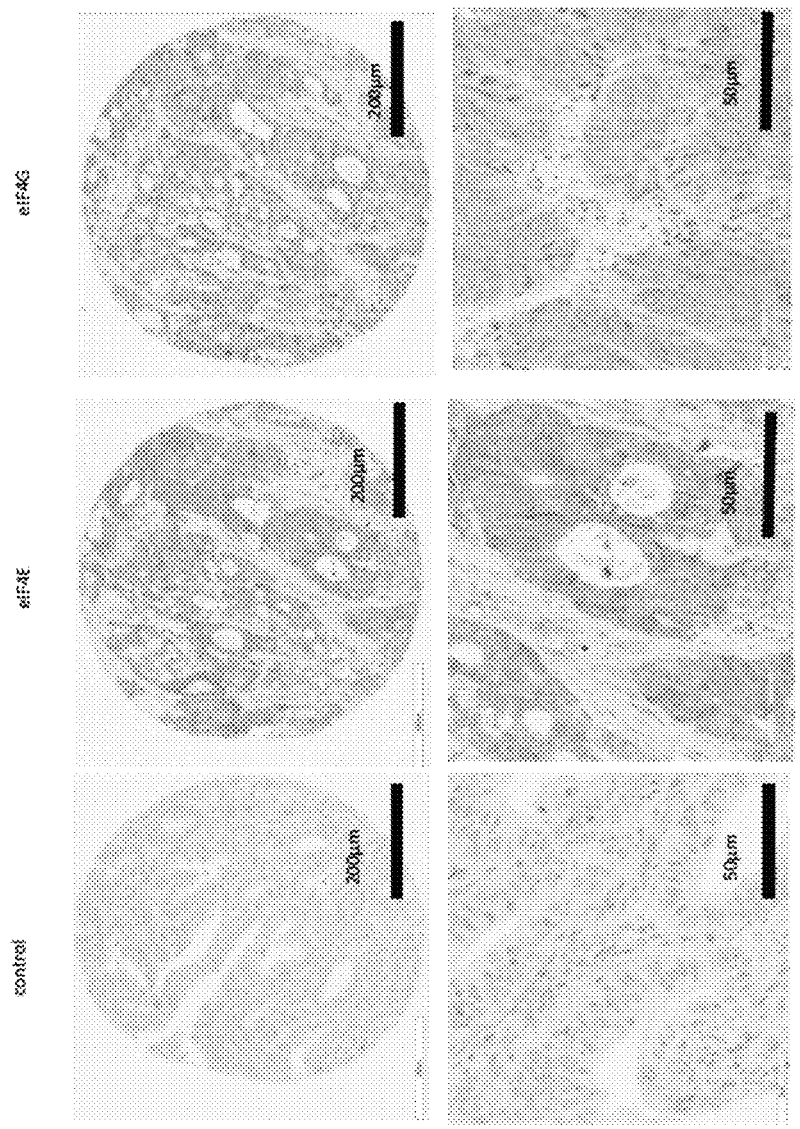
FIGS. 24A-24C shows expression of eIF4 subunits in CRC.
Figure 24B:
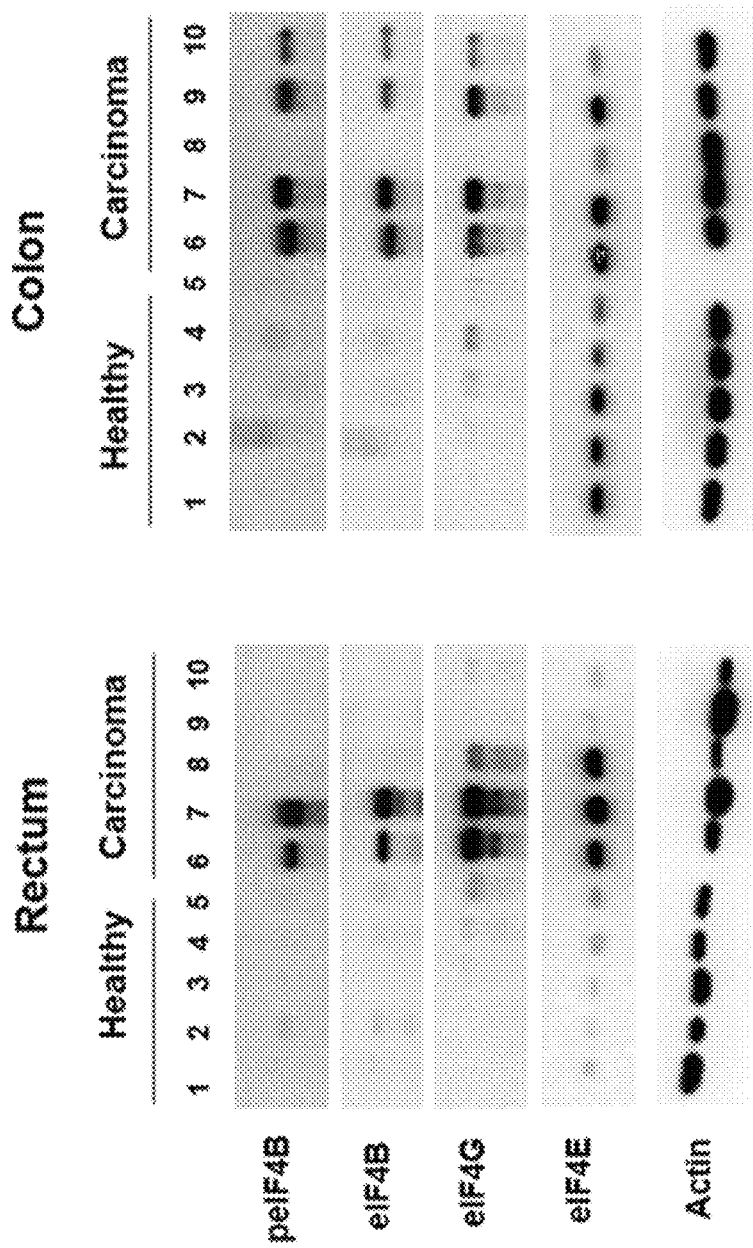
Figure 24C:
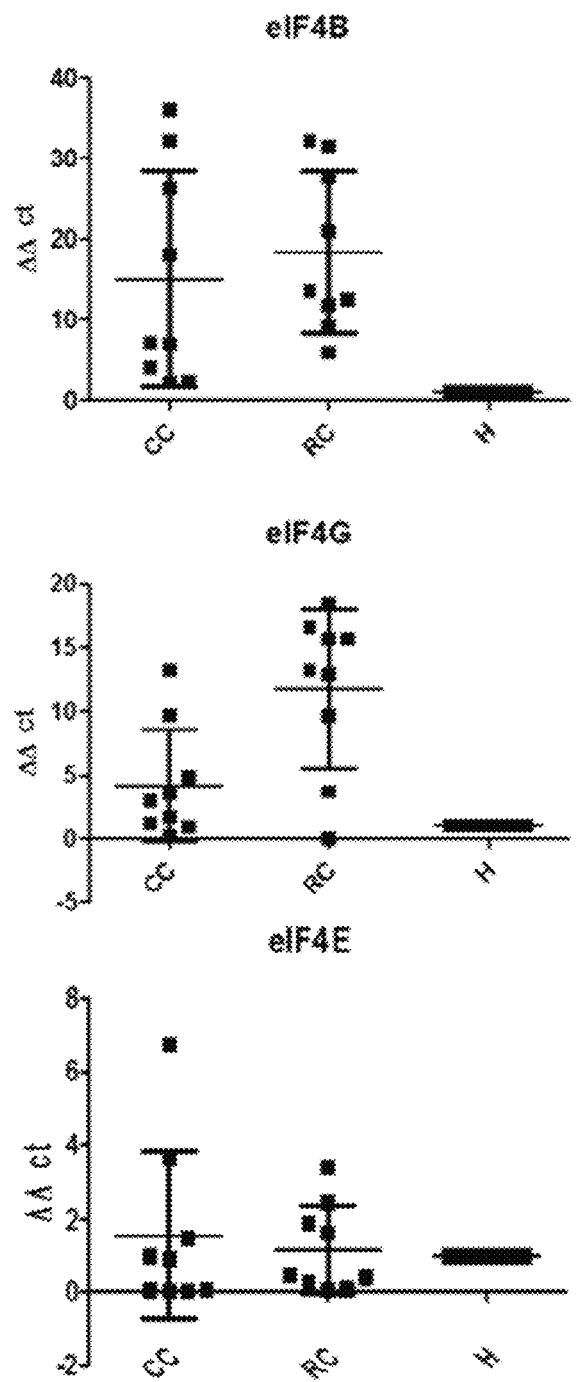
Figure 25A:
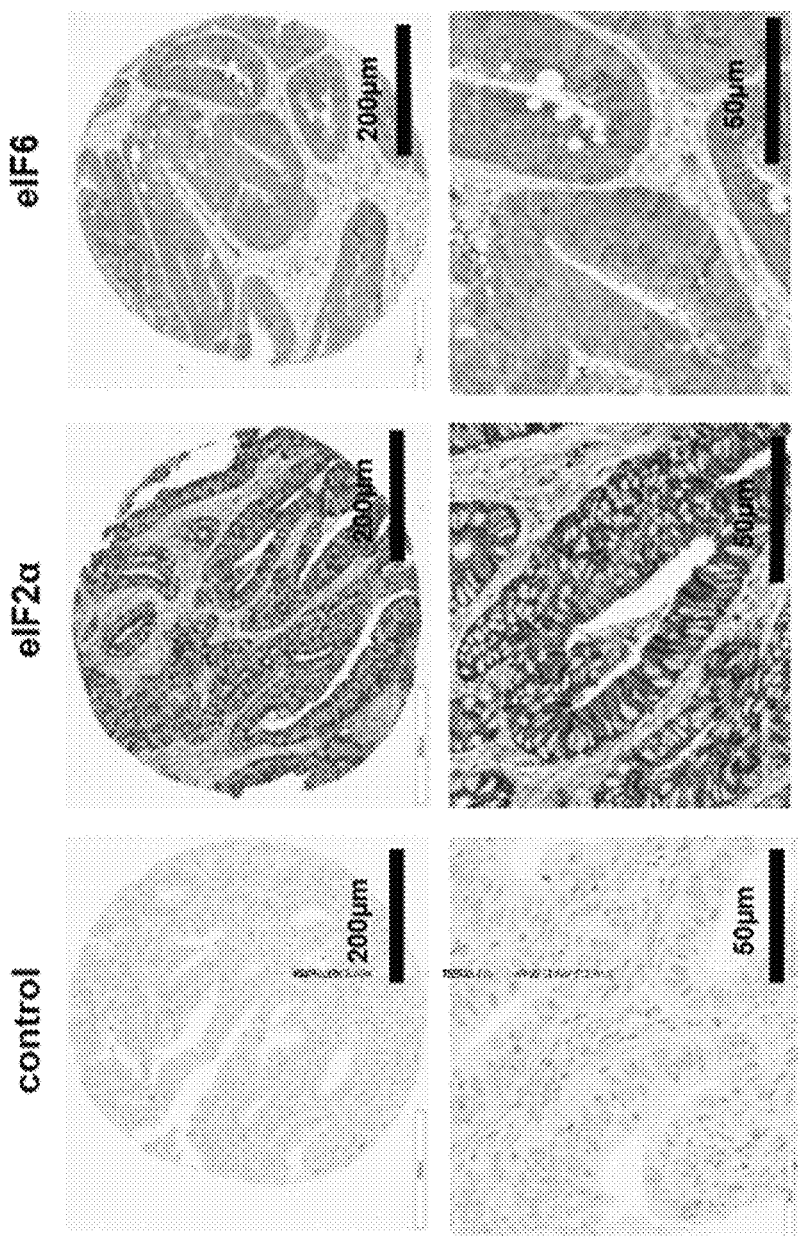
FIGS. 25A-25C shows expression of peIF2α, eIF2α, eIF5 and eIF6 in CRC.
Figure 25B:
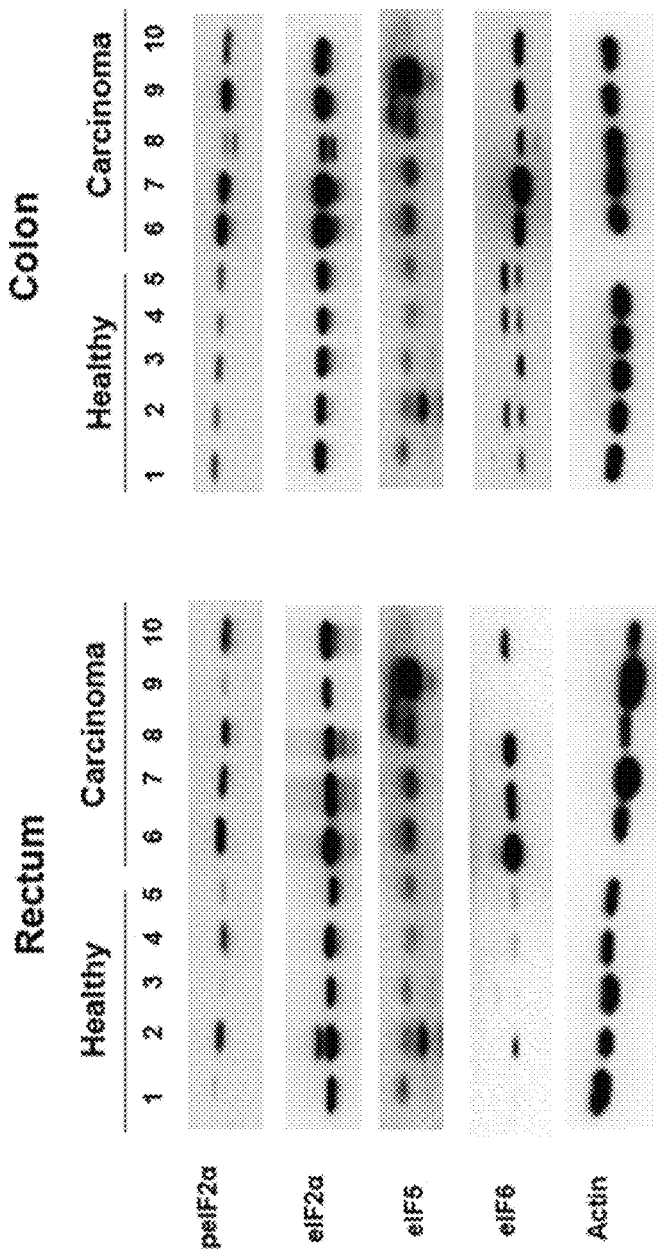
Figure 25C:
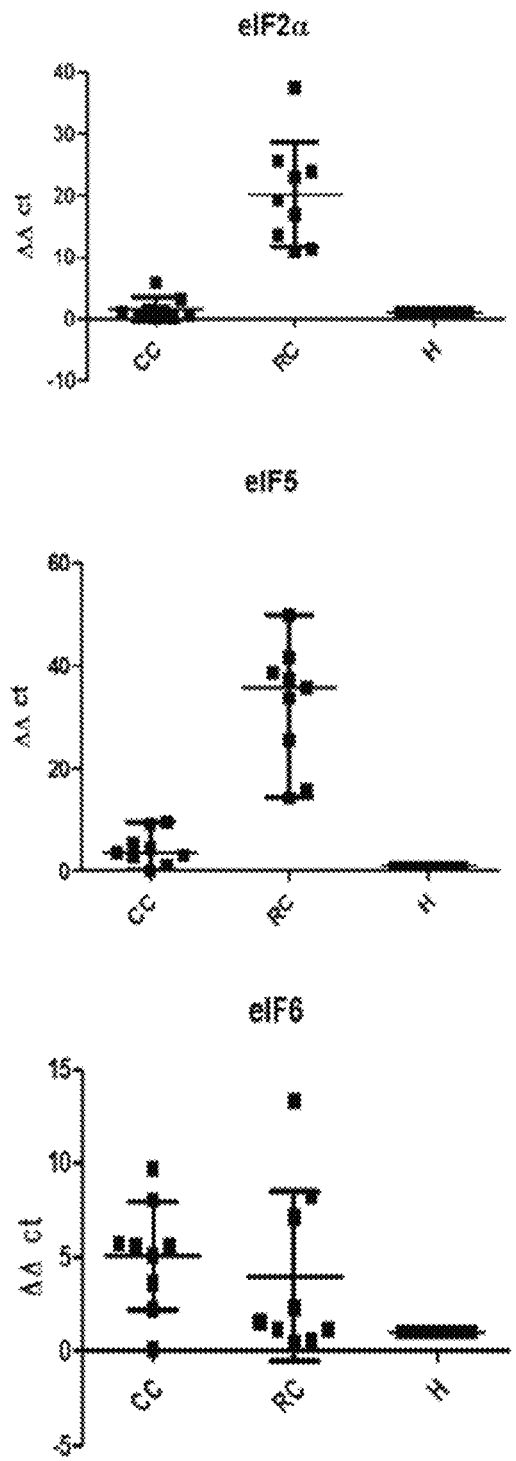
Figure 26:
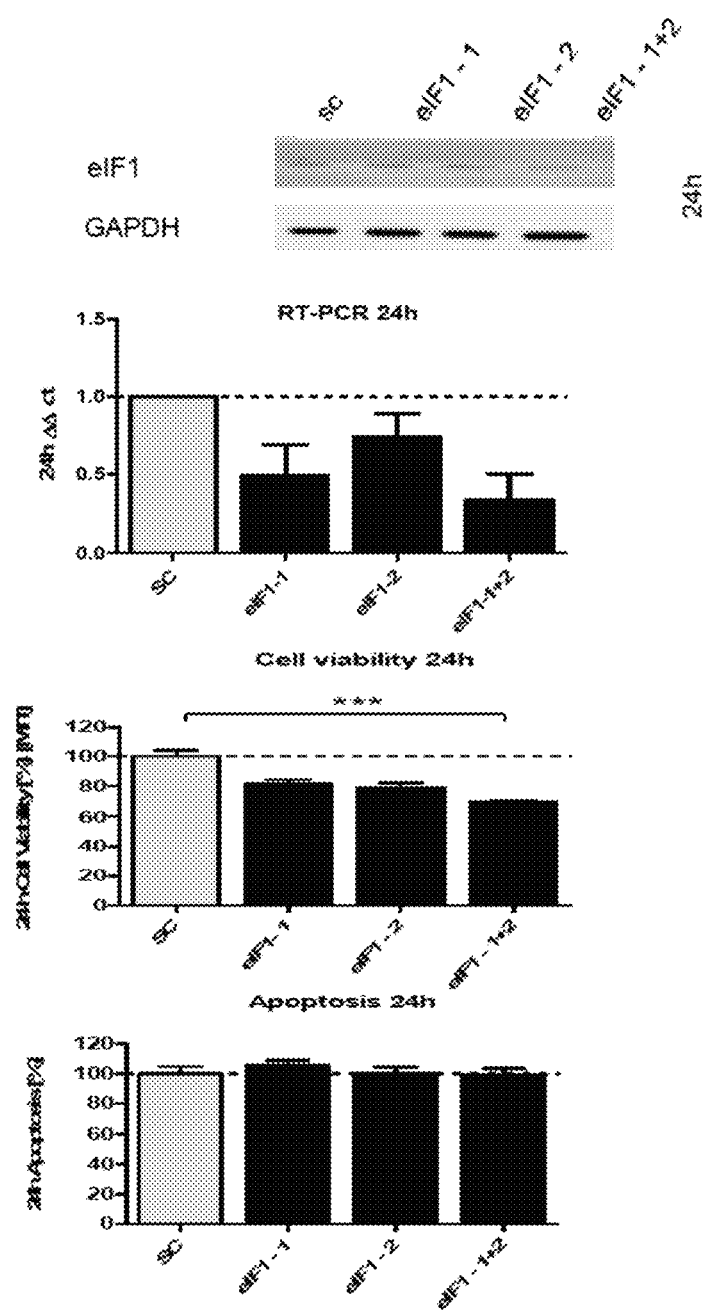
FIG. 26 to 28 show the eIF1, eIF5 and eIF6 silencing
Figure 26:
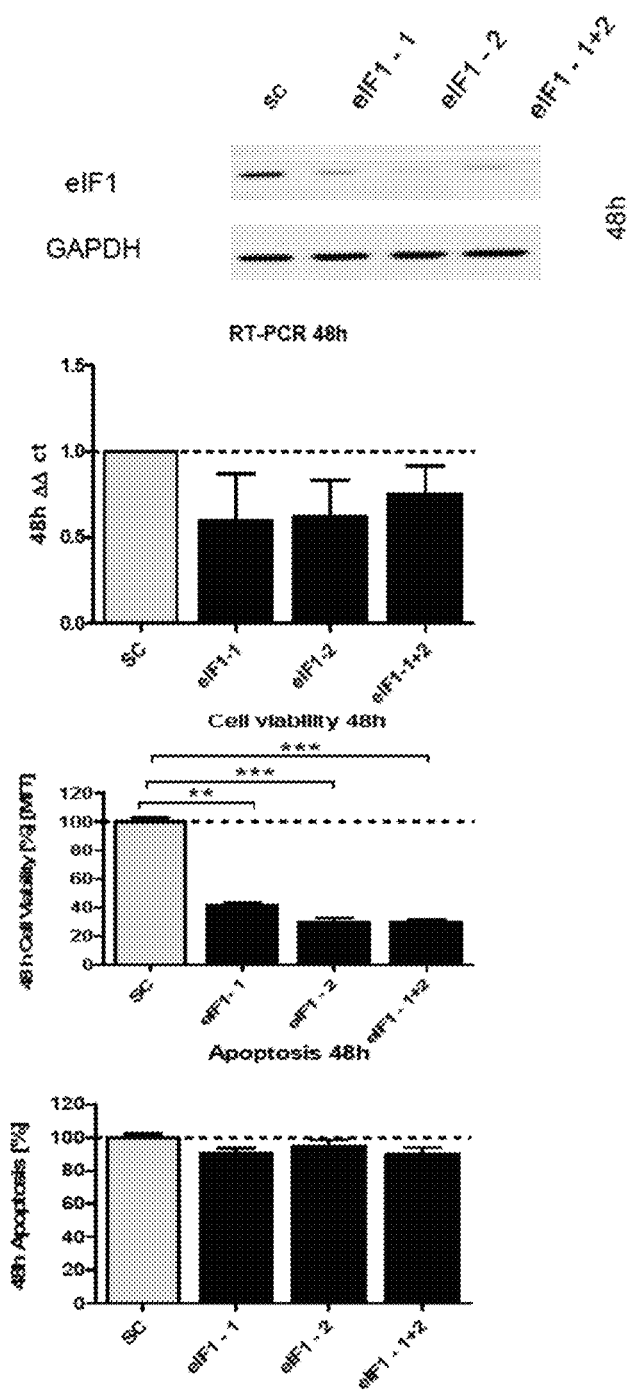
Figure 26:
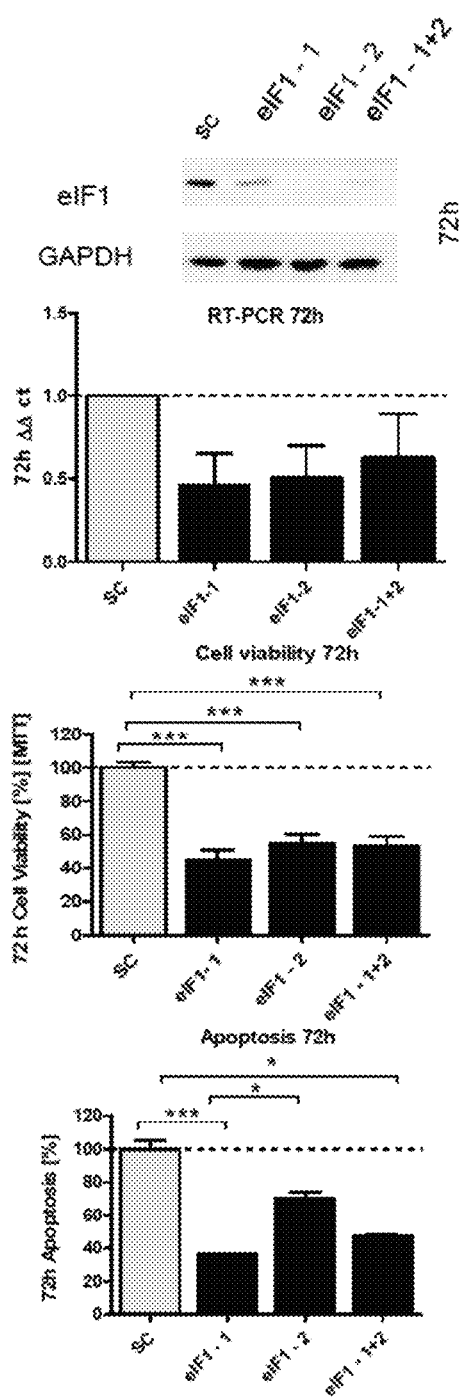
Figure 27:
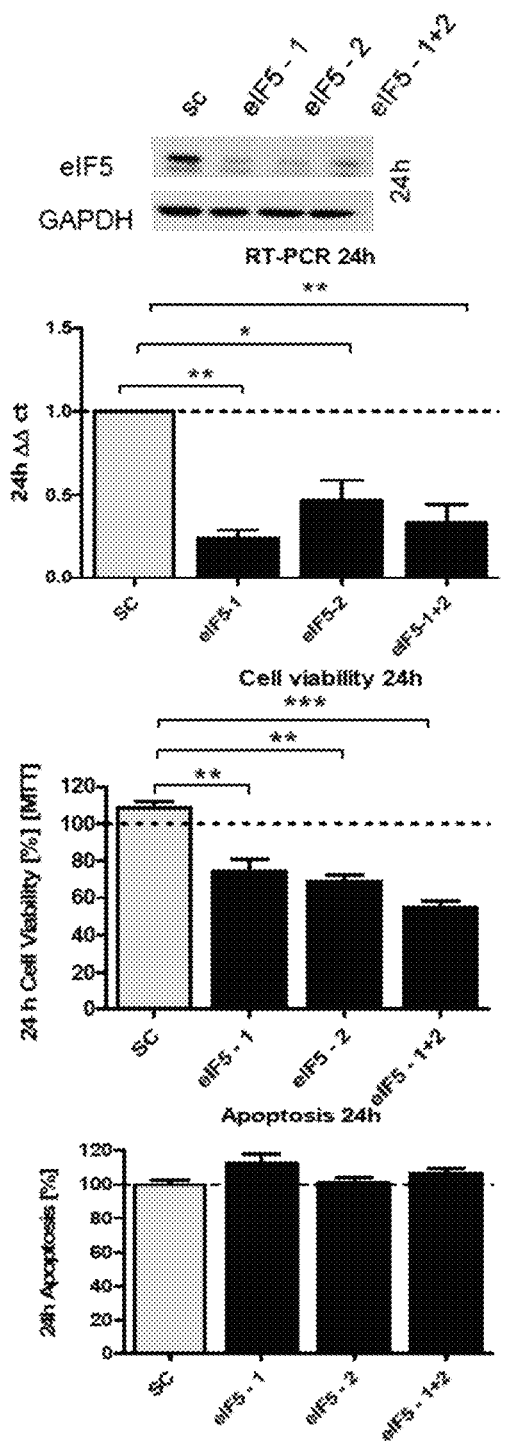
Figure 27:
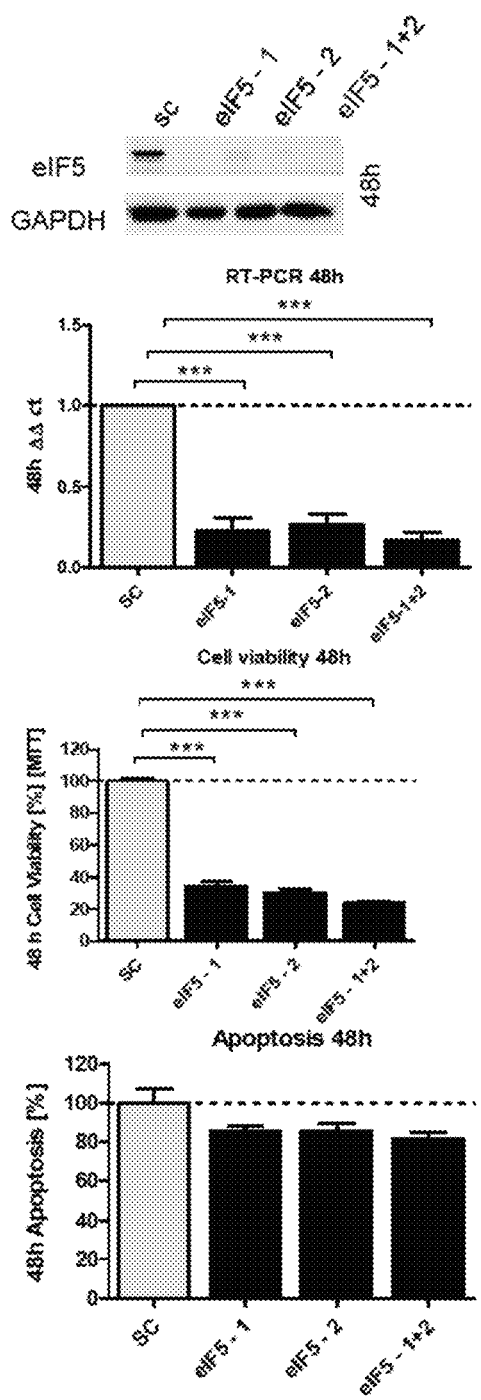
Figure 27:
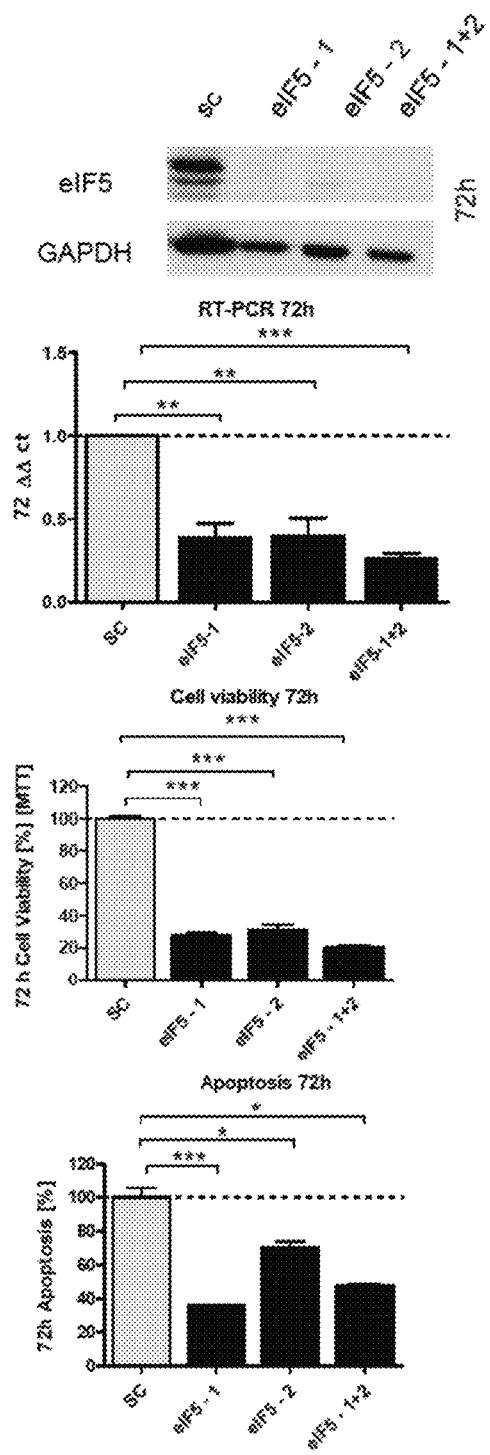
Figure 28:
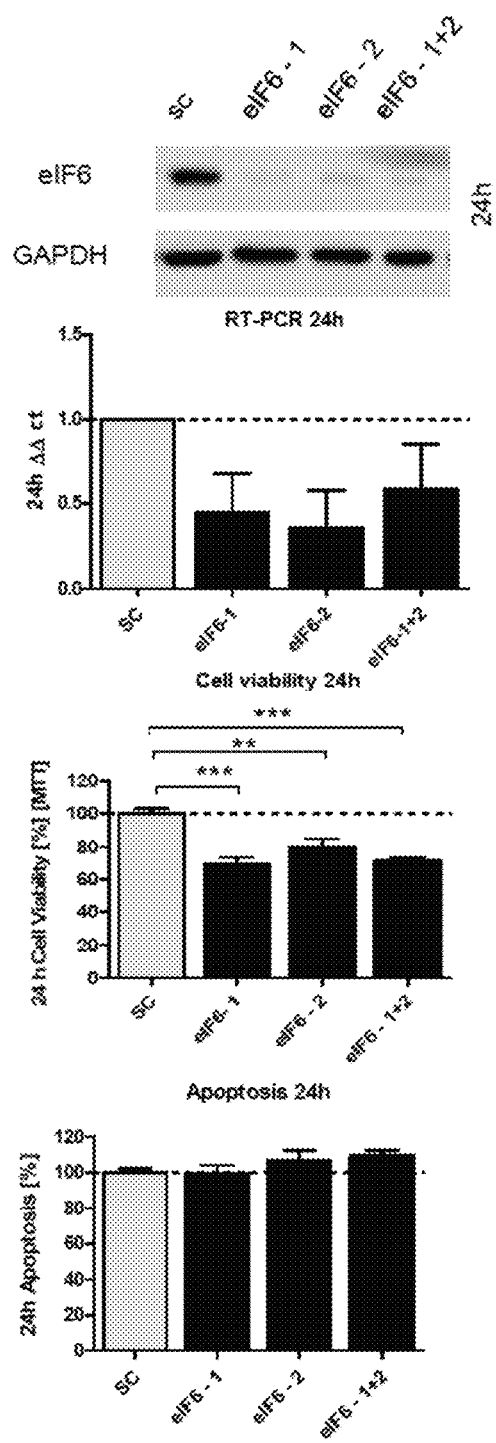
Figure 28:
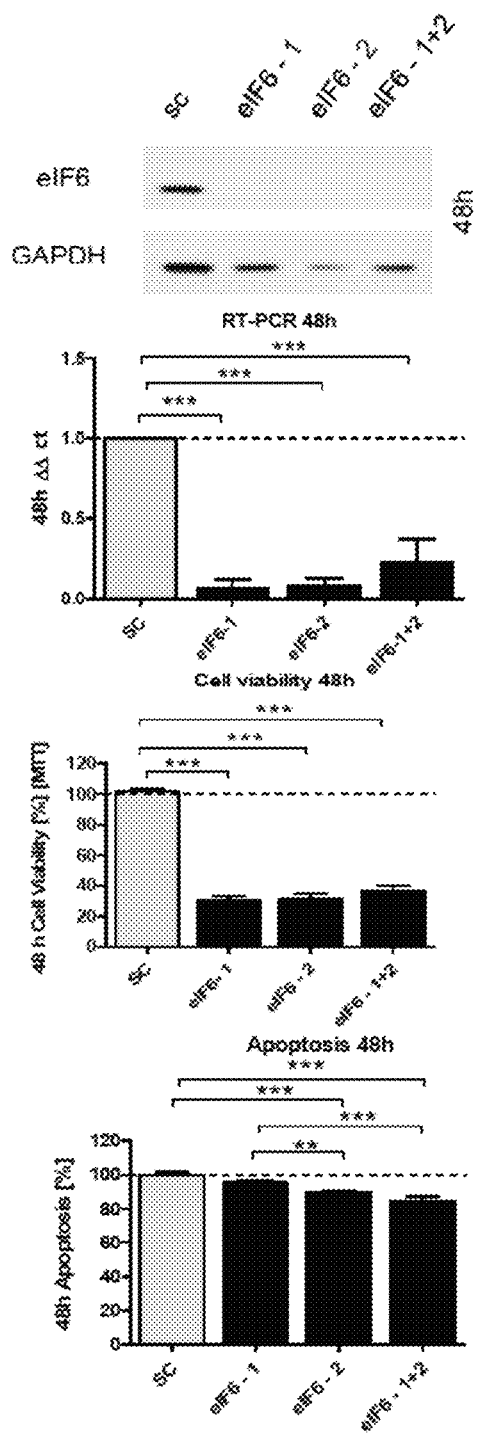
Figure 28:
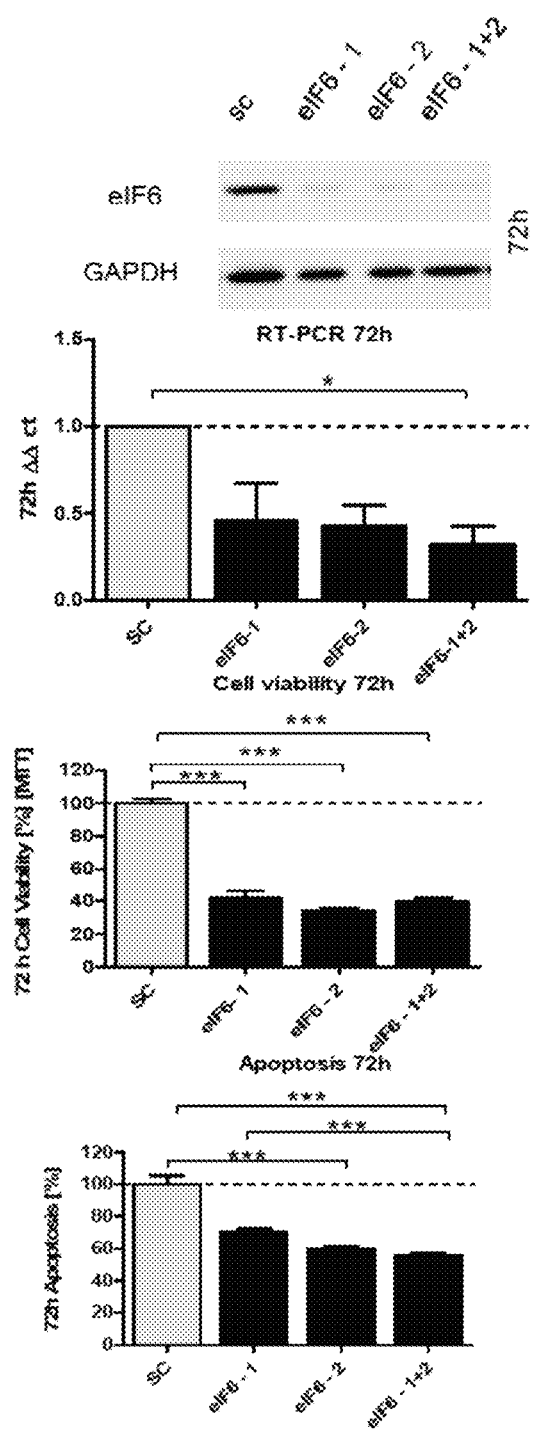
Figure 29C:
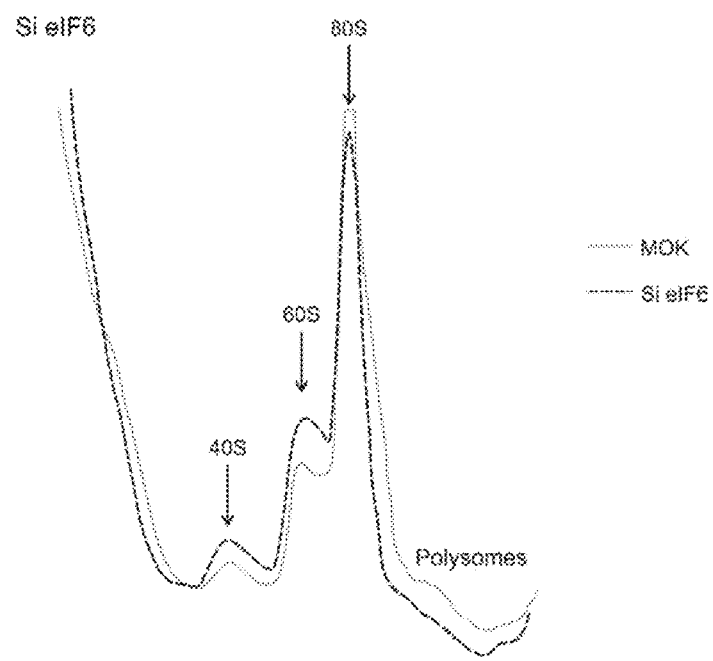
Figure 30A:
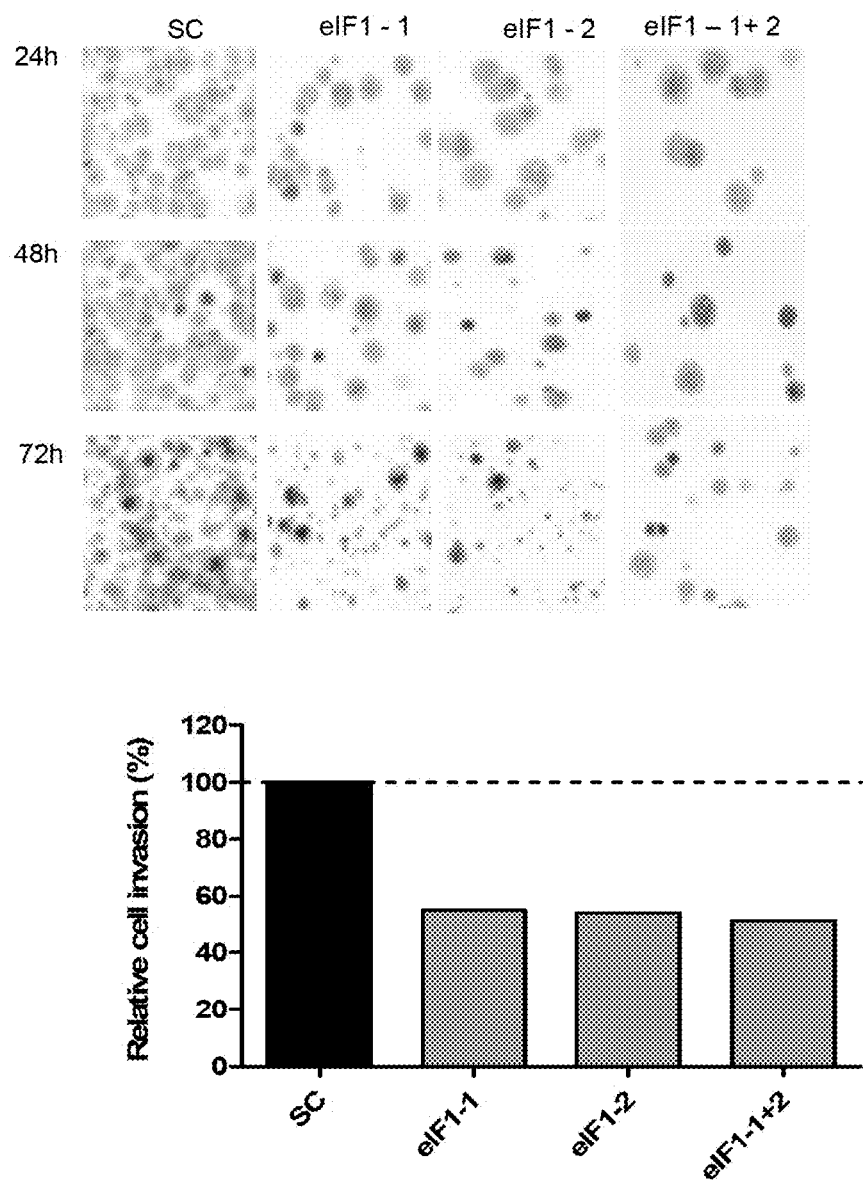
FIGS. 30A and 30B shows colony assays of eIF1 and eIF5. In particular.
Figure 30B:
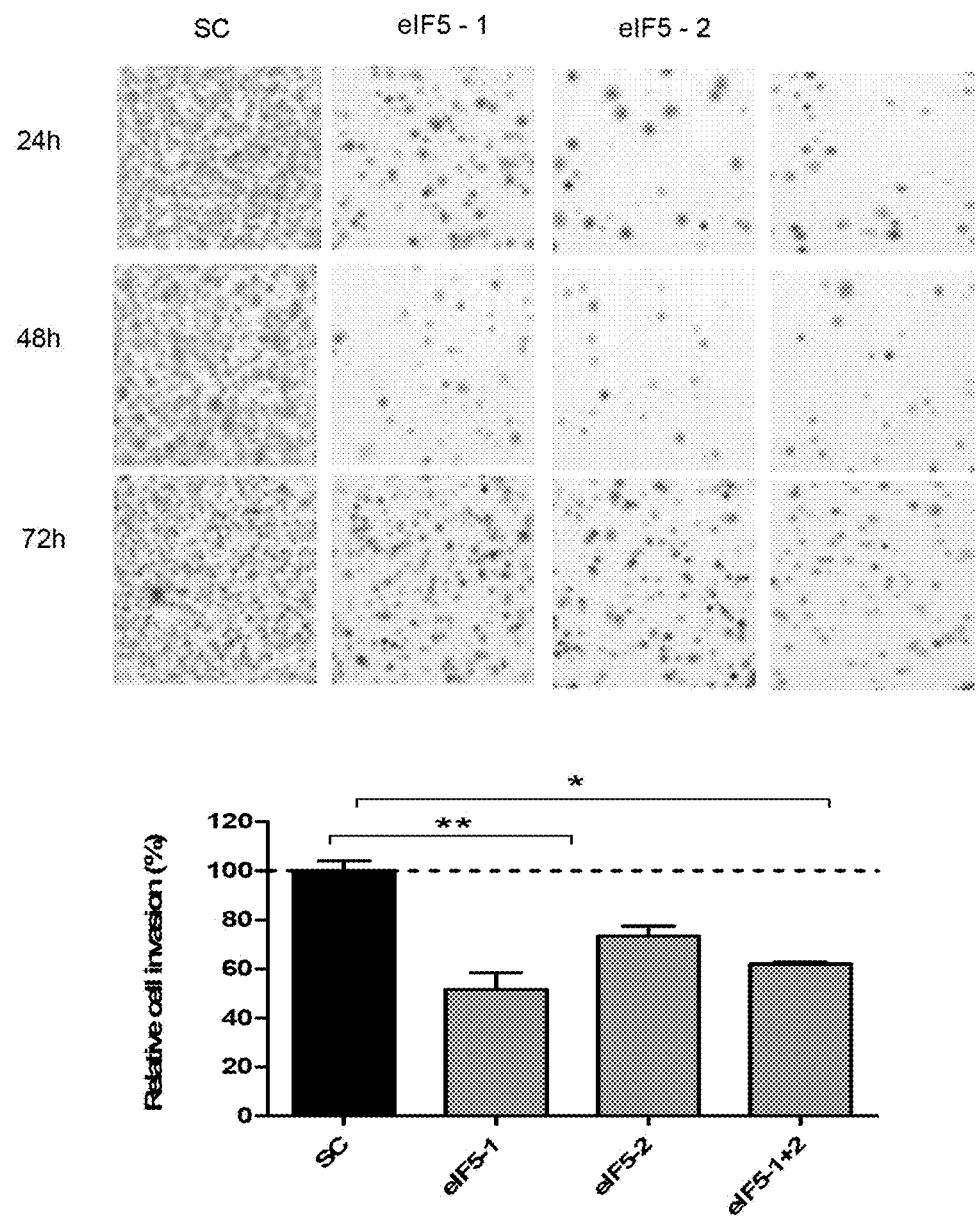
Figure 31:
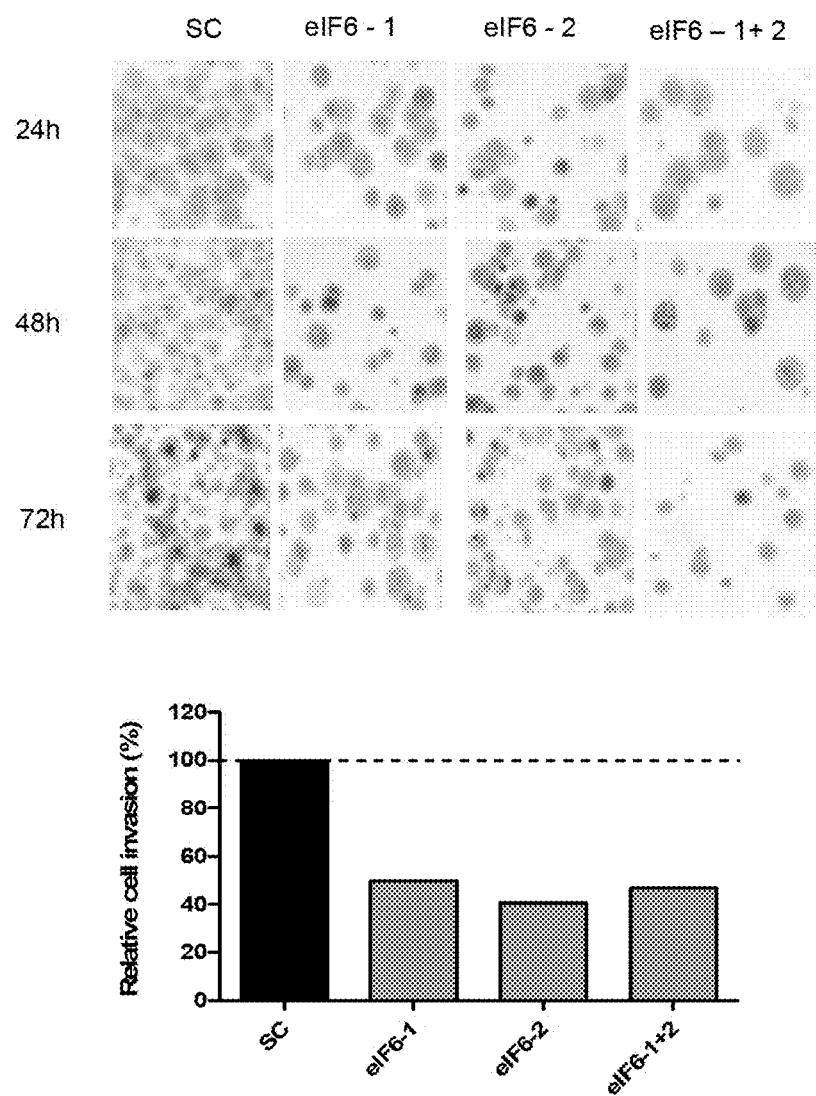
FIG. 31 shows colony assays of eIF6. In particular, it shows the effect of eIF6 knockdown on invasiveness and clonogenicity in HCT 116 cells. Clonogenicity is dramatically reduced at all three time points after eIF6 knockdown in HCT 116 cells compared to the scrambled control cell. The decrease in transmigrating cells after transfection with eIF6 siRNA constructs is significant in HCT116 cells. Statistical analyses: 1-way ANOVA with Bonferroni post-test $*p<0.05$, $p<0.01$ and $*p<0.001$.
Figure 32:
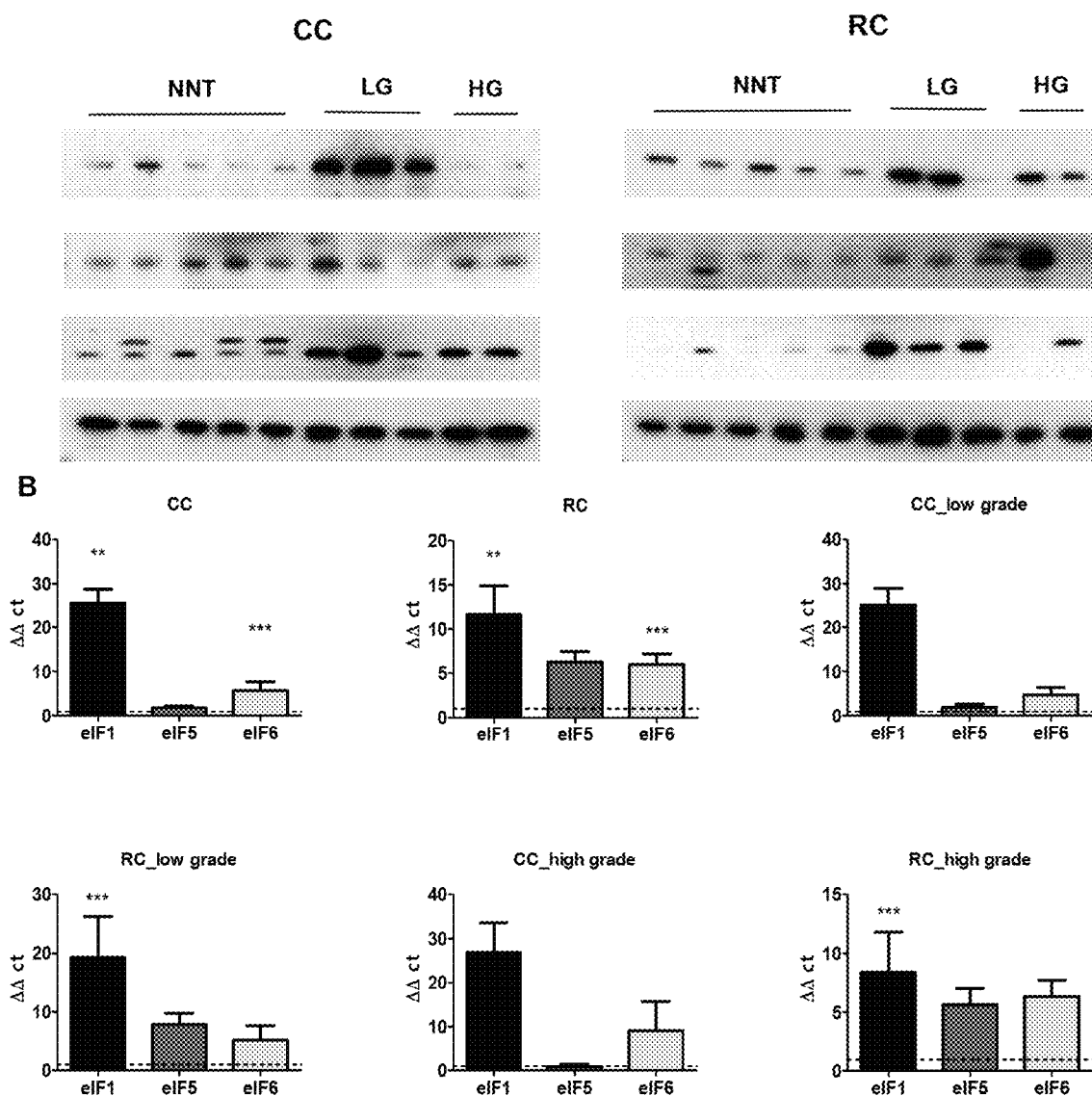
FIG. 32 shows eIF1, eIF5 and eIF6 expression levels in low and high grade colon and rectum carcinomas. [A] Western blot of eIF1, eIF5 and eIF6 from low grade (LG) and high grade (HG) colon carcinomas (CC) and rectum carcinomas (RC) compared to non-neoplastic tissues (NNT). Equal amounts of protein from each pair are resolved on SDS PAGE and immunoblotted with antibodies directed against eIF1, eIF5, eIF6 and R-actin (loading control). [B] qRT-PCR of eIF1, eIF5 and eIF6 from LG and HG CC and RC compared to non-neoplastic tissues (NNT). Error bars show SEM.

We investigated protein expression of three eIF candidates, which were already in the survival analysis shown to be involved in lymphoma biology: eIF3b, eIF3c and eIF3d. As illustrated in FIG. 18, compared to the non-neoplastic control, the expression of all three tested eIFs was markedly increased in the 8 lymphoma cell lines.

In addition, we also analyzed eIF expression in DLBCL patient samples and non-neoplastic control tissue (tonsils) using immunohistochemistry (preliminary data). The results are depicted in Table 8 and Table 9 and show that the analyzed eIFs (eIF3c and eIF-2α) could be detected by using immunohistochemistry. Regarding the scorings, the eIF staining was far more prominent in the germinal center than in the surrounding mantle zone (non-neoplastic tonsils). Having a closer look on the DLBCL patient tissue, the expression of the eIFs varied between the distinct DLBCL-patients, indicating that there is indeed a person-specific eIF expression pattern.

TABLE 8

Immunohistochemical staining of eIF3c in non-neoplastic tonsils and neoplastic lymph nodes infiltrated with a DLBCL. The centroblasts are believed to be the progenitor cells for DLBCL and therefore one has to focus on their staining intensity within germinal centers.

|  | eIF3c | | |
|---|---|---|---|
|  |  | Germinal center | |
| Non-neoplastic tonsils | Mantle zone | Centroblasts | Centrocytes |
| T1 | 0 | 2 | 0.5 |
| T2 | 0 | 1 | 0.5 |
| T3 | 0 | 1.5 | 0.5 |
| T4 | 0 | 2 | 1 |
| T5 | 0 | 3 | 1 |
| T6 | 0 | 3 | 1.5 |

TABLE 8-continued

Immunohistochemical staining of eIF3c in non-neoplastic tonsils and neoplastic lymph nodes infiltrated with a DLBCL. The centroblasts are believed to be the progenitor cells for DLBCL and therefore one has to focus on their staining intensity within germinal centers.

| DLBCL | Neoplastic cells |
|---|---|
| D1 | 2 |
| D2 | 0 |
| D3 | 3 |
| D4 | 3 |
| D5 | 3 |
| D6 | 2.5 |
| D7 | 3 |
| D8 | 2 |
| D9 | 2 |
| D10 | 1 |
| D11 | 2.5 |
| D12 | 2 |

No staining was termed as "0", weak staining as "1", moderate staining as "2" and strong staining as "3".

TABLE 9

Immunohistochemical staining of eIF-2α in non-neoplastic tonsils and neoplastic lymph nodes infiltrated with a DLBCL. The centroblasts are believed to be the progenitor cells for DLBCL and therefore one has to focus on their staining intensity within germinal centers.

|  | eIF-2α | | |
|---|---|---|---|
|  |  | Germinal center | |
| Non-neoplastic tonsils | Mantle zone | Centroblasts | Centrocytes |
| T1 | / | 3 | / |
| T2 | / | 2 | / |
| T3 | / | 2.5 | / |
| T4 | / | 3 | / |
| T5 | / | 3 | / |
| T6 | / | 2 | / |

TABLE 9-continued

Immunohistochemical staining of eIF-2α in non-neoplastic tonsils and neoplastic lymph nodes infiltrated with a DLBCL. The centroblasts are believed to be the progenitor cells for DLBCL and therefore one has to focus on their staining intensity within germinal centers.

| DLBCL | Neoplastic cells |
|---|---|
| D1 | 3 |
| D2 | 1 |
| D3 | 3 |
| D4 | 3 |
| D5 | 2 |
| D6 | 2 |
| D7 | 3 |
| D8 | 3 |
| D9 | 3 |
| D10 | 1 |
| D11 | 2 |
| D12 | 3 |

No staining was termed as "0", weak staining as "1", moderate staining as "2" and strong staining as "3". "/" indicates that these tissue parts were not scored - in contrast to the immunohistochemical analysis of eIF3c.

Discussion

Till now, the research in the lymphoma area focused mainly on the eIF4F-complex. Therefore, research studies, investigating the complete range of eIFs, were lacking.

Through our survival analysis, cell culture studies and immunohistochemical investigations we detected a potential for in the field previously unstudied eIFs to serve as treatment targets in DLBCL (7-9 and FIGS. 13-17).

These findings could be directly translated into new treatment approaches for affected patients: First of all specific eIF levels could be analyzed by immunohistochemistry (Our immunohistochemical analysis showed that eIF detection in patient tissue samples is possible). Furthermore, the immunohistochemical analysis also indicated that eIFs seem to be more important for germinal center B-cells than for mantle zones. Germinal centers are the regions within lymphatic tissue where B-cells are trained and they are also believed to be the starting points at which the neoplastic DLBCL-cells develop. Therefore, the neoplastic DLBCL-cells could be more sensitive to induced expression alterations of eIFs than other lymphatic cellular subtypes.

Thus, the expression levels of specific eIFs, which we found to be worse for the patient's survival when higher expressed, could for example be reduced as a therapeutic approach. The results of our cell culture studies additionally strengthened the use of such treatment approaches by showing an abnormally increased eIF3b, eIF3c and eIF3d expression in lymphoma cells when compared to non-neoplastic B-cells. Also in the survival analysis, eIF3b, eIF3c and eIF3d were shown to be worse for the patient's outcome when higher expressed. Due to financial constraints we could only test the referred three eIFs of the survival analysis also on protein level in cell culture. However, the promising results indicate that lymphoma cells could be highly sensitive to expression reduction of these eIFs by being dependent on respective high expression levels. Normal, non-neoplastic B-cells with a lower basal eIF expression could be left undamaged by such approaches (at least with regard to this specific eIF subgroup). Investigations on silencing particular eIFs in cell culture are currently already planned in our laboratory.

Other eIFs, which are more beneficial for the patient at higher expression levels, could in contrast be upregulated. (Unfortunately, we could not test any member of this eIF group in our studies so far).

Such course of action would add an additional treatment strategy and thus broaden the treatment options of affected patients.

Example 4: Hepatocellular Carcinoma (HCC)

Materials and Methods

Human Hepatocellular Carcinoma Samples

Formalin fixed paraffin embedded HCC samples and respective healthy control tissues from a total of 234 patients were collected and were used to generate 10 tissue microarrays (TMAs). The histological diagnosis, differentiation, and stage were classified according to the WHO classification (Hamilton S et al. Pathology and Genetics of Tumors of the Digestive System. World Health Organization Classification of Tumours International Agency for Research on Canccer (IARC) 2000; IARC Press).

Results

Immunohistochemistry of Tissue Microarrays

Density of the IHC staining was predominantly evaluated as 100%. In comparison to healthy liver tissue, several eIFs were highly upregulated in HCC tissue.

IHC staining for eIF2α, eIF3H, eIF3C, eIF4E and eIF6 revealed a weak to strong staining in the Healthy liver tissue and also in the HCC tissue.

For eIF5 the IHC staining displayed a high to moderate staining intensity in the HCC samples, whereas the intensity in healthy liver tissue was weak.

Expression of eIF2α, eIF3C, eIF4E and eIF5 in HCC

Protein expression of eIF2α, eIF3C, eIF4E and eIF5 was significantly upregulated in HCC samples and HCC samples with a HCV infection compared to healthy liver tissue. The p-value for this calculation was 0.051.

Statistical Analysis

The Survival Curve according to t-Stage displayed a better survival with a lower score ≤2 than with a score of 3 with a p-value of 0.179. The survival is also better when the patient has one tumor compared to patients with two or more. Microvessel invasion is associated with a poor clinical outcome compared to patients without a microvessel invasion with a p-value of 0.067. The survival according to sex is better for women compared to man with a p-vale of 0.6. The differences between patients with and without a HBV (Hepatitis B virus) infection showed no changes in the survival of these patients. In comparison with HCV (Hepatitis C virus) patients the survival is poor compared to patients without HCV infection with a p-value of 0.036.

Discussion

Liver cancer is the second leading cause of cancer mortality worldwide, with approximately 600,000 cancer related deaths. Altered translation initiation and abnormal gene expression increase the risk of cancer development. Previous studies displayed, that deregulation along the eIF cascade disassociated with malignant transformation and progression of cancer. The goal in this example was to analyze the contribution of various eIFs and their relating upstream mTOR targets in CRC (colorectal carcinoma), to find a link between translation initiation and carcinogenesis. A constitutive activation of mTOR signaling is shown to be a hallmark of cancer and is associated to cell growth and cell cycle progression. mTOR is a downstream target of AKT, which is highly overexpressed in CRC. AKT can be inhibited by the phosphatase and tensin homolog (PTEN), which acts as tumor suppressor. The loss of PTEN in mice results in formation of different cancer types. Active mTOR further phosphorylates its downstream targets S6K and 4E-BPT. Due to phosphorylation, 4E-BP1 dissociates from eIF4E and cap depended translation initiation is performed. Inhibition of mTOR expression by knock down experiments results in considerably decreased in vitro and in vivo cell growth in CRC.

eIF5A, an indispensable member of the translation initiation process, is found to be aberrantly expressed in different malignancies including HCC, ovarian cancer, and lung cancer. One of its isoforms, eIF5A2, is overexpressed in HCC tissues, and this up-regulation may be a result of chromosome 3q amplification where the eIF5A2 gene resides. Clinical studies have demonstrated a correlation between up-regulation of eIF5A2 level with tumor metastasis and venous infiltration. Therefore, eIF5A2 has been proposed as an indicator of tumor invasiveness in HCC. In addition, targeting eIF5A2 by siRNA and combined treatment with GC7 effectively reduces the migration ability of tumor cells, suggesting that targeting eIF5A2 and hypusination could be a potential treatment for HCC.

eIF4E is involved in the regulation of the mRNA translation process. It can enhance the translation of some important growth factors and cell growth regulators and affect protein synthesis, the cell cycle, cancer gene activation, and apoptosis; it also play an important role in malignant transformation and metastasis. eIF4E regulates the translation of cancer-related mRNAs that are involved in tumor occurrence and development.

Previous studies showed an overexpression in malignant tumors including head and neck squamous cell carcinoma, laryngeal cancer, lung cancer, breast cancer, thyroid cancer and other cancer tissues. However, studies of eIF4E in liver cancer are rare. Studies showed that the protein expression three liver cancer cell lines were higher than in normal liver tissue. The HepG2 cell line had an especially high level of eIF4E protein expression. Based on these studies, eIF4E protein expression may be closely associated with the occurrence of human liver cancer development and prognosis. It has been confirmed in vivo and in vitro that sorafenib treatment can inhibit the RAF/MEK/ERK signaling transduction pathway, reduce the eIF4E phosphorylation level, reduce Mcl-1 protein, and induce hepatoma cell apoptosis. Accordingly, that lower levels of eIF4E gene expression may inhibit liver cancer. Targeting and adjusting the eIF4E level and activity may inhibit cancer cell growth, which may become a new paradigm in the field of biological treatment of liver cancer.

Collectively, our data show that there are different eIF expressions in HCC and that some eIF subunits are overexpressed in HCC compared to normal liver tissue and therefore we aimed at elucidative the involvement of eIFs in the development of HCC formation and progression.

The involvements of eIFs in cancer formation has been suggested and already, at least in part, have been proven for many eIF subunits and various tumor entities. eIFs can play a role, depending on the particular subunit and the respectively evaluated tissue types, in tumor development. The network of eIFs seems to display all elements of an entire oncogenic as well as tumor suppressive cascade. This thereby implicates enhanced eIF activation in HCC progression and suggests that eIFs may be an attractive target for HCC therapy.

Example 5: Colorectal Carcinoma

Colorectal cancer (CRC) is the third most common cause of cancer related death and with more than one million cases annually the third most frequently diagnosed cancer entity worldwide. The risk factors for CRC comprise high fat intake, alcohol, red meal, obesity, smoking, increasing age and physical inactivity and is more prevalent in developed than developing countries. Current clinical management strategies include surgery, chemotherapy, radiation and palliative care, but they are not as effective as previously expected. Various numbers of drugs were shown to have antitumor activity against CRC or metastatic CRC, but improvements in the efficacy of current medications are necessary.

Therefore it is important to better understand the pathogenesis of CRC in detail. Deregulation of protein synthesis has a major impact on cancer formation and progression.

Materials and Methods

Human Colorectal Cancer Samples

Formalin fixed paraffin embedded CRC samples and liver metastases from CRC patients and respective healthy control tissue from a total of 44 patients were collected and were used to generate 2 tissue microarrays (TMAs). The histological diagnosis, differentiation, and stage were classified according to the WHO classification (S. Hamilton, et al. World Health Organization Classification of Tumours International Agency for Research on Canccer (IARC) 2000; IARC Press).

The CRC TMA was composed of 346 tissue spots including carcinoma and healthy tissue of 16 patients suffering from CC (50% female; 50% male) and 11 patients with RC (27% female; 73% male). In addition a Liver-Metastases TMA (LM TMA) was generated. This included liver metastasis tissue from 11 CC (27% female; 73% male) and 6 RC patients (100% male) with respective healthy liver control tissue. Multiple metastases of these patients were used to generate the LM TMA with a total of 185 spots.

10 primary CC, 10 healthy colon controls and 10 primary RC, 10 healthy rectum controls served as protein- and mRNA controls.

Chemosensitivity Testings

TABLE 10

Chemotherapeutic drugs used for chemosensitivity testing.

| Drug | Subclass |
| --- | --- |
| Oxaliplatin* | Alkylating agent |
| Irinotecan* | Topoismerase I Inhibitor |
| 5-FU* | Antimetabolite (Pyrimidinantagonist) |
| Cetuximab* | Epidermal growth factor receptor inhibitor |
| AZD8931 | Reversible inhibitor of signaling by epidermal growth factor receptor |
| AZD6244 | Mitogen-activated protein kinase kinase (MEK or MAPK/ERK kinases) 1 and 2 inhibitor |
| Afatinib | Tyrosine Kinase inhibitor |
| Avastin* | Angiogenesis inhibitor |
| Regorafenib* | Multi-kinase inhibitor |
| Nintedanib | Angiokinase inhibitor for VEGFR1/2/3, FGFR1/2/3 and PDG-FRα/β |
| mTOR FR | mTOR inhibitor |
| IGF 1/2 mAB ** | IGF-1/IGF-2 co-neutralizing monoclonal antibody |
| AZ1 ** | Aziridinylbenzoquinone |
| Volitinib ** | c-Met inhibitor |

Standard drugs for CRC treatment*;
Novel drugs in preclinical testing **.

Cell Culture HCT116

HCT116 cell lines obtained from the American Type Culture Collection (ATCC) and were maintained in McCoy 5A medium supplemented with 10% fetal bovine serum (FBS) and penicillin/streptomycin (100 μg/ml), and incubated in a humidified atmosphere of 5% $CO_2$ at 37° C.

Results

Overexpression of Members of the mTOR Pathway in Rectum Carcinoma Compared to Colon Carcinoma Protein expression of mTOR, PTEN, 4E-BP1 and AKT was significantly upregulated in RC samples compared to healthy control tissue (p<0.05). In CC mTOR, PTEN and 4E-BP1 revealed no significant changes in comparison to healthy control tissue besides AKT (p<0.05) showing a significant upregulation. Compared to CC statistical analysis revealed a significant upregulation of PTEN and 4E-BP1 in RC (p<0.05). Compared to healthy control tissue, CC and RC tissues revealed no obvious changes in their phosphorylation status concerning phospho mTOR Ser2448, phospho PTEN Ser380, phospho 4EBP1 Ser65 and phospho AKT Ser478.

The results of the quantitative RT-PCR, with actin as internal reference, showed mTOR and PTEN as abundantly expressed in RCs, but not in CCs.

Expression of eIF3, eIF4 and their Subunits in CRC

IHC was performed on the CRC TMA representing different eIF subunits. Density of the IHC staining was predominantly evaluated as 100%.

Immunohistochemistry of the analyzed eIF subunits did not show significant differences comparing CRC tissue and respective healthy control tissue. The observed staining intensities displayed an irregular expression pattern. IHC staining for eIF3H revealed strong staining in 100% of CRC tissue samples and healthy control samples. The staining for eIF3A and eIF3B displayed strong to weak staining intensities with irregular expression pattern. eIF3M revealed no staining in CRC tissue and respectively healthy control tissue.

Compared to the healthy colon and rectum tissues, eIF3A, eIF3B, eIF3B, eIF3D and eIF3M were significantly increased on protein level in CC and RC samples (p<0.05) (FIG. 13A). On mRNA level eIF3A and eIF3B revealed a significant upregulation in RC samples. eIF3B displayed the highest upregulation by factor 40 (p<0.05), followed by eIF3A being about 28 fold increased (p<0.05). In comparison to CC eIF3H and eIF3M were increased on mRNA level, but no significant difference was observed on protein level (FIG. 13B).

The protein expression of eIF3C, eIF3j and eIF3K was significantly upregulated in RC compared to CC and healthy tissue (p<0.05) (FIG. 13A). The mRNA expression of eIF3C and eIF3j showed an overexpression in RC compared to CC samples (FIG. 13B) compared to RC samples and healthy tissue.

Immunohistochemistry of the analyzed eIF subunits did not show significant differences comparing CRC tissue and respectively healthy control tissue. The observed staining intensities displayed an irregular expression pattern. The staining for eIF4E and eIF4G displayed strong to weak staining intensities with irregular expression pattern.

Compared to healthy control tissue, protein expression of Phosphor eIF4B, eIF4B and eIF4G was significantly increased in CC and RC samples. In CC tissue eIF4B showed the highest upregulation by factor 20 (p<0.05), followed by eIF4G being about 13 fold increased (p<0.05). The same could be detected in RC tissue. In case of CC, eIF4G showed the highest increase by 16 fold overexpression, eIF4B with a 6 fold overexpression. Statistical analysis of CC and RC samples revealed a significant upregulation of eIF4B in CC compared to RC (p<0.05) (FIG. 14A).

Compared to healthy rectum control tissue, protein expression of eIF4E was significantly upregulated in RC samples. Protein expression of eIF4E was 5.5 times upregulated in RC (p<0.05) whereas in CC no significant changes were detectable. Statistical analysis revealed a significant upregulation of eIF4E in RC compared to CC (p<0.05) (FIG. 14A).

The results of mRNA expression analysis of eIF4B and eIF4E demonstrated no changes of expression in CC and RC samples compared to normal controls. However, eIF4G displayed a higher mRNA expression in RC compared to CC samples (FIG. 14B).

Expression of eIF2α, eIF5 and eIF6 in CRC

IHC of the analyzed eIF subunits did not show significant differences comparing CRC tissue and respectively healthy control tissue. The observed staining intensities displayed an irregular expression pattern.

IHC staining for eIF2α revealed strong staining in 100% of CRC tissue samples and healthy control samples. The staining for eIF6 displayed strong to weak staining intensities with irregular expression pattern.

Protein expression of eIF2α was significantly upregulated in CC samples (p<0.05). eIF2α was 4.5 times upregulated in CC (p<0.05) whereas in RC no significant changes were detectable compared to healthy tissue. eIF5 and eIF6 were significantly increased in CC and RC samples compared to control tissue. ImageJ analysis of eIF5 and eIF6 protein pattern revealed a significant 4 fold upregulation in CC and RC tissue (p<0.05) (FIG. 15A).

Protein Expression of Eukaryotic Initiation Factors in Colon Cancer Patients Derived Xenograft Models To display protein expression of different eIF subunits during chemotherapeutic treatment, 4 colon primary carcinoma PDX models and 1 colon metastasis PDX model were generated. In comparison to untreated control, mTOR showed a trend to be upregulated under treatment with Oxaliplatin and Cetuximab in colon primary carcinoma PDX models. A partly downregulation was visible in the AZ1 treated CPC PDX model. Protein expression of mTOR in the colon metastasis (CM) PDX model revealed a tendency to be upregulated under Afatinib treatment. According to untreated control, mTOR, eIF2α, eIF3J, eIF4B and eIF5 showed a tendency to be increased in the Afatinib treated CM PDX model. In addition PTEN seemed to be decreased in the Avastin treated CM PDX model. Protein expression of PTEN, eIF2α, eIF3A, eIF3J, eIF3B, eIF4B, eIF4G and eIF5 was heterogeneous and displayed no visible changes comparing untreated and treated colon cancer tissue. Statistical analysis using the Kruskal-Wallis test revealed that the observed tendencies were not statistically significant.

Protein Expression of Eukaryotic Initiation Factors in Colon Cancer Patients Derived Xenograft Models To analyze protein expression of different eIF subunits under chemotherapeutic treatment, 4 rectum primary carcinoma (RPC) PDX models and 2 rectum metastasis (RM) PDX model were generated. Protein expression of eIF3J showed a tendency to be downregulated in RM PDX models under treatment with Nintedanib, mTOR FR and IGF 1/2 mAB. In addition these models displayed a trend in downregulation of eIF3A under treatment with Irinotecan, 5-FU, Avastin, Regorafenib, Nintedanib and mTOR FR. Protein expression of eIF4G was increased in Oxaliplatin and Cetuximab treated RPC PDX.

Protein expression of PTEN, eIF2α, eIF3J, eIF3B, eIF4B and eIF5 was heterogeneous and displayed no visible changes comparing untreated and treated rectum cancer tissue.

Statistical analysis using the Kruskal-Wallis test revealed that the observed tendencies were not statistically significant.

IHC Staining of Liver Metastases from CRC

Density of the IHC staining was evaluated as 100%. In comparison to healthy liver tissue, several eIFs were highly upregulated in liver metastases which were derived from CRC.

Figure 6B:
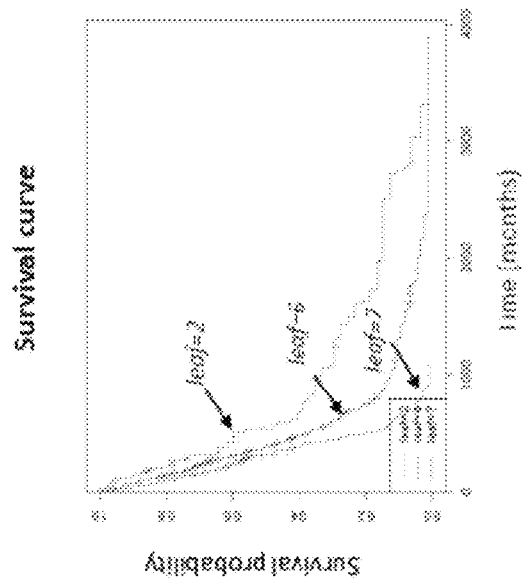
FIGS. 6A-6D shows the correlation of eIF gene expression with survival probabilities of GBM patients using the TCGA database. Statistical decision trees were generated for eIF gene expression without any exclusion criteria (FIG. 6A) and with the exclusion of TMZ treated patients (FIG. 6C). For each decision tree, survival curves for all patients (FIG. 6B) und and patients without TMZ treatment (FIG. 6D) were prepared. Numbers: Total patients: n=535, patients without TMZ: n=230.
Figure 6A:
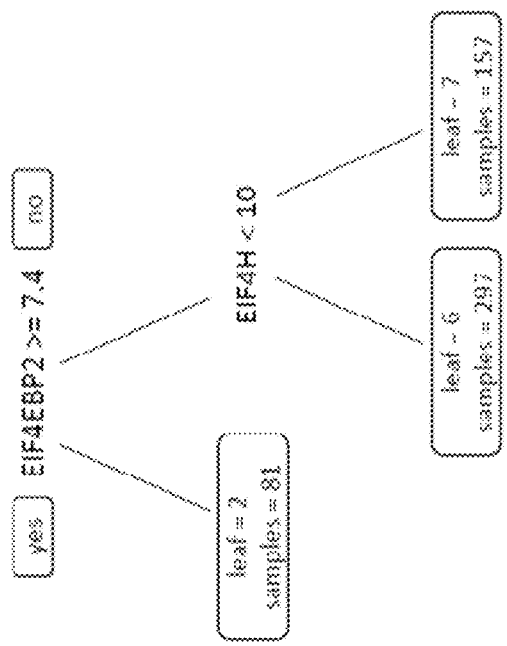
Figure 6D:
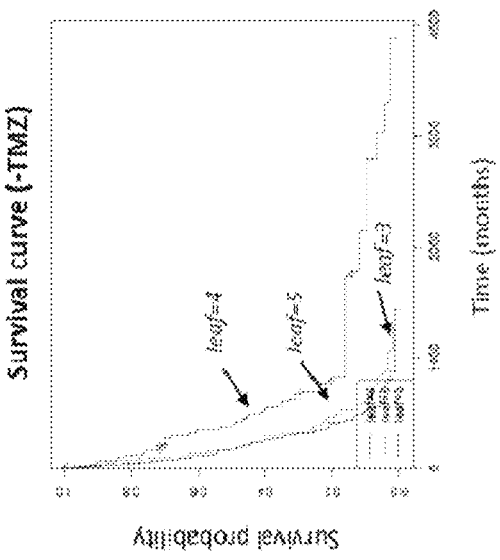

IHC staining for eIF1 revealed no staining in healthy liver tissue samples, whereas liver metastases from CC and RC displayed a moderate to strong staining intensity (FIGS. 5A and 5B). The same was observed for IHC staining for eIF2α (FIGS. 5A and 5B), eIF3H (FIGS. 6A and 6B), eIF3B (FIGS. 5A and 5B) and eIF4G (FIGS. 6A and 6B). IHC staining for eIF4E (FIGS. 6A and 6B) revealed a moderate to high staining intensity in 63% of liver metastases from CC, whereas the intensity in metastases from RC was 90%. The same tendency was observed for eIF6 (FIGS. 6A and 6B) and eIF3A (FIGS. 5A and 5B).

mRNA Expression of eIF Subunits in Liver Metastases from CRC

Figure 6C:
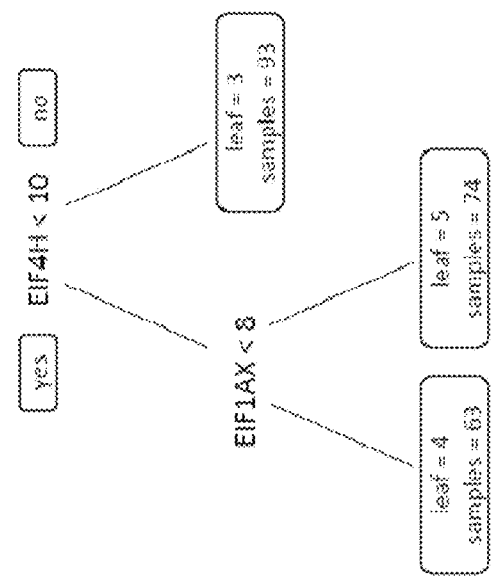

The mRNA expression results verified the IHC staining for all eIFs, they showed a strong upregulation in liver metastases compared to healthy liver tissue. Compared to respective healthy control tissue, mRNA expression levels of eIF1, eIF3B (FIG. 5C), eIF4E and eIF4G (FIG. 6C) were significantly higher in liver metastases from CC and RC. In comparison to healthy liver tissue, mRNA expression of eIF2α, eIF3A (FIG. 5C) and eIF6 (FIG. 6C) was significantly upregulated in RC liver metastases, therefore, eIF3A was upregulated with a 28 fold increase ($p<0.05$) (FIG. 5C). eIF2α revealed a significant 20 fold upregulation (FIG. 5C). A 12 fold increase was observed for eIF6 ($p<0.05$) (FIG. 6C). Real-time analysis of eIF3C revealed a high upregulation 0.05) in CC liver metastases compared to healthy liver control tissue).

Silencing of eIF1, eIF5 and eIF6 in CRC Cell Lines

Based on the results of the eIF characterization in CC patients, eIF1, eIF5 and eIF6 turned out to be mainly altered and are thus promising candidates for future therapeutic approaches. Thus, in order to investigate the effect of silencing eIF1, eIF5 and eIF6, HCT116 cells were transfected with a siRNA and the subsequently knockdown effect was assessed for three time points. An inhibition of protein levels close to 90% was achieved for eIF1, eIF5 and eIF6 at all three time points. The transfection strongly reduced the proliferation of HCT116 cells which expressed eIF1, eIF5 and eIF6 specific siRNAs, but had no effect on MOK control.

After transfection of HCT 116 cells with the respective siRNAs for 24h, 48h and 72h, mRNA expression of eIF1, eIF5 (24h $p<0.01$, $p<0.05$, $p<0.01$; 48h $p<0.001$; 72h $p<0.001$, $p<0.01$, $p<0.01$) and eIF6 (48h $p<0.001$; 72h $p<0.05$) in HCT116 cells were reduced for all three subunits compared to a negative control group. Moreover, the Immunoblotting results suggested a reduction of the protein levels by the silenced eIF1, eIF5 and eIF6 genes. The siRNA of eIF1, eIF5 and eIF6 gene constructs effectively inhibited the expression of eIF1, eIF5 and eIF6 gene. The effect of eIF1, eIF5 and eIF6 gene knockdown on apoptosis was analyzed by comparing the apoptosis levels upon eIF1, eIF5 and eIF6 knockdown with negative control cells by a YO-PRO®-1 staining. The apoptosis rate of the transfected cells with eIF1 (72h $p<0.05$), eIF5 (72h $p<0.05$, $p<0.001$) and eIF6 knockdown constructs (48h $p<0.001$; 72h $p<0.001$) was significantly decreased compared to negative control cells 72h after transfection with siRNA.

After eIF1, eIF5 and eIF6 silencing, in vitro cell viability was significantly reduced. eIF1 (24h $p<0.001$; 48h $p<0.001$, $p<0.01$; 72h $p<0.001$), eIF5 (24h $p<0.001$, $p<0.01$; 48h $p<0.001$; 72h $p<0.001$) and eIF6 (24h $p<0.001$; 48h $p<0.001$; 72h $p<0.001$) silencing lead to a reduction of cell viability at all 3 time points (24h, 48, 72h).

Furthermore, clonogenicity as evaluated by Giemsa staining. Colony formation was reduced 14 days after seeding in all transfected cells. The effect of eIF1, eIF5A and eIF6 knockdown on CRC cell motility was investigated by identifying the transmigration competence of cells through filters coated with an extracellular matrix. The cells exhibited a reduced capability to transmigrate upon eIF1, eIF5 ($p<0.05$, $p<0.01$) and eIF6 knockdown.

Silencing of eIF1, eIF5 and eIF6 Leads to Reduced Translation

The effects of eIF1, eIF5 and eIF6 knockdown on translation initiation were investigated by polysome profiling. After sucrose density gradient centrifugation of cell lysates, polysomes, 80S ribosomes and free 40S and 60S subunits were detected by monitoring their A254 nm as described in the methods section.

Non-transfected HTC116 cells showed some free, unjoined 40S and 60S subunits, a large 80S peak and low amounts of polysomes. After eIF1 knockdown, increased levels of free 60S subunits, and a marked decrease of the 80S peak were observed, suggesting a defect in translation initiation. Furthermore, less polysomes were recorded in the eIF1 knockdown profile, indicating reduced translation rates. eIF5 knockdown also led to decreased levels of polysomes. In addition, the levels of free 40S and 60S ribosomal subunits relative to 80S ribosomes were increased, suggesting less efficient translation initiation. Similarly, also eIF6 knockdown resulted in a decrease in polysomes and an increase of the levels of free ribosomal subunits relative to 80S ribosomes.

To conclude, knockdown of all three initiation factors caused defects in translation initiation, resulting in a reduction of polysomes indicating reduced overall translation.

Discussion

In this example it could be shown that protein expression pattern of pmTOR/mTOR, pPTEN/PTEN, p4EBP1/4EBP1 was significantly upregulated in RC samples compared to healthy rectum tissue. Increased levels of activated mTOR and 4E-BP1 might indicate the promotion of cap dependent translation and the involvement of the mTOR pathway to CRC carcinogenesis. Increased protein expression of mTOR and 4E-BP1 might also indicate the observed PTEN upregulation not sufficiently blocking their phosphorylation. Protein expression of pAKT/AKT was significantly upregulated in RC indicating increased activation of mTOR signaling and its downstream located eIF pathway components. Comparing CC and RC, PTEN was significantly increased in RC samples, which might indicate an increased inhibition of the mTOR pathway in rectum cancer. Also the mRNA data showed an abundant expression in RC compared to CC. Differences in the expression between CC and RC for eIF3C, elf3j and eIF3K were also observed, the protein level in RC tissue was increased. eIF3K was shown to interact with other eIF3 members including eIF3C and eIF3j and is suggested to be implicated in other processes, beyond translation initiation. eIF3C was found to be an oncogene and was shown to be significantly increased in cancer cells. An increase of eIF3H and eIF3M in CC and RC samples was also observed. Previous studies indicated eIF3H as being associated with CRC risk and suggested eIF3H to act as CRC susceptibility gene. eIF3 subunits are targeted in therapies for muscle atrophy and viral infection, but no eIF3 targeting agent is available for cancer therapy yet.

Obtained protein data revealed a significant upregulation of eIF4B, eIF4B and eIF4G in CC and RC samples and demonstrated an increase for eIF4E only in RC samples compared to healthy control tissue. The mRNA expression analysis of eIF4B and eIF4E demonstrated no changes of expression in CC and RC samples compared to normal controls. In comparison a higher mRNA expression of eIF4G was found in RC compared to CC samples.

eIF4B has been reported to modulate, in addition to eIF4G, the helicase activity of eIF4A and to establish bridges between mRNA and the 40S ribosomal subunit. Phosphorylation of eIF4B strengthens its interaction with eIF3A. Upon knockdown of eIF4B in HCT116 cells attenuated proliferation and increased stress-driven apoptosis was observed.

The present protein data revealed a significant upregulation of various eIF subunits in CRC tissue. Protein expression of eIF2α was significantly upregulated in CC compared to healthy colon controls. This may indicate an increased level of tumor initiation and progression of CC. It is known that eIF5 is one of the essential core proteins of translation initiation. eIF6 operates as ribosomal anti-associated factor that binds to 60S ribosomal subunits in the nucleus and releases them into the cytoplasm after phosphorylation by growth factors. Interaction of the 60S with the 40S subunit is held and therefore translation initiation is blocked. eIF6 expression also limits cell growth and transformation. It is known that eIF6 is part of a multi-protein complex connected with the RNA-induced silencing complex (RISC), which is the major complex regulating miRNA activity. Previous studies showed that eIF6 is overexpressed in ovarian serous carcinoma, leukemia, head and neck carcinoma, as well as CC. We also saw a significant increase of eIF6 but only on mRNA level in high grade CC and RC samples. These findings suggest that eIF6 may play a central role in the translation initiation in low and high grade CC and RC.

It was previously also shown that eIF5 is one of the essential core proteins of translation initiation. eIF5 is associated with eIF1, which is able to directly assemble with eIF3 and the (eIF2)-GTPMet-tRNAiMet. eIF5 over-expression was shown in different cancer types and is considered as predictive tumor marker. eIF1 was demonstrated to bind eIF5 and thereby potentially interferes with its GAP function. Previous studies in yeast showed that the interaction between eIF1 shift the 43S complex into a scanning-incompetent state, stalling it at the AUG. eIF5 overexpression involved in ovarian cancer and is regarded as a predictive tumor marker.

As the eIF subunits 1, 5 and 6 seemed to be the most promising candidates in targeting CRC we also investigated them more detailed in knockdown experiments. eIF1, eIF5 and eIF6 were confirmed to be involved in cell proliferation by silencing in human CRC cell line HCT 116. After successful knockdown of eIF1, eIF5 and eIF6 on mRNA and protein level, proliferation rate and clonability of HCT 116 cells were significantly inhibited. Apoptosis significantly increased at late stage (72h). Changes in translation control and protein synthesis are key roles in tumor formation. Regarding our results, they include changes in protein synthesis and selective translational control of mRNA, and inhibition of tumor cell apoptosis. The knockdown of eIF1, eIF5 and eIF6 result in a reduction of polysomes indicating reduced overall translation.

The invention claimed is:

1. A method for treating lung adenocarcinoma, comprising the step of:
    administering a eukaryotic initiation factor 6 (eIF6) small interfering RNA (siRNA) to a patient having lung adenocarcinoma, wherein the eIF6 siRNA comprises SEQ ID NO:5 or 6.

2. The method according to claim 1, wherein the eIF6 siRNA comprises SEQ ID NO:5.

3. The method according to claim 1, wherein the eIF6 siRNA comprises SEQ ID NO:6.

4. The method according to claim 1, wherein the eIF6 siRNA consists of SEQ ID NO:5.

5. The method according to claim 1, wherein the eIF6 siRNA consists of SEQ ID NO:6.

6. The method of claim 1, wherein the eIF6 siRNA is administered by intravenous, intramuscular, intrathecal, subcutaneous, transdermal or aerosol administration.

* * * * *